US009102669B2

(12) United States Patent
Yang et al.

(10) Patent No.: US 9,102,669 B2
(45) Date of Patent: Aug. 11, 2015

(54) SUBSTITUTED PIPERIDINYL-PYRIDAZINYL DERIVATIVES USEFUL AS SCD 1 INHIBITORS

(71) Applicant: Janssen Pharmaceutica NV, Beeerse (BE)

(72) Inventors: Shyh-Ming Yang, Doylestown, PA (US); Gee-Hong Kuo, Scotch Plains, NJ (US); Micheal D. Gaul, Yardley, PA (US); Thomas A. Rano, Branchburg, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/363,051

(22) PCT Filed: Dec. 5, 2012

(86) PCT No.: PCT/US2012/067877
§ 371 (c)(1),
(2) Date: Jun. 5, 2014

(87) PCT Pub. No.: WO2013/085957
PCT Pub. Date: Jun. 13, 2013

(65) Prior Publication Data
US 2014/0371220 A1 Dec. 18, 2014

Related U.S. Application Data

(60) Provisional application No. 61/567,185, filed on Dec. 6, 2011.

(51) Int. Cl.
C07D 295/00 (2006.01)
C07D 417/14 (2006.01)
C07D 401/14 (2006.01)
C07D 413/14 (2006.01)
C07D 409/14 (2006.01)

(52) U.S. Cl.
CPC ............ *C07D 417/14* (2013.01); *C07D 401/14* (2013.01); *C07D 409/14* (2013.01); *C07D 413/14* (2013.01)

(58) Field of Classification Search
USPC ....................................................... 546/184
See application file for complete search history.

(56) References Cited

U.S. PATENT DOCUMENTS

| | | | |
|---|---|---|---|
| 5,225,402 | A | 7/1993 | Ogawa et al. |
| 5,356,904 | A | 10/1994 | Freidinger et al. |
| 5,436,254 | A | 7/1995 | Ogawa et al. |
| 5,652,247 | A | 7/1997 | Ogawa et al. |
| 5,985,878 | A | 11/1999 | Stokbroekx et al. |
| 6,509,340 | B1 | 1/2003 | Van Amsterdam et al. |
| 2004/0220191 | A1 | 11/2004 | Schwink et al. |
| 2007/0207991 | A1 | 9/2007 | Schwink et al. |
| 2009/0163545 | A1 | 6/2009 | Goldfarb |

FOREIGN PATENT DOCUMENTS

| | | |
|---|---|---|
| EP | 2316458 A1 | 5/2011 |
| WO | WO 94/01113 A1 | 1/1994 |
| WO | WO 97/26258 A1 | 7/1997 |
| WO | WO 98/58929 A1 | 12/1998 |
| WO | WO 00/26203 A1 | 5/2000 |
| WO | WO 00/37456 A1 | 6/2000 |
| WO | WO 02/055514 A2 | 7/2002 |
| WO | WO 03/037890 A2 | 5/2003 |
| WO | WO 2004/072025 A2 | 8/2004 |
| WO | WO 2007/076055 A2 | 7/2007 |
| WO | WO 2007/130383 A2 | 11/2007 |
| WO | WO 2011/015629 A1 | 2/2011 |
| WO | WO 2013/085954 A1 | 6/2013 |

OTHER PUBLICATIONS

International Search Report relating to International Patent Application No. PCT/US2012/067877, filed Dec. 5, 2012. Date of Mailing of International Search Report: Feb. 1, 2013.
Written Opinion of the International Searching Authority relating to International Patent Application No. PCT/US2012/067877, filed Dec. 5, 2012. Date of Mailing of Written Opinion: Feb. 1, 2013.
Bongartz, J-P., et al., Synthesis and Anti-Angiogenic Activity of 6-(1,2,4-Thiadiazol-5-yl)-3-aminopyridazine Derivatives, *Bioorg. Med. Chem. Lett.*, 2002, pp. 589-591, vol. 12(4).
Database Registry [Online], Chemical Abstracts Service, Columbus, Ohio, U.S., Mar. 30, 2008, XP002691195.
Dobrzyn, A., et al., "Stearoyl-CoA desaturase as a new drug target for obesity treatment" *Obes. Rev.*, 2005, pp. 169-174, vol. 6.
Liu, G., "Stearoyl-CoA desaturase inhibitors: update on patented compounds." *Expert Opin. Ther. Patents*, 2009, pp. 1169-1191, vol. 19(8).
Miyazaki, M., et al., "Identification and characterization of murine SCD4, a novel heart-specific stearoyl-CoA desaturase isoform regulated by leptin and dietary factors", *J. Biol. Chem.*, 2003, pp. 33904-33911, vol. 278.
Miyazaki, M., et al., "Lack of stearoyl-CoA desaturase-1 function induces a palmitoyl-CoA Δ6 desaturase and represses the stearoyl-CoA desaturase-3 gene in the preputial glands of the mouse", *J. Lipid Res.*, 2002, pp. 2146, vol. 43.
Miyazaki, M., et al., "The biosynthesis of hepatic cholesterol esters and triglycerides is impaired in mice with a disruption of the gene for stearoyl-CoA desaturase 1", *J. Biol. Chem.*, 2000, pp. 30132-30138, vol. 275.
Ntambi, J., et al., "Recent insights into stearoyl-CoA desaturase-1", *Curr. Opin. Lipidol.*, 2003, pp. 255-261, vol. 14.
Ntambi, J.M. et al., "Loss of stearoyl-CoA desaturase-1 function protects mice against adiposity", *Proc. Natl. Acad. Sci. U.S.A.*, 2002, pp. 11482-11486, vol. 99.
Ntambi, J.M., et al., "Regulation of stearoyl-CoA desaturase by polyunsaturated fatty acids and cholesterol", *J. Lipid Res.*, 1999, pp. 1549-1558, vol. 40.

(Continued)

Primary Examiner — James O Wilson
Assistant Examiner — Oluwafemi Masha

(57) ABSTRACT

The present invention is directed to novel piperidinyl-pyridazinyl derivatives, pharmaceutical compositions containing them and their use as inhibitors of SCD1, useful in the treatment of obesity, type-II diabetes and other related metabolic disorders.

13 Claims, No Drawings

(56) References Cited

OTHER PUBLICATIONS

Ntambi, J.M., et al., "Regulation of stearoyl-CoA desaturases and role in metabolism", *Prog. Lipid Res.*, 2004, pp. 91-104, vol. 43.

Wang, J., et al., "Characterization of HSCD5, a novel human stearoyl-CoA desaturase unique to primates", *Biochem. Biophys. Res. Commun.*, 2005, pp. 735-742, vol. 332.

Waters, K.M., et al., "Insulin and Dietary Fructose Induce Stearoyl-CoA Desaturase 1 Gene Expression in Liver of Diabetic Mice*", *J. Biol. Chem.*, 1994, pp. 27773-27777, vol. 269.

Zhang, L., et al., "Human stearoyl-CoA desaturase: alternative transcripts generated from a single gene by usage of tandem polyadenylation sites", *Biochem. J.*, 1999, pp. 255-264, vol. 340.

Zheng, Y., et al., "SCD1 is expressed in sebaceous glands and is disrupted in the asebia mouse", *Nat. Genet.*, 1999, pp. 268-270, vol. 23.

SUBSTITUTED PIPERIDINYL-PYRIDAZINYL DERIVATIVES USEFUL AS SCD 1 INHIBITORS

This application is a national stage of Application No. PCT/US2012/067877, filed Dec. 5, 2012, which claims of the benefit of U. S. Provisional Application 61/567,185, filed on Dec. 6, 2011.

FIELD OF THE INVENTION

The present invention is directed to novel piperidinyl-pyridazinyl derivatives, pharmaceutical compositions containing them and their use as inhibitors of SCD 1, useful in the treatment of obesity, type-II diabetes and other related metabolic disorders.

BACKGROUND OF THE INVENTION

Stearoyl-CoA desaturase 1 (SCD 1) is a critical microsomal enzyme that catalyzes the conversion of saturated fatty acid-CoAs to mono-unsaturated fatty acid-CoAs (at C-9 position) (DOBRZYN, A., et al., *Obes. Rev.*, 2005, pp 169, Vol. 6; NTAMBI, J., et al., *Curr. Opin. Lipidol.*, 2003, pp 255, Vol. 14). These mono-unsaturated fatty acid-CoAs, such as palmitoleic (C16) acid-CoA and oleic (C18) acid-CoA, are major building blocks in biosynthesis of lipids including phospholipids, triglycerides, cholesterol esters and wax esters (MIYAZAKI, M., et al., *J. Lipid Res.*, 2002, pp 2146, Vol. 43). Four SCD isoforms (SCD 14) in rodents and two human genes (SCD 1 and 2) have been identified and characterized. SCD 1 (MIYAZAKI, M., et al., *J. Biol. Chem.*, 2003, pp 33904, Vol 278; WANG, J., et al., *Biochem. Biophys. Res. Commun.*, 2005, pp 735, Vol. 332), with ca. 85% identity across species (ZHANG, L., et a., *Biochem. J.*, 1999, pp 255, Vol. 340), is abundantly expressed in liver and adipose tissue and is regulated by several nutritional and hormonal factors, such as insulin, cholesterol, and poly-unsaturated fatty acids (WATERS, K. M., et al., *J. Biol. Chem.*, 1994, pp 27773, Vol. 269; NTAMBI, J. M., et al., *J. Lipid Res.*, 1999, pp 1549, Vol. 40). Moreover, SCD 1 deficiency in mice, either naturally deficient Asebia mice (ZHENG, Y., et al., *Nat. Genet.*, 1999, pp 268, Vol. 23) or laboratory-created SCD 1 knockout (SCD 1$^{-/-}$) mice (NTAMBI, J. M. et al., *Proc. Natl. Acad. Sci. U.S.A.*, 2002, pp 11482, Vol. 99), has been shown to reduce body adiposity, increase insulin sensitivity, and impart resistance to diet-induced obesity (NTAMBI, J. M., et al., *Prog. Lipid Res.*, 2004, pp 91, Vol. 43). The SCD 1$^{-/-}$ mice also have lower levels of hepatic cholesterol esters and triglycerides (MIYAZAKI, M., et al., *J. Biol. Chem.*, 2000, pp 30132, Vol. 275).

These observations indicated that inhibition of SCD 1 activity may serve as a potential treatment for obesity, type-II diabetes, and other related metabolic disorders.

SUMMARY OF THE INVENTION

The present invention is directed to compounds of formula (I)

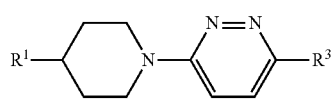

(I)

wherein
$R^1$ is selected from the group consisting of

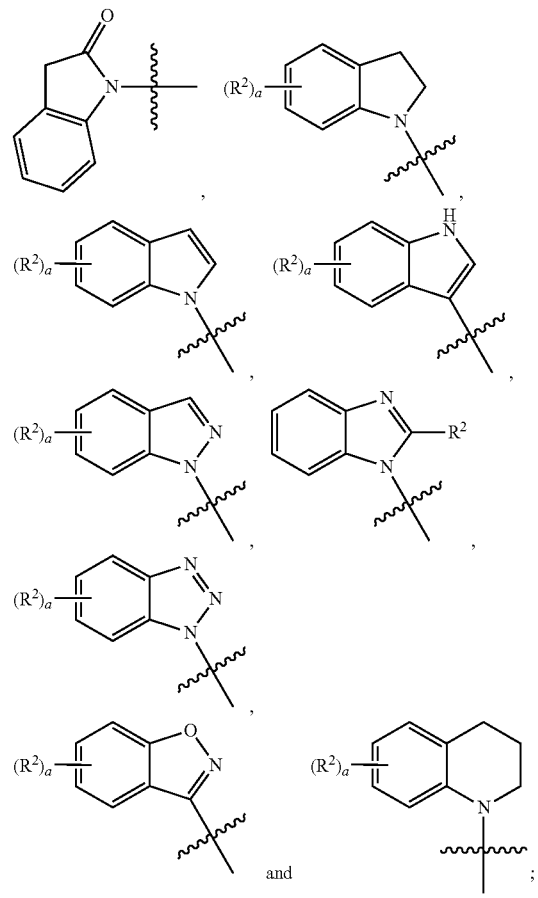

and ;

a is an integer from 0 to 3;

each $R^2$ is independently selected from the group consisting of halogen, $C_{1-4}$alkyl, $C_{1-4}$alkoxy, halogenated $C_{1-2}$alkyl, and halogenated $C_{1-2}$alkoxy;

$R^3$ is selected from the group consisting of (a)

(b)

(c)

(d)

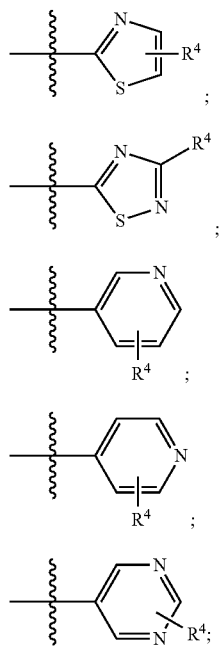

(e), (f), (g), (h), (i)

wherein $R^4$ is selected from the group consisting of hydrogen, halogen, $C_{1-4}$alkyl, halogenated $C_{1-2}$alkyl, —$C_{1-2}$alkyl-OH, $C_{1-4}$alkoxy, halogenated $C_{1-2}$alkoxy, —$C_{1-2}$alkyl-O—$C_{1-2}$alkyl, —$CO_2H$, —$C(O)O$—$C_{1-4}$alkyl, —$C_{1-2}$alkyl-C(O)O—$C_{1-2}$alkyl, —$C_{1-2}$alkyl-OC(O)—$C_{1-2}$alkyl, —$NR^AR^B$, —$C_{1-2}$alkyl-$NR^AR^B$, —$C(O)$—$NR^AR^B$, —$C_{1-2}$alkyl-C(O)—$NR^AR^B$ and —$NR^A$—$C(O)$—($C_{1-2}$alkyl);

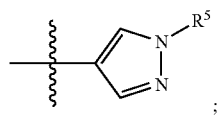

(j)

wherein $R^5$ is selected from the group consisting of hydrogen, $C_{1-4}$alkyl, —$C_{2-4}$alkyl-OH, —$C_{2-3}$alkyl-O—$C_{1-2}$alkyl, —$C_{1-2}$alkyl-C(O)O—$C_{1-2}$alkyl, —$C_{2-3}$alkyl-OC(O)—$C_{1-2}$alkyl, —$C_{2-4}$alkyl-$NR^AR^B$ and —$C_{1-2}$alkyl-C(O)$NR^AR^B$;

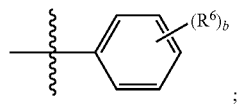

(k)

and
wherein b is an integer from 0 to 2;
wherein each $R^6$ is independently selected from the group consisting of halogen, $C_{1-4}$alkyl, halogenated $C_{1-4}$alkyl, —$C_{1-2}$alkyl-OH, $C_{1-4}$alkoxy, halogenated $C_{1-4}$alkoxy, —$C_{1-2}$alkyl-O—$C_{1-2}$alkyl, —$CO_2H$, —$C(O)O$—$C_{1-4}$alkyl, —$C_{1-2}$alkyl-C(O)O—$C_{1-2}$alkyl, —$C_{1-2}$alkyl-OC(O)—$C_{1-2}$alkyl, —$C(O)$—$NR^AR^B$, —$C_{1-2}$alkyl-C(O)—$NR^AR^B$, —$NR^AR^B$, —$C_{1-2}$alkyl-$NR^AR^B$ and —$NR^A$—$C(O)$—$C_{1-2}$alkyl;
and wherein $R^A$ and $R^B$ are each independently selected from the group consisting of hydrogen and $C_{1-2}$alkyl; alternatively $R^A$ and $R^B$ are taken together with the nitrogen atom to which they are bound to form piperidin-1-yl, piperazin-1-yl, morpholin-4-yl and pyrrolidin-1-yl;
provided that when $R^3$ is 3-methyl-1,2,4-thiadiazol-5-yl, then $R^1$ is other than unsubstituted indoly-3-yl;
and pharmaceutically acceptable salts thereof.

The present invention is further directed to processes for the preparation of the compounds of formula (I). The present invention is further directed to a product prepared according to the process described herein.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

Exemplifying the invention are methods of treating a disorder mediated by SCD1 (selected from the group consisting of obesity, type-II diabetes, Syndrome X (also known as metabolic syndrome), hypertriglyceridemia, dyslipidemia, hypercholesterolemia, hyperlipidemia, mixed dyslipidemia, fatty liver, nonalcoholic fatty liver disease, liver fibrosis and NASH) comprising administering to a subject in need thereof a therapeutically effective amount of any of the compounds or pharmaceutical compositions described herein.

In an embodiment, the present invention is directed to a compound of formula (I) for use as a medicament. In another embodiment, the present invention is directed to a compound of formula (I) for use in the treatment of a disorder mediated by SCD1 (selected from the group consisting of obesity, type-II diabetes, Syndrome X (also known as metabolic syndrome), hypertriglyceridemia, dyslipidemia, hypercholesterolemia, hyperlipidemia, mixed dyslipidemia, fatty liver, nonalcoholic fatty liver disease, liver fibrosis and NASH). In another embodiment, the present invention is directed to a composition comprising a compound of formula (I) for the treatment of a disorder mediated by SCD1 (selected from the group consisting of obesity, type-II diabetes, Syndrome X (also known as metabolic syndrome), hypertriglyceridemia, dyslipidemia, hypercholesterolemia, hyperlipidemia, mixed dyslipidemia, fatty liver, nonalcoholic fatty liver disease, liver fibrosis and NASH).

Another example of the invention is the use of any of the compounds described herein in the preparation of a medicament for treating: (a) obesity, (b) type-II diabetes, (c) Syndrome X (also known as metabolic syndrome), (d) hypertriglyceridemia, (e) dyslipidemia, (f) hypercholesterolemia, (g) hyperlipidemia, (h) mixed dyslipidemia, (i) fatty liver, (j) nonalcoholic fatty liver disease, (k) liver fibrosis or (l) NASH, in a subject in need thereof.

In another example, the present invention is directed to a compound as described herein for use in a methods for treating a disorder selected from the group consisting of obesity, type-II diabetes, Syndrome X (also known as metabolic syndrome), hypertriglyceridemia, dyslipidemia, hypercholesterolemia, hyperlipidemia, mixed dyslipidemia, fatty liver, nonalcoholic fatty liver disease, liver fibrosis and NASH, in a subject in need thereof.

DETAILED DESCRIPTION OF THE INVENTION

The present invention is directed to compounds of formula (I)

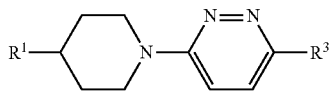

wherein $R^1$, $R^2$, $R^3$, $R^4$, $R^5$, $R^6$, a, and b are as herein defined. The compounds of the present invention are inhibitors of SCD1 useful in the treatment of metabolic disorders including, but not limited to, obesity, type-II diabetes, Syndrome X (also known as metabolic syndrome), hypertriglyceridemia, dyslipidemia, NASH, hypercholesterolemia, hyperlipidemia, mixed dyslipidemia, fatty liver, nonalcoholic fatty liver disease, liver fibrosis, and the like.

In an embodiment, the present invention is directed to compounds of formula (I) wherein, $R^1$ is selected from the group consisting of

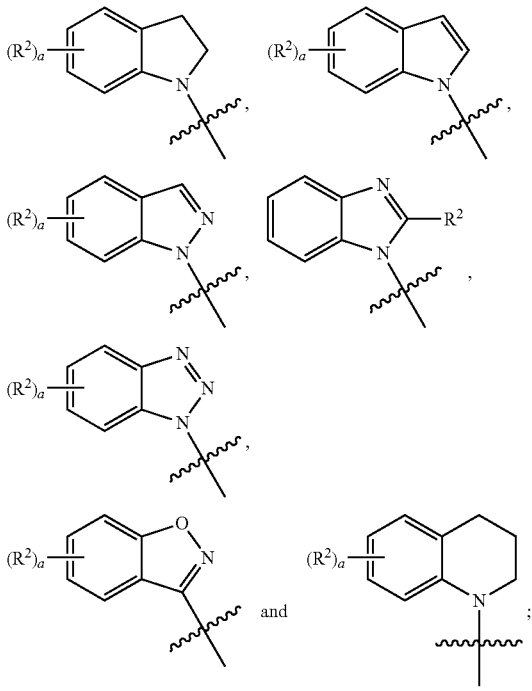

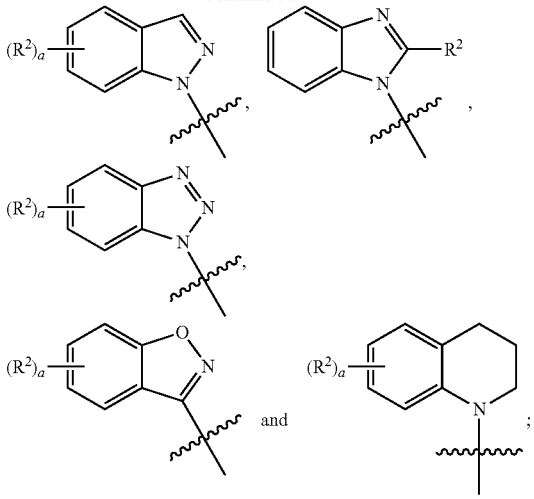

a is an integer from 0 to 2; and each $R^2$ is independently selected from the group consisting of halogen, $C_{1-2}$alkyl, $C_{1-2}$alkoxy, fluorinated $C_{1-2}$alkyl, and fluorinated $C_{1-2}$alkoxy.

In another embodiment, the present invention is directed to compound of formula (I) wherein $R^1$ is selected from the group consisting of

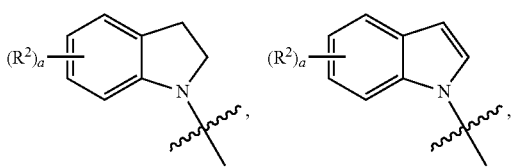

a is an integer from 0 to 2; and each $R^2$ is independently selected from the group consisting of halogen, $C_{1-2}$alkyl, $C_{1-2}$alkoxy and trifluoromethyl.

In another embodiment, the present invention is directed to compound of formula (I) wherein $R^1$ is selected from the group consisting of indol-1-yl, 6-fluoro-indol-1-yl, indolin-1-yl, 4-fluoro-indolin-1-yl, 5-fluoro-indolin-1-yl, 6-fluoro-indolin-1-yl, 4-chloro-indolin-1-yl, 5-chloro-indolin-1-yl, 6-chloro-indolin-1-yl, 4,6-dichloro-indolin-1-yl, 6-methyl-indolin-1-yl, 6-methoxy-indolin-1-yl, 6-trifluoromethyl-indolin-1-yl, 1H-indazol-1-yl, 4-fluoro-1H-indazol-1-yl, 5-fluoro-1H-indazol-1-yl, 6-fluoro-1H-indazol-1-yl, 3-chloro-1H-indazol-1-yl, 4-chloro-1H-indazol-1-yl, 6-chloro-1H-indazol-1-yl, 4-trifluoromethyl-1H-indazol-1-yl, 6-trifluoromethyl-1H-indazol-1-yl, 2-(trifluoromethyl)-1H-benzo[d]imidazol-1-yl, 1H-benzo[d][1,2,3]triazol-1-yl, 5-fluoro-benzo[d]isoxazol-3-yl, 6-fluoro-benzo[d]isoxazol-1-yl, and 1,2,3,4-tetrahydroquinolin-1-yl.

In another embodiment, the present invention is directed to compound of formula (I) wherein $R^1$ is selected from the group consisting of indol-1-yl, 6-fluoro-indolyl, indolin-1-yl, 6-fluoro-indolin-1-yl, 1H-indazol-1-yl, 4-fluoro-1H-indazol-1-yl, 6-fluoro-1H-indazol-1-yl, 3-chloro-1H-indazol-1-yl, 4-chloro-1H-indazol-1-yl, 6-chloro-1H-indazol-1-yl, 4-trifluoromethyl-1H-indazol-1-yl, 6-trifluoromethyl-1H-indazol-1-yl and 5-fluoro-benzo[d]isoxazol-3-yl. In another embodiment, the present invention is directed to compound of formula (I) wherein $R^1$ is selected from the group consisting of indol-1-yl, 6-fluoro-indolyl, indolin-1-yl, 6-fluoro-indolin-1-yl, 6-fluoro-1H-indazol-1-yl, 3-chloro-1H-indazol-1-yl, 4-chloro-1H-indazol-1-yl, 6-chloro-1H-indazol-1-yl, 6-trifluoromethyl-1H-indazol-1-yl and 5-fluoro-benzo[d]isoxazol-3-yl. In another embodiment, the present invention is directed to compound of formula (I) wherein $R^1$ is selected from the group consisting of indol-1-yl, indolin-1-yl, 6-fluoro-indolin-1-yl, 3-chloro-1H-indazol-1-yl, 4-chloro-1H-indazol-1-yl, 6-chloro-1H-indazol-1-yl, 6-trifluoromethyl-1H-indazol-1-yl and 5-fluoro-benzo[d]isoxazol-3-yl.

In another embodiment, the present invention is directed to compound of formula (I) wherein $R^1$ is selected from the group consisting of indol-1-yl, 6-fluoro-indol-1-yl, indolin-1-yl, 5-fluoro-indolin-1-yl, 6-fluoro-indolin-1-yl, 6-chloro-indolin-1-yl, 6-trifluoromethyl-indolin-1-yl, 1H-indazol-1-yl, 4-fluoro-1H-indazol-1-yl, 6-fluoro-1H-indazol-1-yl, 3-chloro-1H-indazol-1-yl, 4-chloro-1H-indazol-1-yl, 6-chloro-1H-indazol-1-yl and 5-fluoro-benzo[d]isoxazol-3-yl. In another embodiment, the present invention is directed to compound of formula (I) wherein R¹ is selected from the group consisting of 6-fluoro-indol-1-yl, indolin-1-yl, 6-fluoro-indolin-1-yl, 6-chloro-indolin-1-yl, 6-trifluoromethyl-indolin-1-yl, 1H-indazol-1-yl, 6-fluoro-1H-indazol-1-yl, 3-chloro-1H-indazol-1-yl, 4-chloro-1H-indazol-1-yl, 6-chloro-1H-indazol-1-yl and 5-fluoro-benzo[d]isoxazol-3-yl. In another embodiment, the present invention is directed to compound of formula (I) wherein R¹ is selected from the group consisting of 6-fluoro-indolin-1-yl, 6-fluoro-1H-indazol-1-yl, 3-chloro-1H-indazol-1-yl, 4-chloro-1H-indazol-1-yl and 5-fluoro-benzo[d]isoxazol-3-yl.

In another embodiment, the present invention is directed to compound of formula (I) wherein R¹ is selected from the group consisting of 6-fluoro-indolin-1-yl and 5-fluoro-benzo[d]isoxazol-3-yl.

In additional embodiments, the present invention is directed to compounds of formula (I) wherein R¹ is selected to be any one of the following optionally substituted, bicyclic ring structures:

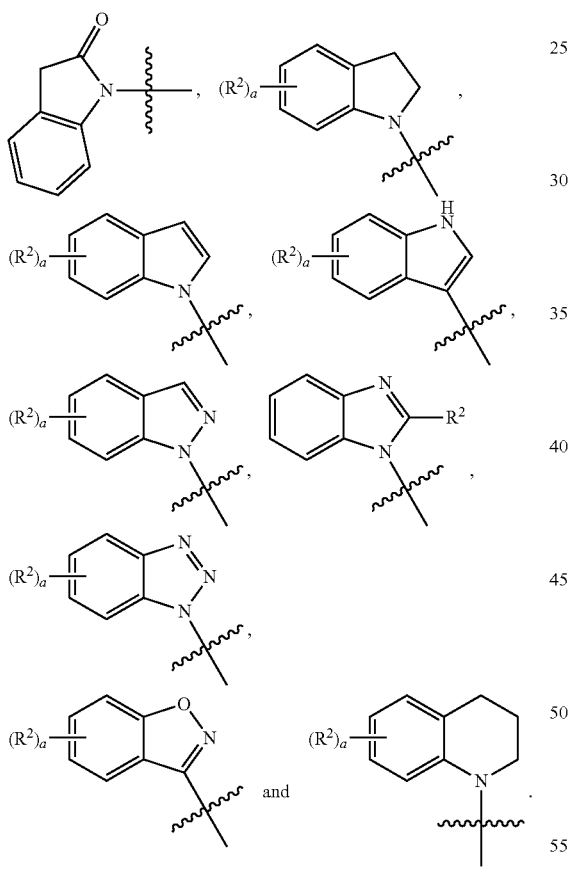

In an embodiment, the present invention is directed to compounds of formula (I) wherein, a is an integer from 0 to 2. In another embodiment, the present invention is directed to compound of formula (I) wherein, a is an integer from 0 to 1. In another embodiment, the present invention is directed to compound of formula (I) wherein, a is an integer from 1 to 2. In another In another embodiment, the present invention is directed to compound of formula (I) wherein a is 1.

In an embodiment, the present invention is directed to compounds of formula (I) wherein, each $R^2$ is independently selected from the group consisting of fluoro, chloro, methyl, methoxy and trifluoromethyl. In another embodiment, the present invention is directed to compounds of formula (I) wherein each $R^2$ is independently selected from the group consisting of fluoro, chloro and trifluoromethyl. In another embodiment, the present invention is directed to compounds of formula (I) wherein each $R^2$ is independently selected from the group consisting of fluoro and chloro. In another embodiment, the present invention is directed to compounds of formula (I) wherein each $R^2$ is fluoro.

In an embodiment, the present invention is directed to compounds of formula (I) wherein, $R^3$ is selected from the group consisting of

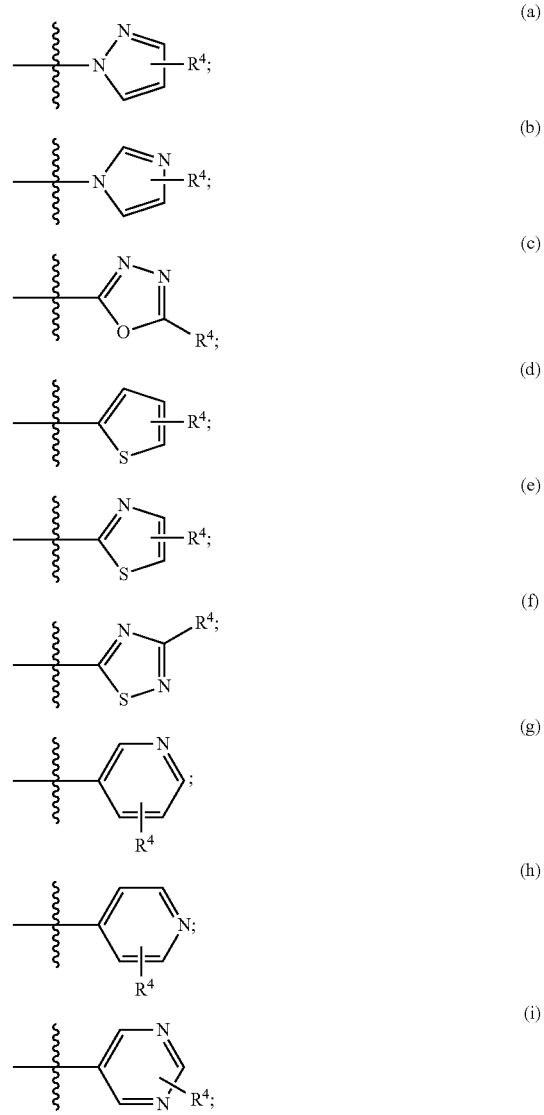

wherein $R^4$ is selected from the group consisting of hydrogen, halogen, $C_{1-4}$alkyl, fluorinated $C_{1-2}$alkyl, —$C_{1-2}$alkyl-OH, $C_{1-2}$alkoxy, fluorinated $C_{1-2}$alkoxy, —$C_{1-2}$alkyl-O—$C_{1-2}$alkyl, —$CO_2H$, —$C(O)O$—$C_{1-2}$alkyl, —$C_{1-2}$alkyl-OC(O)—$C_{1-2}$alkyl, —$NR^AR^B$, —$C_{1-2}$alkyl-$NR^AR^B$, —$C(O)$—$NR^AR^B$, —$C_{1-2}$alkyl-C(O)—$NR^AR^B$ and —$NR^A$—$C(O)$—$(C_{1-2}$alkyl);

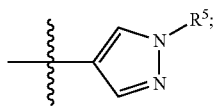
(j)

wherein $R^5$ is selected from the group consisting of hydrogen, $C_{1-4}$alkyl, —$C_{2-4}$alkyl-OH, —$C_{2-3}$alkyl-O—$C_{1-2}$alkyl, —$C_{1-2}$alkyl-C(O)O—$C_{1-2}$alkyl, —$C_{2-4}$alkyl-NR$^A$R$^B$ and —$C_{1-2}$alkyl-C(O)NR$^A$R$^B$;

and

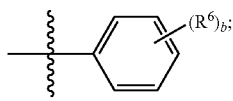
(k)

wherein b is an integer from 0 to 1; and wherein each $R^6$ is independently selected from the group consisting of halogen, $C_{1-4}$alkyl, fluorinated $C_{1-2}$alkyl, —$C_{1-2}$alkyl-OH, $C_{1-2}$alkoxy, fluorinated $C_{1-2}$alkoxy, —CO$_2$H, —C(O)O—$C_{1-4}$alkyl, —$C_{1-2}$alkyl-C(O)O—$C_{1-2}$alkyl, —C(O)—NR$^A$R$^B$, —$C_{1-2}$alkyl-C(O)—NR$^A$R$^B$, —NR$^A$R$^B$ and —$C_{1-2}$alkyl-NR$^A$R$^B$.

In another embodiment, the present invention is directed to compound of formula (I) wherein, $R^3$ is selected from the group consisting of

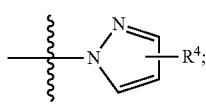
(a)

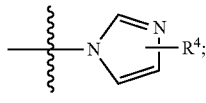
(b)

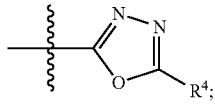
(c)

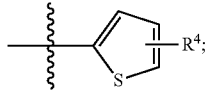
(d)

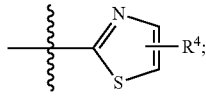
(e)

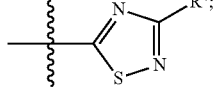
(f)

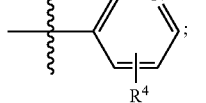
(g)

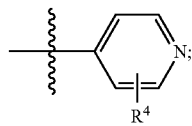
(h)

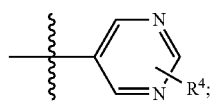
(i)

wherein $R^4$ is selected from the group consisting of hydrogen, halogen, $C_{1-2}$alkyl, trifluoromethyl, —$C_{1-2}$alkyl-OH, $C_{1-2}$alkoxy, —$C_{1-2}$alkyl-O—$C_{1-2}$alkyl, —$C_{1-2}$alkyl-OC(O)—$C_{1-2}$alkyl, —NR$^A$R$^B$, —$C_{1-2}$alkyl-NR$^A$R$^B$, —C(O)—NR$^A$R$^B$. and —NR$^A$—C(O)—($C_{1-2}$alkyl);

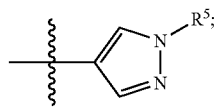
(j)

wherein $R^5$ is selected from the group consisting of hydrogen, $C_{1-3}$alkyl, —$C_{2}$alkyl-OH, —$C_{2-3}$alkyl-O—$C_{1-2}$alkyl, —$C_{1-2}$alkyl-C(O)O—$C_{1-2}$alkyl, —$C_{2-4}$alkyl-NR$^A$R$^B$ and —$C_{1-2}$alkyl-C(O)NR$^A$R$^B$;

and

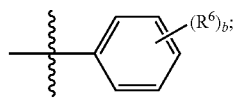
(k)

wherein b is 1; and wherein $R^6$ is selected from the group consisting of, halogen, $C_{1-2}$alkyl, trifluoromethyl, —$C_{1-2}$alkyl-OH, —CO$_2$H, —C(O)O—$C_{1-4}$alkyl and —C(O)—NR$^A$R$^B$.

In another embodiment, the present invention is directed to compound of formula (I) wherein, $R^3$ is selected from the group consisting of
(a) pyrazol-1-yl, 3-methyl-pyrazol-1-yl, 4-methyl-pyrazol-1-yl, 4-(hydroxymethyl)-pyrazol-1-yl, 4-(hydroxyethyl)-pyrazol-1-yl, 4-(methoxy-methyl)-pyrazol-1-yl, 4-(ethoxy-methyl)-pyrazol-1-yl, 4-(methylamino-methyl)-pyrazol-1-yl;
(b) imidazol-1-yl, 2-methyl-imidazol-1-yl, 4-methyl-imidazol-1-yl, 4-(hydroxymethyl)-imidazol-1-yl;
(c) 5-methyl-1,3,4-oxadiazol-2-yl, 5-(hydroxymethyl)-1,3,4-oxadiazol-2-yl, 5-(methylcarbonyl-oxy-methyl)-1,3,4-oxadiazol-2-yl;
(d) 4-methyl-thien-2-yl, 5-methyl-thien-2-yl;
(e) 4-methyl-thiazol-2-yl, 5-methyl-thiazol-2-yl;
(f) 3-methyl-1,2,4-thiadiazol-5-yl;
(g) pyrid-3-yl, 6-methyl-pyrid-3-yl, 6-methoxy-pyrid-3-yl, 6-(hydroxymethyl)-pyrid-3-yl, 6-(trifluoromethyl)-pyrid-3-yl, 6-(methylamino-carbonyl)-pyrid-3-yl, 6-(dimethylamino)-pyrid-3-yl, 6-(methylcarbonyl-amino)-pyrid-3-yl;
(h) 2-methyl-pyrid-4-yl;
(i) 2-methyl-pyrimidin-5-yl, 2-methoxy-pyrimidin-5-yl;

(j) 1H-pyrazol-4-yl, 1-methyl-pyrazol-4-yl, 1-ethyl-pyrazol-4-yl, 1-(n-propyl)-pyrazol-4-yl, 1-(hydroxyethyl)-pyrazol-4-yl, 1-(ethoxycarbonyl-methyl)-pyrazol-4-yl, 1-(aminocarbonyl-methyl)-pyrazol-4-yl, 1-(methylamino-carbonyl-methyl)-pyrazol-4-yl, 1-(morpholin-4-yl-ethyl)-pyrazol-4-yl, 1-(ethoxy-ethyl)-pyrazol-4-yl; and
(k) 4-fluoro-phenyl, 4-methyl-phenyl, 4-(hydroxymethyl)-phenyl, 4-(trifluoromethyl)-phenyl, 4-(tert-butoxycarbonyl)-phenyl, 4-(carboxy)-phenyl, 4-(aminocarbonyl)-phenyl.

In another embodiment, the present invention is directed to compound of formula (I) wherein, $R^3$ is selected from the group consisting of
(a) 4-methyl-pyrazol-1-yl, 4-(hydroxymethyl)-pyrazol-1-yl, 4-(hydroxyethyl)-pyrazol-1-yl, 4-(methoxy-methyl)-pyrazol-1-yl, 4-(ethoxy-methyl)-pyrazol-1-yl;
(b) 4-methyl-imidazol-1-yl, 4-(hydroxymethyl)-imidazol-1-yl;
(c) 5-(hydroxymethyl)-1,3,4-oxadiazol-2-yl;
(e) 4-methyl-thiazol-2-yl, 5-methyl-thiazol-2-yl;
(f) 3-methyl-1,2,4-thiadiazol-5-yl;
(g) 6-methyl-pyrid-3-yl, 6-methoxy-pyrid-3-yl, 6-(hydroxymethyl)-pyrid-3-yl, 6-(trifluoromethyl)-pyrid-3-yl, 6-(methylamino-carbonyl)-pyrid-3-yl, 6-(dimethylamino)-pyrid-3-yl, 6-(methylcarbonyl-amino)-pyrid-3-yl;
(i) 2-methoxy-pyrimidin-5-yl;
(j) 1H-pyrazol-4-yl, 1-methyl-pyrazol-4-yl, 1-ethyl-pyrazol-4-yl, 1-(n-propyl)-pyrazol-4-yl, 1-(hydroxyethyl)-pyrazol-4-yl, 1-(ethoxycarbonyl-methyl)-pyrazol-4-yl, 1-(methylamino-carbonyl-methyl)-pyrazol-4-yl, 1-(ethoxyethyl)-pyrazol-4-yl; and
(k) 4-methyl-phenyl, 4-(hydroxymethyl)-phenyl.

In another embodiment, the present invention is directed to compound of formula (I) wherein, $R^3$ is selected from the group consisting of
(a) 4-methyl-pyrazol-1-yl, 4-(hydroxymethyl)-pyrazol-1-yl, 4-(hydroxyethyl)-pyrazol-1-yl, 4-(methoxy-methyl)-pyrazol-1-yl, 4-(ethoxy-methyl)-pyrazol-1-yl;
(b) 4-methyl-imidazol-1-yl, 4-(hydroxymethyl)-imidazol-1-yl;
(c) 5-(hydroxymethyl)-1,3,4-oxadiazol-2-yl;
(e) 4-methyl-thiazol-2-yl, 5-methyl-thiazol-2-yl;
(f) 3-methyl-1,2,4-thiadiazol-5-yl;
(g) 6-methyl-pyrid-3-yl, 6-methoxy-pyrid-3-yl, 6-(hydroxymethyl)-pyrid-3-yl, 6-(trifluoromethyl)-pyrid-3-yl, 6-(methylamino-carbonyl)-pyrid-3-yl, 6-(dimethylamino)-pyrid-3-yl, 6-(methylcarbonyl-amino)-pyrid-3-yl;
(i) 2-methoxy-pyrimidin-5-yl;
(j) 1H-pyrazol-4-yl, 1-methyl-pyrazol-4-yl, 1-ethyl-pyrazol-4-yl, 1-(n-propyl)-pyrazol-4-yl, 1-(hydroxyethyl)-pyrazol-4-yl, 1-(ethoxycarbonyl-methyl)-pyrazol-4-yl, 1-(methylamino-carbonyl-methyl)-pyrazol-4-yl, 1-(ethoxyethyl) pyrazol-4-yl; and
(k) 4-(hydroxymethyl)-phenyl.

In another embodiment, the present invention is directed to compound of formula (I) wherein, $R^3$ is selected from the group consisting of
(a) 4-methyl-pyrazol-1-yl, 4-(hydroxymethyl)-pyrazol-1-yl, 4-(methoxy-methyl)pyrazol-1-yl, 4-(ethoxy-methyl)-pyrazol-1-yl;
(b) 4-methyl-imidazol-1-yl, 4-(hydroxymethyl)-imidazol-1-yl;
(c) 5-(hydroxymethyl)-1,3,4-oxadiazol-2-yl;
(e) 4-methyl-thiazol-2-yl, 5-methyl-thiazol-2-yl;
(f) 3-methyl-1,2,4-thiadiazol-5-yl;

(g) 6-methyl-pyrid-3-yl, 6-methoxy-pyrid-3-yl, 6-(hydroxymethyl)-pyrid-3-yl, 6-(trifluoromethyl)-pyrid-3-yl, 6-(dimethylamino)-pyrid-3-yl, 6-(methylcarbonyl-amino) pyrid-3-yl;
(i) 2-methoxy-pyrimidin-5-yl;
(j) 1-methyl-pyrazol-4-yl, 1-ethyl-pyrazol-4-yl, 1-(n-propyl)-pyrazol-4-yl, 1-(methylamino-carbonyl-methyl)-pyrazol-4-yl and 1-(ethoxy-ethyl)-pyrazol-4-yl.

In another embodiment, the present invention is directed to compound of formula (I) wherein, $R^3$ is selected from the group consisting of
(a) 3-methyl-pyrazol-1-yl, 4-methyl-pyrazol-1-yl, 4-(hydroxymethyl)-pyrazol-1-yl, 4-(hydroxyethyl)-pyrazol-1-yl, 4-(methoxy-methyl)-pyrazol-1-yl, 4-(ethoxy-methyl)-pyrazol-1-yl;
(b) 4-methyl-imidazol-1-yl, 4-(hydroxymethyl)-imidazol-1-yl;
(c) 5-(hydroxymethyl)-1,3,4-oxadiazol-2-yl;
(d) 4-methyl-thien-2-yl, 5-methyl-thien-2-yl;
(e) 4-methyl-thiazol-2-yl, 5-methyl-thiazol-2-yl;
(f) 3-methyl-1,2,4-thiadiazol-5-yl;
(g) 6-methyl-pyrid-3-yl, 6-methoxy-pyrid-3-yl, 6-(hydroxymethyl)-pyrid-3-yl, 6-(trifluoromethyl)-pyrid-3-yl, 6-(methylamino-carbonyl)-pyrid-3-yl, 6-(dimethylamino)-pyrid-3-yl, 6-(methylcarbonyl-amino)-pyrid-3-yl;
(h) 2-methyl-pyrid-4-yl;
(i) 2-methoxy-pyrimidin-5-yl;
(j) 1H-pyrazol-4-yl, 1-methyl-pyrazol-4-yl, 1-ethyl-pyrazol-4-yl, 1-(n-propyl)-pyrazol-4-yl, 1-(hydroxyethyl)-pyrazol-4-yl, 1-(ethoxycarbonyl-methyl)-pyrazol-4-yl, 1-(methylamino-carbonyl-methyl)-pyrazol-4-yl, 1-(ethoxyethyl)-pyrazol-4-yl; and
(k) 4-methyl-phenyl, 4-(hydroxymethyl)-phenyl, 4-(trifluoromethyl)-phenyl.

In another embodiment, the present invention is directed to compound of formula (I) wherein, $R^3$ is selected from the group consisting of
(a) 4-methyl-pyrazol-1-yl, 4-(hydroxymethyl)-pyrazol-1-yl, 4-(hydroxyethyl)-pyrazol-1-yl, 4-(methoxy-methyl)-pyrazol-1-yl, 4-(ethoxy-methyl)-pyrazol-1-yl;
(b) 4-(hydroxymethyl)-imidazol-1-yl;
(c) 5-(hydroxymethyl)-1,3,4-oxadiazol-2-yl;
(d) 4-methyl-thien-2-yl, 5-methyl-thien-2-yl;
(e) 4-methyl-thiazol-2-yl, 5-methyl-thiazol-2-yl;
(f) 3-methyl-1,2,4-thiadiazol-5-yl;
(g) 6-methyl-pyrid-3-yl, 6-methoxy-pyrid-3-yl, 6-(hydroxymethyl)-pyrid-3-yl, 6-(trifluoromethyl)-pyrid-3-yl, 6-(methylamino-carbonyl)-pyrid-3-yl, 6-(dimethylamino)-pyrid-3-yl, 6-(methylcarbonyl-amino)-pyrid-3-yl;
(h) 2-methyl-pyrid-4-yl;
(i) 2-methoxy-pyrimidin-5-yl;
(j) 1H-pyrazol-4-yl, 1-methyl-pyrazol-4-yl, 1-ethyl-pyrazol-4-yl, 1-(hydroxyethyl)-pyrazol-4-yl, 1-(ethoxycarbonyl-methyl)-pyrazol-4-yl, 1-(methylamino-carbonyl-methyl)-pyrazol-4-yl; and
(k) 4-methyl-phenyl, 4-(hydroxymethyl)-phenyl.

In another embodiment, the present invention is directed to compound of formula (I) wherein, $R^3$ is selected from the group consisting of
(a) 4-(hydroxymethyl)-pyrazol-1-yl, 4-(hydroxyethyl)-pyrazol-1-yl, 4-(ethoxy-methyl)-pyrazol-1-yl;
(b) 4-(hydroxymethyl)-imidazol-1-yl;
(c) 5-(hydroxymethyl)-1,3,4-oxadiazol-2-yl;
(d) 4-methyl-thien-2-yl, 5-methyl-thien-2-yl;
(e) 4-methyl-thiazol-2-yl, 5-methyl-thiazol-2-yl;

(g) 6-methyl-pyrid-3-yl, 6-methoxy-pyrid-3-yl, 6-(hydroxymethyl)-pyrid-3-yl, 6-(trifluoromethyl)-pyrid-3-yl, 6-(methylamino-carbonyl)-pyrid-3-yl;

(h) 2-methyl-pyrid-4-yl;

(i) 2-methoxy-pyrimidin-5-yl;

(j) 1-methyl-pyrazol-4-yl, 1-(hydroxyethyl)-pyrazol-4-yl, 1-(methylamino-carbonyl-methyl)-pyrazol-4-yl; and (k) 4-methyl-phenyl, 4-(hydroxymethyl)-phenyl.

In another embodiment, the present invention is directed to compound of formula (I) wherein, $R^3$ is selected from the group consisting of (a) 4-(ethoxymethyl)-pyrazol-1-yl; (e) 4-methyl-thiazol-2-yl; (i) 6-methyl-pyrid-3-yl, 6-methoxy-pyrid-3-yl, 6-(hydroxymethyl)-pyrid-3-yl; and (k) 1-methyl-pyrazol-3-yl).

In additional embodiments, the present invention is directed to compounds of formula (I) wherein $R^3$ is selected to be any one of the following optionally substituted, bicyclic ring structures:

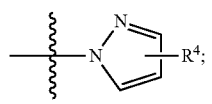
(a)

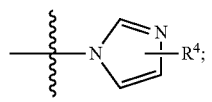
(b)

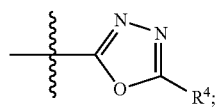
(c)

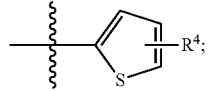
(d)

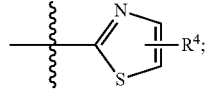
(e)

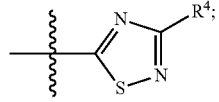
(f)

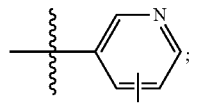
(g)

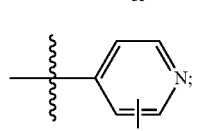
(h)

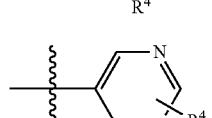
(i)

-continued

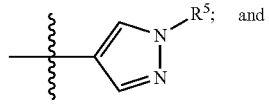
(j)

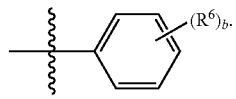
(k)

In an embodiment, the present invention is directed to compounds of formula (I) wherein, $R^4$ is selected from the group consisting of methyl, trifluoromethyl, hydroxymethyl-, hydroxyethyl-, methoxy, methoxy-methyl-, ethoxy-methyl-, methylcarbonyl-oxy-methyl-, dimethylamino-, methylamino-methyl-, methylamino-carbonyl- and methylcarbonyl-amino.

In another embodiment, the present invention is directed to compounds of formula (I) wherein $R^4$ is selected from the group consisting of methyl, trifluoromethyl, hydroxymethyl-, hydroxyethyl-, methoxy, methoxy-methyl-, ethoxy-methyl-, dimethylamino-, methylamino-carbonyl- and methylcarbonyl-amino. In another embodiment, the present invention is directed to compounds of formula (I) wherein $R^4$ is selected from the group consisting of methyl, trifluoromethyl, hydroxymethyl-, methoxy, methoxy-methyl-, ethoxy-methyl-, dimethylamino- and methylcarbonyl-amino. In another embodiment, the present invention is directed to compounds of formula (I) wherein $R^4$ is selected from the group consisting of methyl, trifluoromethyl, hydroxymethyl-, hydroxyethyl-, methoxy, ethoxy-methyl- and methylamino-carbonyl-. In another embodiment, the present invention is directed to compounds of formula (I) wherein $R^4$ is selected from the group consisting of methyl, hydroxymethyl-, methoxy and ethoxy-methyl-. In another embodiment, the present invention is directed to compounds of formula (I) wherein $R^4$ is selected from the group consisting of methyl and hydroxymethyl. In another embodiment, the present invention is directed to compounds of formula (I) wherein $R^4$ is methyl.

In an embodiment, the present invention is directed to compounds of formula (I) wherein, $R^5$ is selected from the group consisting of methyl, ethyl, n-propyl, hydroxyethyl-, ethoxycarbonyl-methyl-, aminocarbonyl-methyl-, methylamino-carbonyl-methyl-, morpholinyl-ethyl- and ethoxy-ethyl-.

In another embodiment, the present invention is directed to compounds of formula (I) wherein $R^5$ is selected from the group consisting of methyl, ethyl, n-propyl, hydroxyethyl-, ethoxycarbonyl-methyl-, methylamino-carbonyl-methyl- and ethoxy-ethyl-. In another embodiment, the present invention is directed to compounds of formula (I) wherein $R^5$ is selected from the group consisting of methyl, ethyl, n-propyl, methylamino-carbonyl-methyl- and ethoxy-ethyl-.

In another embodiment, the present invention is directed to compounds of formula (I) wherein $R^5$ is selected from the group consisting of methyl, ethyl, hydroxethyl-, ethoxycarbonyl-methyl- and methylaminocarbonyl-methyl-. In another embodiment, the present invention is directed to compounds of formula (I) wherein $R^5$ is selected from the group consisting of methyl, hydroxyethyl- and methylamino-carbonyl-methyl-. In another embodiment, the present invention is directed to compounds of formula (I) wherein $R^5$ is methyl.

In an embodiment, the present invention is directed to compounds of formula (I) wherein, b is an integer from 0 to 1. In another embodiment, the present invention is directed to compound of formula (I) wherein, b is an integer from 1 to 2. In another embodiment, the present invention is directed to compound of formula (I) wherein b is 1.

In an embodiment, the present invention is directed to compounds of formula (I) wherein, each $R^6$ is independently selected from the group consisting of fluoro, methyl, hydroxymethyl, trifluoromethyl, tert-butoxycarbonyl, carboxy and aminocarbonyl. In another embodiment, the present invention is directed to compounds of formula (I) wherein each $R^6$ is independently selected from the group consisting of methyl, hydroxymethyl and trifluoromethyl. In another embodiment, the present invention is directed to compounds of formula (I) wherein each $R^6$ is independently selected from the group consisting of methyl and hydroxymethyl. In another embodiment, the present invention is directed to compounds of formula (I) wherein $R^6$ is hydroxymethyl.

In an embodiment, the present invention is directed to compounds of formula (I) wherein, $R^A$ and $R^B$ are each independently selected from the group consisting of hydrogen and methyl.

In an embodiment, the present invention is directed to compounds of formula (I) wherein, $R^A$ and $R^B$ are taken together with the nitrogen atom to which they are bound to form piperidin-1-yl, piperazin-1-yl, morpholin-4-yl and pyrrolidin-1-yl. In another embodiment, the present invention is directed to compound of formula (I) wherein, $R^A$ and $R^B$ are taken together with the nitrogen atom to which they are bound to form piperidin-1-yl, piperazin-1-yl and morpholin-4-yl. In another embodiment, the present invention is directed to compound of formula (I) wherein, $R^A$ and $R^B$ are taken together with the nitrogen atom to which they are bound to form piperidin-1-yl. In another embodiment, the present invention is directed to compound of formula (I) wherein, $R^A$ and $R^B$ are taken together with the nitrogen atom to which they are bound to form pyrrolidin-1-yl.

In an embodiment, the present invention is directed to compounds of formula (I) wherein, when $R^1$ is indol-3-yl, then $R^3$ is other than

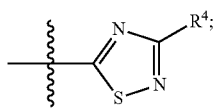

wherein $R^4$ is selected from the group consisting of hydrogen, $C_{1-4}$alkyl, —$C_{1-2}$alkyl-OH, $C_{1-4}$alkoxy and —$NR^AR^B$. In another embodiment, the present invention is directed to compounds of formula (I) wherein, when $R^1$ is

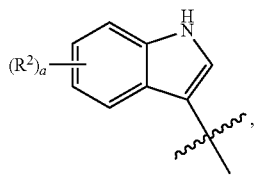

then $R^3$ is other than

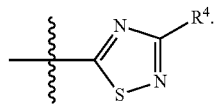

In another embodiment, the present invention is directed to compounds of formula (I) wherein $R^1$ is other than

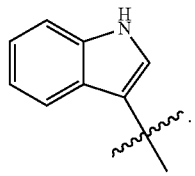 [SMILES: *c1c[nH]c2ccccc12]

In another embodiment, the present invention is directed to compounds of formula (I) wherein $R^1$ is other than

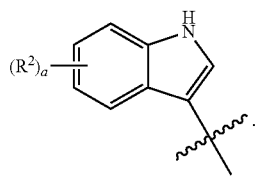

In another embodiment, the present invention is directed to compounds of formula (I) wherein $R^3$ is other than

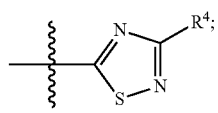

wherein $R^4$ is $C_{1-4}$alkyl. In another embodiment, the present invention is directed to compounds of formula (I) wherein $R^3$ is other than

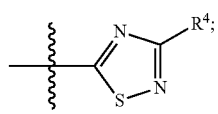

wherein $R^4$ is selected from the group consisting of hydrogen, $C_{1-4}$alkyl, —$C_{1-2}$alkyl-OH, $C_{1-4}$alkoxy and —$NR^AR^B$. In another embodiment, the present invention is directed to compounds of formula (I) wherein $R^3$ is other than

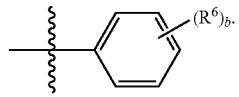

Additional embodiments of the present invention, include those wherein the substituents selected for one or more of the variables defined herein (i.e. $R^1$, $R^2$, $R^3$, $R^4$, $R^5$, $R^6$, a, and b) are independently selected to be any individual substituent or any subset of substituents selected from the complete list as defined herein.

In another embodiment of the present invention is any single compound or subset of compounds selected from the representative compounds listed in Table 1, below. Representative compounds of the present invention are as listed in Table 1, below. Unless otherwise noted, wherein a stereogenic center is present in the listed compound, the compound was prepared as a mixture of stereo-configurations. Where a stereogenic center is present, the S*- and R* designations are intended to indicate that the exact stereo-configuration of the center has not been determined.

TABLE 1

Representative Compounds of Formula (I)

| ID No. | R¹ | R³ |
|---|---|---|
| 1 | indolin-1-yl | 4-methyl-imidazol-1-yl |
| 3 | 5-fluoro-benzo[d]isoxazol-3-yl | 1-methyl-pyrazol-4-yl |
| 4 | 6-fluoro-indolin-1-yl | 4-methyl-imidazol-1-yl |
| 5 | 5-fluoro-benzo[d]isoxazol-3-yl | 3-methyl-1,2,4-thiadiazol-5-yl |
| 6 | indol-1-yl | 3-methyl-1,2,4-thiadiazol-5-yl |
| 7 | indolin-1-yl | 3-methyl-1,2,4-thiadiazol-5-yl |
| 8 | 5-fluoro-benzo[d]isoxazol-3-yl | pyrid-3-yl |
| 9 | indol-1-yl | 1-methyl-pyrazol-4-yl |
| 10 | indolin-1-yl | 1-methyl-pyrazol-4-yl |
| 11 | 6-fluoro-indolin-1-yl | 1-methyl-pyrazol-4-yl |
| 12 | 6-fluoro-indolin-1-yl | 3-methyl-1,2,4-thiadiazol-5-yl |
| 13 | 5-fluoro-benzo[d]isoxazol-3-yl | 1-ethyl-pyrazol-4-yl |
| 15 | 6-fluoro-indolin-1-yl | 4-(hydroxymethyl)-imidazol-1-yl |
| 16 | 6-fluoro-indolin-1-yl | 4-methyl-imidazol-1-yl |
| 18 | 5-fluoro-benzo[d]isoxazol-3-yl | 5-methyl-1,3,4-oxadiazol-2-yl |
| 19 | 5-fluoro-benzo[d]isoxazol-3-yl | 5-(methylcarbonyl-oxy-methyl)-1,3,4-oxadiazol-2-yl |
| 20 | 5-fluoro-benzo[d]isoxazol-3-yl | 5-(hydroxymethyl)-1,3,4-oxadiazol-2-yl |
| 21 | 6-fluoro-indolin-1-yl | 1-ethyl-pyrazol-4-yl |
| 22 | 6-fluoro-indolin-1-yl | 4-(hydroxymethyl)-pyrazol-1-yl |
| 23 | 5-fluoro-benzo[d]isoxazol-3-yl | 4-methyl-thiazol-2-yl |
| 24 | 5-fluoro-benzo[d]isoxazol-3-yl | 6-methyl-pyrid-3-yl |
| 25 | 5-fluoro-benzo[d]isoxazol-3-yl | 2-methyl-pyrid-4-yl |
| 26 | 5-fluoro-benzo[d]isoxazol-3-yl | 1H-pyrazol-4-yl |
| 27 | 5-fluoro-benzo[d]isoxazol-3-yl | 4-methyl-thien-2-yl |
| 28 | 5-fluoro-benzo[d]isoxazol-3-yl | 5-methyl-thiazol-2-yl |
| 29 | 6-fluoro-indolin-1-yl | 4-methyl-thiazol-2-yl |
| 30 | 6-fluoro-indolin-1-yl | 6-methyl-pyrid-3-yl |
| 31 | 6-fluoro-indolin-1-yl | 5-methyl-thiazol-2-yl |
| 32 | 5-fluoro-benzo[d]isoxazol-3-yl | 4-methyl-phenyl |
| 33 | 5-fluoro-benzo[d]isoxazol-3-yl | 6-methoxy-pyrid-3-yl |
| 34 | 5-fluoro-benzo[d]isoxazol-3-yl | 2-methoxy-pyrimidin-5-yl |
| 35 | 5-fluoro-benzo[d]isoxazol-3-yl | 6-(hydroxymethyl)-pyrid-3-yl |
| 36 | 6-fluoro-indolin-1-yl | 4-methyl-phenyl |
| 37 | 6-fluoro-indolin-1-yl | 6-methoxy-pyrid-3-yl |
| 38 | 6-fluoro-indolin-1-yl | 2-methoxy-pyrimidin-5-yl |
| 39 | 6-fluoro-indolin-1-yl | 6-(hydroxymethyl)-pyrid-3-yl |
| 40 | 1H-indazol-1-yl | 1-methyl-pyrazol-4-yl |
| 41 | 2-(trifluoromethyl)-1H-benzo[d]imidazol-1-yl | 1-methyl-pyrazol-4-yl |
| 42 | 6-fluoro-indolin-1-yl | 6-(methylamino)-pyrazol-3-yl |
| 43 | 6-fluoro-indolin-1-yl | 4-(hydroxyehtyl)-pyrazol-1-yl |
| 44 | 6-fluoro-indolin-1-yl | 6-(dimethylamino)-pyrid-3-yl |
| 45 | 6-fluoro-indolin-1-yl | 6-(methylcarbonyl-amino)-pyrid-3-yl |
| 46 | 6-fluoro-indolin-1-yl | 1-methyl-pyrazol-4-yl |
| 47 | 6-fluoro-1H-indolin-1-yl | 1-methyl-pyrazol-4-yl |
| 48 | 1H-benzo[d][1,2,3]-triazol-1-yl | 1-methyl-pyrazol-4-yl |
| 49 | 6-fluoro-indolin-1-yl | 1-(hydroxyethyl)-pyrazol 4-yl |
| 50 | 6-fluoro-indolin-1-yl | 1-(ethoxycarbonyl-methyl)-pyrazol-4-yl |
| 51 | 6-fluoro-indolin-1-yl | 4-(hydroxymethyl)-phenyl |
| 52 | 6-fluoro-indolin-1-yl | 5-methyl-thien-2-yl |
| 53 | 6-fluoro-indolin-1-yl | 4-fluoro-phenyl |
| 54 | 6-fluoro-indolin-1-yl | 4-(trifluoromethyl)-phenyl |
| 55 | 6-fluoro-indolin-1-yl | 4-(tert-butoxy-carbonyl)-phenyl |
| 56 | 6-fluoro-indolin-1-yl | 4-(aminocarbonyl)-phenyl |
| 57 | 6-methyl-indolin-1-yl | 1-methyl-pyrazol-4-yl |
| 58 | 6-fluoro-indolin-1-yl | 4-(carboxy)-phenyl |
| 59 | 6-chloro-indolin-1-yl | 1-methyl-pyrazol-4-yl |
| 60 | 6-trifluoromethyl-indolin-1-yl | 1-methyl-pyrazol-4-yl |
| 61 | 4-chloro-1H-indazol-1-yl | 1-methyl-pyrazol-4-yl |
| 62 | 6-methoxy-indolin-1-yl | 1-methyl-pyrazol-4-yl |
| 63 | 6-fluoro-indolin-1-yl | 1-methyl-pyrazol-4-yl |
| 64 | 6-fluoro-indolin-1-yl | 1-(methylamino-carbonyl-methyl)-pyrazol-4-yl |
| 65 | 5-chloro-indolin-1-yl | 1-methyl-pyrazol-4-yl |
| 66 | 4-fluoro-indolin-1-yl | 1-methyl-pyrazol-4-yl |
| 67 | 4-chloro-indolin-1-yl | 1-methyl-pyrazol-4-yl |
| 68 | 4,6-dichloro-indolin-1-yl | 1-methyl-pyrazol-4-yl |
| 69 | 6-fluoro-indolin-1-yl | 1-(aminocarbonyl-methyl)-pyrazol-4-yl |
| 70 | 4-fluoro-1H-indolin-1-yl | 1-methyl-pyrazol-4-yl |
| 71 | 6-fluoro-indolin-1-yl | 1-(morpholin-4-yl-ethyl)-pyrazol-4-yl |
| 72 | 6-fluoro-indolin-1-yl | 4-(ethoxy-ethyl)-pyrazol-1-yl |
| 73 | 5-fluoro-1H-indazol-1-yl | 1-methyl-pyrazol-4-yl |
| 74 | 6-chloro-1H-indazol-1-yl | 1-methyl-pyrazol-4-yl |
| 75 | 5-fluoro-benzo[d]isoxazol-3-yl | 1-(ethoxy-ethyl)-pyrazol-4-yl |
| 76 | 6-fluoro-indolin-1-yl | 6-(trifluoromethyl)-pyrid-3-yl |
| 77 | 6-fluoro-indolin-1-yl | 1H-pyrazol-4-yl |
| 78 | 6-fluoro-indolin-1-yl | 1-(ethoxy-ethyl)-pyrazol-4-yl |
| 79 | 6-fluoro-indolin-1-yl | 1-(n-propyl)-pyrazol-4-yl |
| 80 | 4-trifluoromethyl-1H-indazol-1-yl | 1-methyl-pyrazol-4-yl |
| 81 | 6-trifluoromethyl-1H-indazol-1-yl | 1-methyl-pyrazol-4-yl |
| 82 | 6-fluoro-1H-indazol-1-yl | 1-(hydroxyethyl)-pyrazol-4-yl |
| 83 | 3-chloro-1H-indazol-1-yl | 1-methyl-pyrazol-4-yl |
| 84 | 5-fluoro-benzo[d]isoxazol-3-yl | imidazol-1-yl |
| 85 | 5-fluoro-benzo[d]isoxazol-3-yl | 4-methyl-imidazol-1-yl |
| 87 | 5-fluoro-benzo[d]isoxazol-3-yl | pyrazol-1-yl |
| 88 | indol-1-yl | 4-methyl-imidazol-1-yl |
| 89 | 6-fluoro-benzo[d]isoxazol-3-yl | 4-methyl-imidazol-1-yl |
| 90 | 1,2,3,4-tetrahydroquinolin-1-yl | 4-methyl-imidazol-1-yl |
| 91 | 5-fluoro-benzo[d]isoxazol-3-yl | 4-(hydroxymethyl)-imidazol-1-yl |
| 92 | 5-fluoro-benzo[d]isoxazol-3-yl | 3-methyl-pyrazol-1-yl |
| 93 | 5-fluoro-benzo[d]isoxazol-3-yl | 2-methyl-imidazol-1-yl |
| 94 | 5-fluoro-benzo[d]isoxazol-3-yl | 4-methyl-pyrazol-1-yl |
| 95 | 5-fluoro-benzo[d]isoxazol-3-yl | 4-(hydroxymethyl)-pyrazol-1-yl |
| 96 | 5-fluoro-benzo[d]isoxazol-3-yl | 4-(methoxy-methyl)-pyrazol-1-yl |
| 97 | 5-fluoro-benzo[d]isoxazol-3-yl | 4-(methylamino-methyl)-pyrazol-1-yl |
| 98 | 5-fluoro-benzo[d]isoxazol-3-yl | 4-(hydroxyethyl)-pyrazol-1-yl |

Table 2 below, lists representative intermediates in the synthesis of the compounds of formula (I) of the present invention.

TABLE 2

Intermediates in Synthesis of Compounds of Formula (I)

| ID No | R¹ | R⁰ |
|---|---|---|
| I1 | 5-fluoro-benzo[d]isoxazol-3-yl | —C(O)—NH—NH₂ |
| I2 | 5-fluoro-benzo[d]isoxazol-3-yl | —C(O)—NH—NH—C(O)—CH₃ |

As used herein, "halogen" shall mean chlorine, bromine, fluorine and iodine.

As used herein, the term "alkyl" whether used alone or as part of a substituent group, include straight and branched chains. For example, alkyl radicals include methyl, ethyl, n-propyl, isopropyl, n-butyl, isobutyl, sec-butyl, tert-butyl, pentyl and the like. Similarly, the term "$C_{X-Y}$alkyl", wherein X and Y are each integers shall include straight and branched chains containing between X and Y carbon atoms. For example, "$C_{1-4}$alkyl" shall mean straight and branched chains between 1 and 4 carbon atoms and include methyl, ethyl, propyl, isopropyl, butyl, isobutyl, sec-butyl and t-butyl. One skilled in the art will recognize that the term "—($C_{1-4}$alkyl)-" shall denote any $C_{1-4}$alkyl carbon chain as herein defined, wherein said $C_{1-4}$alkyl chain is divalent and is further bound through two points of attachment, preferably through two terminal carbon atoms.

As used herein, unless otherwise noted, the term "halogenated $C_{1-4}$alkyl" shall mean any $C_{1-4}$alkyl group as defined above substituted with at least one halogen atom, preferably substituted with a least one fluoro atom. Suitable examples include but are not limited to —CH₂F, —CF₃, —CH₂Cl, —CCl₃, —CH₂—CF₃, —CH₂—CCl₃, —CF₂—CF₂—CF₂—CF₃, and the like. Similarly, the term "fluorinated $C_{1-4}$alkyl" shall mean any $C_{1-4}$alkyl group as defined above substituted with at least one fluoro atom. Suitable examples include but are not limited to —CH₂F, —CHF₂, —CF₃, —CH₂—CF₃, —CF₂—CF₂—CF₂—CF₃, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like. Similarly, the term "$C_{X-Y}$alkoxy", wherein X and Y are each integers shall include oxygen ether radicals of straight or branched chain alkyl groups containing between X and Y carbon atoms. For example, "$C_{1-4}$alkoxy" shall mean straight and branched chains between 1 and 4 carbon atoms and include methoxy, ethoxy, n-propoxy, isopropoxy, n-butoxy, isobutoxy, sec-butoxy and tert-butoxy.

When a particular group is "substituted", that group may have one or more substituents, preferably from one to five substituents, more preferably from one to three substituents, most preferably from one to two substituents, independently selected from the list of substituents. With reference to substituents, the term "independently" means that when more than one of such substituents is possible, such substituents may be the same or different from each other.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenyl$C_1$-$C_6$alkylaminocarbonyl$C_1$-$C_6$alkyl" substituent refers to a group of the formula

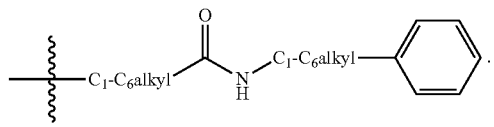

Abbreviations used in the specification, particularly the Schemes and Examples, are as follows:

| | | |
|---|---|---|
| aq. | = | Aqueous |
| ATP | = | Adenosine Triphosphate |
| Boc or tert-Boc | = | Tert-Butoxycarbonyl |
| BSA | = | Bovine Serum Albumin |
| CBz | = | Carboxybenzyl (i.e. —C(O)—CH₂-phenyl) |
| CoA | = | Coenzyme-A |
| DCE | = | Dichloroethane |
| DCM | = | Dichloromethane |
| DDQ | = | 2,3-dichloro-5,6-dicyanobenzoquinone |
| DIPEA or DIEA or (i-Pr)₂Net | = | Diisopropylethylamine |
| DMEM | = | Dulbecco's Modified Eagle Medium |
| DMF | = | N,N-Dimethylformamide |
| DMSO | = | Dimethylsulfoxide |
| EDTA | = | Ethylene Diamine Tetraacetic Acid |
| Et₃N | = | Triethylamine |
| Et₂O | = | Diethyl ether |
| EtOAc | = | Ethyl acetate |
| EtOH | = | Ethanol |
| FBS | = | Fetal Bovine Serum |
| HBSS | = | Hanks' Buffered Salt Solution |
| HPLC | = | High Pressure Liquid Chromatography |
| HPMC | = | Hydroxypropyl Methylcellulose |
| LiHMDS | = | Lithium bis(trimethylsilyl)amide |
| MeOH | = | Methanol |
| Mesyl | = | Methylsulfonyl |
| NaBH(OAc)₃ | = | Sodium triacetoxyborohydride |
| β-NADH | = | beta-Nicotinamide-Adenine Dinucleotide |

| | | |
|---|---|---|
| | | (reduced) |
| NaHMDS | = | Sodium bis(trimethylsilyl)amide |
| NASH | = | Non-Alcoholic Steatohepatitis |
| PBS | = | Phosphate Buffered Saline |
| $Pd_2(dppf)Cl_2$ | = | 1,1'-Bis(diphenylphosphino)ferrocene-palladium(II)dichloride |
| $Pd(PPh_3)_4$ | = | Tetrakistriphenylphosphine palladium (0) |
| $Pd(PPh_3)_2Cl_2$ | = | Bis(triphenylphosphine)palladium (II) chloride |
| RLM | = | Rat Liver Microsomes |
| SCD1 | = | Stearoyl-CoA Desaturase 1 |
| $Sn(n\text{-butyl})_3$ | = | Tri(n-butyl) Tin |
| TEA | = | Triethylamine |
| TFA | = | Trifluoroacetic Acid |
| THF | = | Tetrahydrofuran |
| TLC | = | Thin Layer Chromatography |
| TMSI | = | Iodotrimethylsilane |
| Tosyl | = | p-Toluenesulfonyl |
| Tris HCl or Tris-Cl | = | Tris[hydroxymethyl]aminomethyl hydrochloride |
| p-TSA | = | para-Toluene Sulfonic Acid |

As used herein, unless otherwise noted, the term "isolated form" shall mean that the compound is present in a form which is separate from any solid mixture with another compound(s), solvent system or biological environment. In an embodiment of the present invention, the compound of formula (I) is present in an isolated form.

As used herein, unless otherwise noted, the term "substantially pure form" shall mean that the mole percent of impurities in the isolated compound is less than about 5 mole percent, preferably less than about 2 mole percent, more preferably, less than about 0.5 mole percent, most preferably, less than about 0.1 mole percent. In an embodiment of the present invention, the compound of formula (I) is present as a substantially pure form.

As used herein, unless otherwise noted, the term "substantially free of a corresponding salt form(s)" when used to described the compound of formula (I) shall mean that mole percent of the corresponding salt form(s) in the isolated base of formula (I) is less than about 5 mole percent, preferably less than about 2 mole percent, more preferably, less than about 0.5 mole percent, most preferably less than about 0.1 mole percent. In an embodiment of the present invention, the compound of formula (I) is present in a form which is substantially free of corresponding salt form(s).

As used herein, unless otherwise noted, the term "SCD1 disorder" shall include obesity, type-II diabetes, Syndrome X (also known as metabolic syndrome), hypertriglyceridemia, dyslipidemia, NASH (Non-Alcoholic Steatohepatitis), hypercholesterolemia, hyperlipidemia, mixed dyslipidemia, fatty liver, nonalcoholic fatty liver disease and liver fibrosis. Preferably, the SCD1 disorders is obesity or type-II diabetes, more preferably type-II diabetes.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

As more extensively provided in this written description, terms such as "reacting" and "reacted" are used herein in reference to a chemical entity that is any one of: (a) the actually recited form of such chemical entity, and (b) any of the forms of such chemical entity in the medium in which the compound is being considered when named.

One skilled in the art will recognize that, where not otherwise specified, the reaction step(s) is performed under suitable conditions, according to known methods, to provide the desired product. One skilled in the art will further recognize that, in the specification and claims as presented herein, wherein a reagent or reagent class/type (e.g. base, solvent, etc.) is recited in more than one step of a process, the individual reagents are independently selected for each reaction step and may be the same of different from each other. For example wherein two steps of a process recite an organic or inorganic base as a reagent, the organic or inorganic base selected for the first step may be the same or different than the organic or inorganic base of the second step. Further, one skilled in the art will recognize that wherein a reaction step of the present invention may be carried out in a variety of solvents or solvent systems, said reaction step may also be carried out in a mixture of the suitable solvents or solvent systems. One skilled in the art will further recognize that wherein two consecutive reaction or process steps are run without isolation of the intermediate product (i.e. the product of the first of the two consecutive reaction or process steps), then the first and second reaction or process steps may be run in the same solvent or solvent system; or alternatively may be run in different solvents or solvent systems following solvent exchange, which may be completed according to known methods.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Examples of suitable solvents, bases, reaction temperatures, and other reaction parameters and components are provided in the detailed descriptions which follows herein. One skilled in the art will recognize that the listing of said examples is not intended, and should not be construed, as limiting in any way the invention set forth in the claims which follow thereafter. One skilled in the art will further recognize that wherein a reaction step of the present invention may be carried out in a variety of solvents or solvent systems, said reaction step may also be carried out in a mixture of the suitable solvents or solvent systems.

As used herein, unless otherwise noted, the term "leaving group" shall mean a charged or uncharged atom or group which departs during a substitution or displacement reaction. Suitable examples include, but are not limited to, Br, Cl, I, mesylate, tosylate, and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T.W. Greene & P.G.M. Wuts, *Protective Groups in Organic Synthesis*, John Wiley & Sons, 1991. The protecting groups may be removed at a convenient subsequent stage using methods known from the art.

As used herein, unless otherwise noted, the term "nitrogen protecting group" shall mean a group which may be attached to a nitrogen atom to protect said nitrogen atom from participating in a reaction and which may be readily removed following the reaction. Suitable nitrogen protecting groups include, but are not limited to carbamates—groups of the formula —C(O)O—R wherein R is for example methyl, ethyl, t-butyl, benzyl, phenylethyl, $CH_2=CH-CH_2-$, and the like; amides—groups of the formula —C(O)—R' wherein R' is for example methyl, phenyl, trifluoromethyl, and the like; N-sulfonyl derivatives—groups of the formula —$SO_2$—R" wherein R" is for example tolyl, phenyl, trifluoromethyl, 2,2,5,7,8-pentamethylchroman-6-yl-, 2,3,6-trimethyl-4-methoxybenzene, and the like. Other suitable nitrogen protecting groups may be found in texts such as T.W. Greene & P.G.M. Wuts, *Protective Groups in Organic Synthesis*, John Wiley & Sons, 1991.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows $$[(Rmoles-Smoles)/(Rmoles+Smoles)] \times 100\%$$

where Rmoles and Smoles are the R and S mole fractions in The resulting mixture such that Rmoles+Smoles=1. The enantiomeric excess may alternatively be calculated from the specific rotations of the desired enantiomer and the prepared mixture as follows:

$$ee=([\alpha\text{-}obs]/[\alpha\text{-max}]) \times 100.$$

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include, but are not limited to, the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids which may be used in the preparation of pharmaceutically acceptable salts include, but are not limited to, the following: acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid.

Representative bases which may be used in the preparation of pharmaceutically acceptable salts include, but are not limited to, the following: bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

General Synthetic Methods

Compounds of formula (I) may be prepared according to the process outlined in Scheme 1, below.

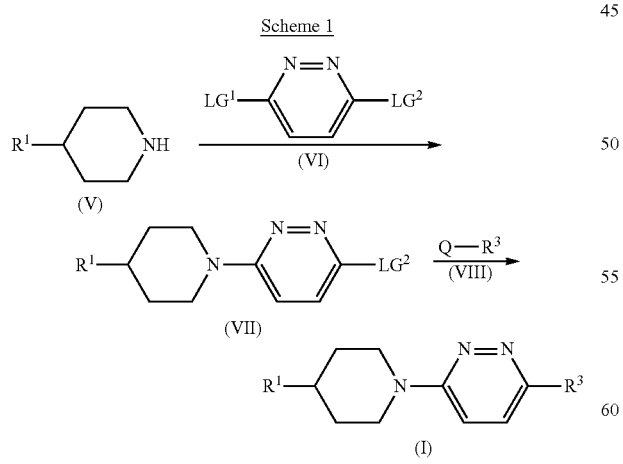

Accordingly, a suitably substituted compound of formula (V), a known compound or compound prepared by known methods, is reacted with a suitably substituted compound of formula (VI), wherein $LG^1$ and $LG^2$ are suitably selected leaving groups, such as chloro, bromo, iodo, and the like, preferably chloro, preferably $LG^1$ and $LG^2$ are the same, and are each chloro (i.e. 3,6-dichloropyradizine, a known compound); in the presence of a suitably selected organic base such as TEA, DIPEA, pyridine, and the like; in a suitably selected organic solvent such as DMSO, DMF, acetonitrile, and the like; under microwave heating or under thermal heating to about 200° C.; to yield the corresponding compound of formula (VII).

The compound of formula (VII) is reacted with a suitably selected compound of formula (VIII), wherein Q is

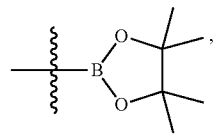 [SMILES: *B1OC(C)(C)C(C)(C)O1]

—$B(OH)_2$, or —$Sn(n\text{-butyl})_3$, a known compound or compound prepared by known methods; to yield the corresponding compound of formula (I).

Wherein the compound of formula (VIII), Q is

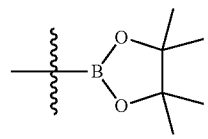 [SMILES: *B1OC(C)(C)C(C)(C)O1]

or —$B(OH)_2$, the compound of formula (VII) is reacted with the compound of formula (VIII) under Suzuki coupling conditions, more particularly in the presence of a suitably selected palladium catalyst such as $Pd(PPh_3)_4$, $Pd(PPh_3)_2Cl_2$, $Pd(dppf)Cl_2$, and the like; in the presence of a suitably selected base such as $K_2CO_3$, $Cs_2CO_3$, $Na_2CO_3$, $NaOH_{(aq)}$, and the like; in a suitably selected solvent such as aqueous 1,4-dioxane, ethanol, toluene, and the like.

Similarly, wherein the compound of formula (VIII), Q is —$Sn(n\text{-butyl})_3$, the compound of formula (VII) is reacted with the compound of formula (VIII) under Stille coupling conditions, more particularly in the presence of a suitably selected palladium catalyst such as $Pd(PPh_3)_4$, $Pd(PPh_3)_2Cl_2$, $Pd(dppf)Cl_2$, and the like; in a suitably selected solvent such as aqueous 1,4-dioxane, ethanol, DMF, toluene, and the like; under microwave heating.

Compounds of formula (I) wherein $R^1$ is selected from the group consisting of

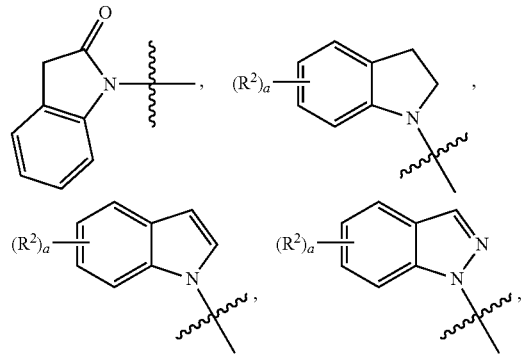

-continued

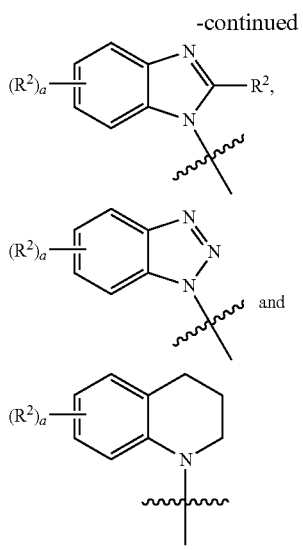

may alternatively be prepared according to the process outlined in Scheme 2, below.

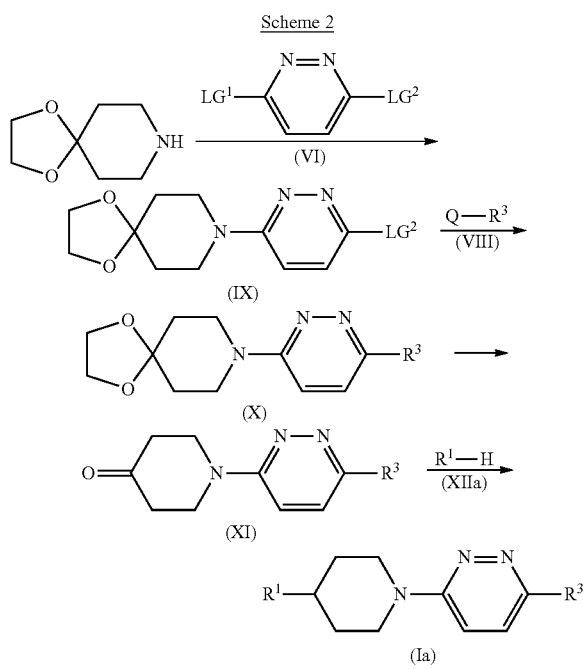

Accordingly, 1,4-dioxa-8-azaspiro[4.5]decane, a known compound or compound prepared by known methods, is reacted with a suitably substituted compound of formula (VI), wherein $LG^1$ and $LG^2$ are suitably selected leaving groups, such as chloro, bromo, iodo, and the like, preferably chloro, preferably $LG^1$ and $LG^2$ are the same, and are each chloro (i.e. 3,6-dichloropyradizine, a known compound); in the presence of a suitably selected organic base such as DIPEA, TEA, pyridine, and the like; in a suitably selected organic solvent such as DMSO, DMF, and the like; to yield the corresponding compound of formula (IX).

The compound of formula (IX) is reacted with a suitably substituted compound of formula (VIII), wherein Q is

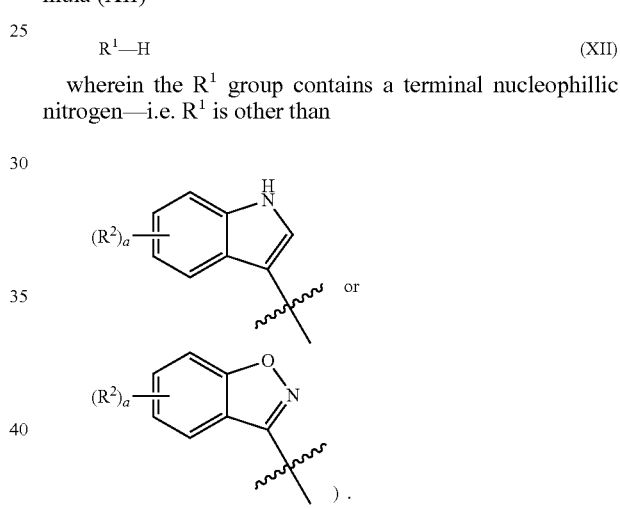

or —B(OH$_2$), a known compound or compound prepared by known methods; under Suzuki coupling conditions, more particularly in the presence of a suitably selected palladium catalyst such as Pd(PPh$_3$)$_4$, Pd(PPh$_3$)$_2$Cl$_2$, Pd(dppf)Cl$_2$, and the like; in the presence of a suitably selected base such as K$_2$CO$_3$, Cs$_2$CO$_3$, Na$_2$CO$_3$, NaOH$_{(aq)}$, and the like; in a suitably selected solvent such as aqueous 1,4-dioxane, ethanol, toluene, and the like; to yield the corresponding compound of formula (X).

The compound of formula (X) is reacted with a suitably selected acid such as p-TSA, HCl, and the like; in a suitably selected solvent such as aqueous acetone, 2-butanone, and the like; to yield the corresponding compound of formula (XI).

The compound of formula (XI) is reacted with a suitably selected compound of formula (XIIa) (a compound of formula (XII)

$$R^1\text{—H} \qquad (XII)$$

wherein the $R^1$ group contains a terminal nucleophillic nitrogen—i.e. $R^1$ is other than

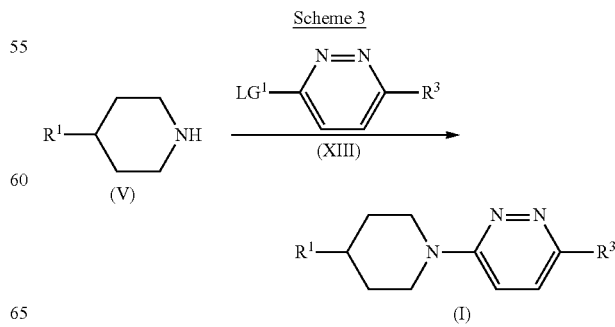

a known compound or compound prepared by known methods; in the presence of a suitably selected reducing agent such as NaBH(OAc)$_3$, NaBH$_3$CN, and the like; in a suitably selected organic solvent such as DCM, DCE, THF, and the like; to yield the corresponding compound of formula (Ia).

Compounds of formula (I) may alternatively be prepared according to the process outlined in Scheme 3, below.

Accordingly, a suitably substituted compound of formula (V), a known compound or compound prepared by known methods, is reacted with a suitably substituted compound of formula (XIII), wherein LG1 is a suitably selected leaving group, such as chloro, bromo, iodo, and the like, preferably chloro, a known compound or compound prepared by known methods; in the presence of a suitably selected organic base such as TEA, DIPEA, pyridine, and the like; in a suitably selected organic solvent such as DMSO, DMF, acetonitrile, and the like; under microwave heating or under thermal heating to about 200° C.; to yield the corresponding compound of formula (I).

Compounds of formula (I) wherein $R^3$ is selected from the group consisting of

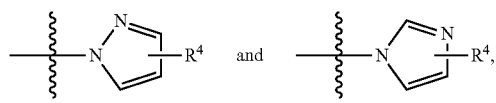

may alternatively be prepared according to the process outlined in Scheme 4, below.

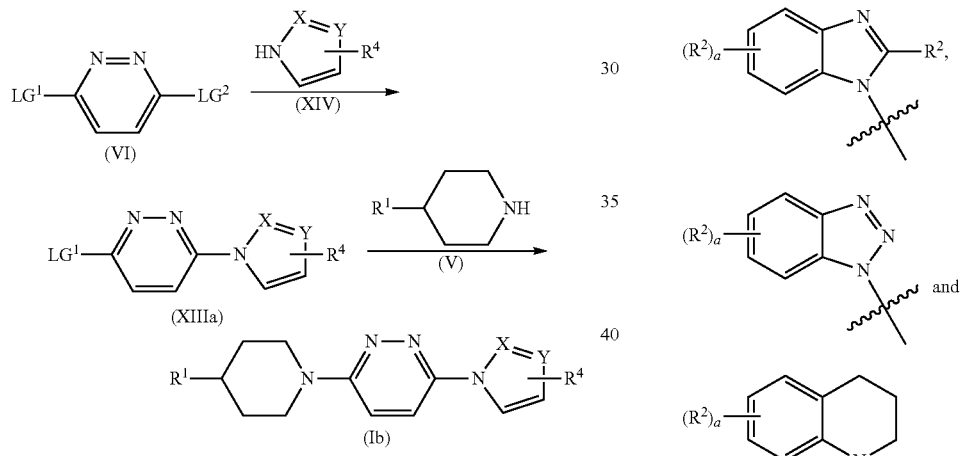

Accordingly, a suitably substituted compound of formula (VI), wherein $LG^1$ and $LG^2$ are suitably selected leaving groups, such as chloro, bromo, iodo, and the like, preferably chloro, preferably $LG^1$ and $LG^2$ are the same, and are each chloro (i.e. 3,6-dichloropyradizine, a known compound) is reacted with a compound of formula (XIV), wherein X is N and Y is C or X is C and Y is N, a known compound or compound prepared by known methods; in the presence of a suitably selected inorganic base such as $Cs_2CO_3$, $K_2CO_3$, $Na_2CO_3$, and the like; in a suitably selected organic solvent such as acetonitrile, DMSO, DMF, and the like; to yield the corresponding compound of formula (XIIIa) (a compound of formula (XIII) wherein $R^3$ is selected from the group consisting of

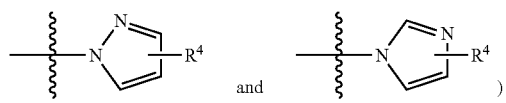

The compound of formula (XIIa) is reacted with a suitably substituted compound of formula (V), a known compound or compound prepared by known methods, in the presence of a suitably selected organic base such as TEA, DIPEA, pyridine, and the like; in a suitably selected organic solvent such as DMSO, DMF, and the like; to yield the corresponding compound of formula (Ib).

Compounds of formula (V) wherein $R^1$ is selected from the group consisting of

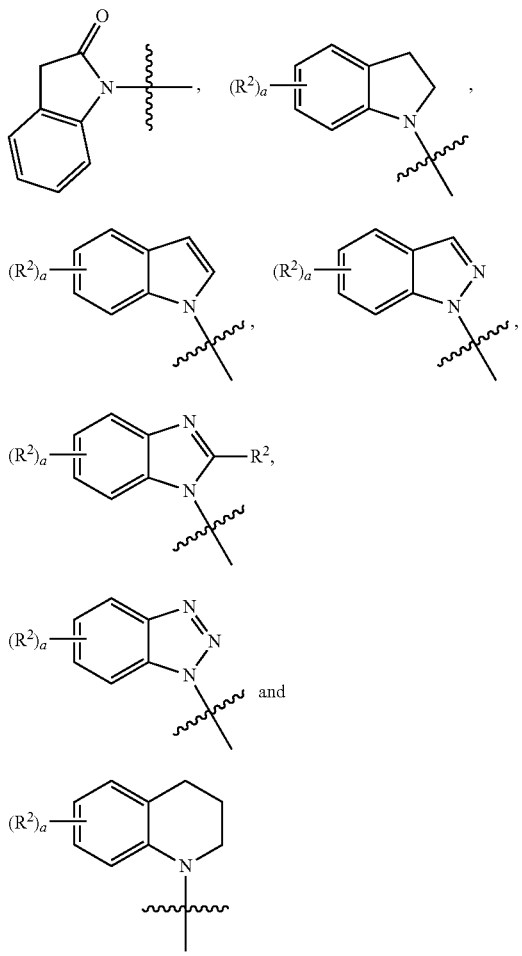

are known compounds or compounds which may be prepared according to known methods, for example, as outlined in Scheme 5, below.

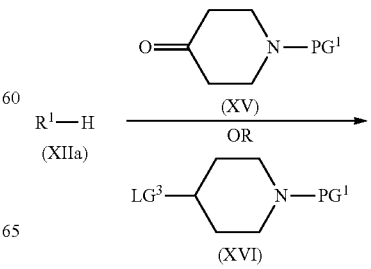

-continued

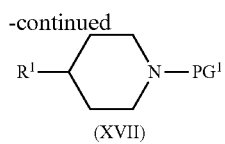

(XVII)

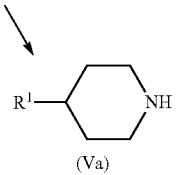

(Va)

Accordingly, a suitably substituted compound of formula (XIIa) (a compound of formula (XII) wherein the R¹ group contains a terminal nucleophillic nitrogen—i.e. R¹ is other than

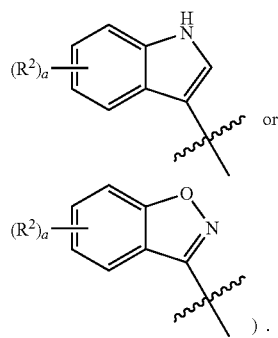

).

a known compound or compound prepared by known methods, is reacted with a suitably substituted compound of formula (XV), wherein PG¹ is a suitably selected nitrogen protecting group such as Boc, CBz, and the like, preferably Boc, a known compound or compound prepared by known methods; in the presence of a suitably selected hydride source such as NaBH(OAc)₃, NaBH₃CN, and the like, preferably NaBH (OAc)₃; in a suitably selected organic solvent such as DCM, DCE, THF, and the like; to yield the corresponding compound of formula (XVII).

Alternatively, a suitably substituted compound of formula (XIIa) (a compound of formula (XII) wherein the R¹ group contains a terminal nucleophillic nitrogen—i.e. R¹ is other than

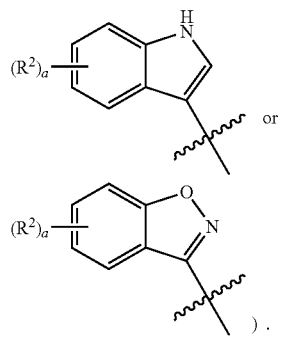

).

a known compound or compound prepared by known methods, is reacted with a suitably substituted compound of formula (XVI), wherein PG¹ is a suitably selected nitrogen protecting group such as Boc, CBz, and the like, preferably Boc, and wherein LG³ is a suitably selected leaving such as —O—SO₂-(p-tolyl), —O—SO₂—CH₃, Br, Cl, I, and the like, a known compound or compound prepared by known methods; in the presence of a suitably selected base such as NaH, LiHMDS, NaHDMS, and the like, preferably NaH; in a suitably selected organic solvent such as THF, DMF, and the like; to yield the corresponding compound of formula (XVII).

The compound of formula (XVII) is de-protected according to known methods; to yield the corresponding compound of formula (Va). For example, wherein PG¹ is Boc, the compound of formula (XVII) may be de-protected by reacting with a suitably selected acid such as HCl, TFA, and the like, in a suitably solvent such as methylene chloride, 1,4-dioxane, and the like. For example, wherein PG¹ is CBz, the compound of formula (XVII) may b de-protected by hydrogenation or by reacting with TMSI, according to known methods.

Compounds of formula (I) wherein R¹ is

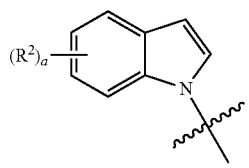

may alternatively be prepared from the corresponding compound of formula (I) wherein R¹ is

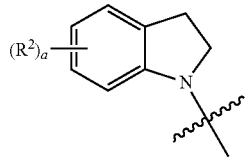

as outlined in Scheme 6, below.

Scheme 6

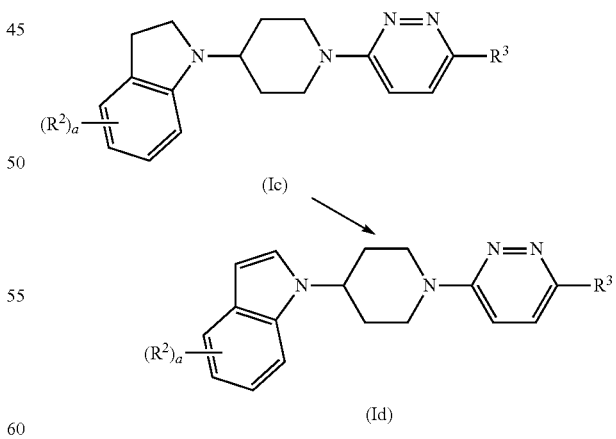

Accordingly, a suitably substituted compound of formula (Ic) is reacted with for example, DDQ, and the like; in a suitably selected organic solvent such as THF, and the like; according to known methods, to yield the corresponding compound of formula (Id) (see for example, Example 12 which follows herein).

Compounds of formula (I) wherein R³ is

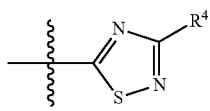

may alternatively be prepared for example, as described in BONGARTZ, J-P., et al., "Synthesis and Anti-Angiogenic Activity of 6-(1,2,4-Thiadiazol-5-yl)-3-amino-pyridazine Derivatives, *Bioorg. Med. Chem. Lett.*, 2002, pp 589-591, Vol. 12(4); PCT Publication WO 98/58929; and/or U.S. Pat. No. 5,985,878.

Compounds of formula (I) wherein R³ is

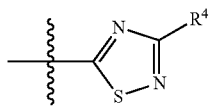

may alternatively be prepared as described in Scheme 7, below.

organic solvent such as DCM, DCE, and the like; to yield the corresponding compound of formula (XX).

The compound of formula (XX) is reacted with a suitably substituted compound of formula (V), a known compound or compound prepared by known methods, in the presence of a suitably selected organic base such as TEA, DIPEA, pyridine, and the like; in a suitably selected organic solvent such as DMSO, DMF, acetonitrile, and the like; under microwave heating or under thermal heating to about 200° C.; to yield the corresponding compound of formula (Ie).

Compounds of formula (V) wherein R¹ is

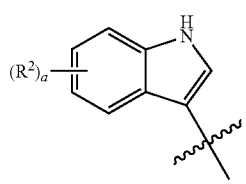

may be prepared as described in Scheme 8, below.

Scheme 7

Scheme 8

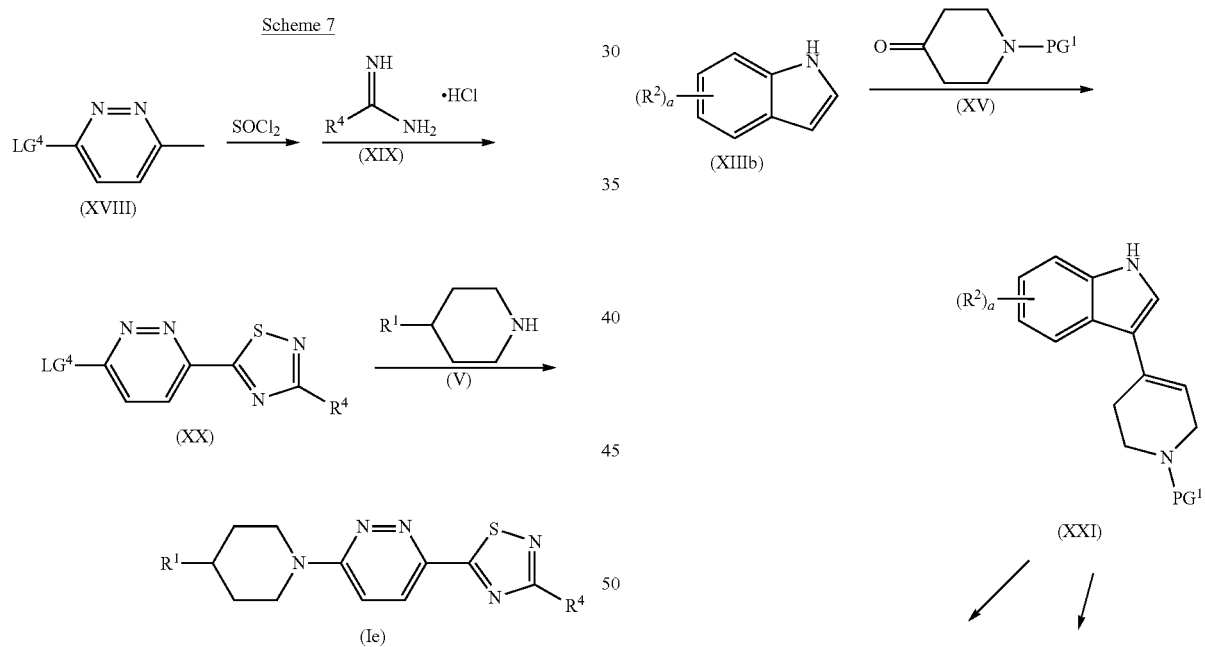

Accordingly, a suitably substituted compound of formula (XVIII), wherein LG⁴ is a suitably selected leaving group such as Cl, Br, I, and the like, preferably chloro, a known compound or compound prepared by known methods, is reacted with a suitably selected source of sulfur such as SOCl₂, and the like;

and then reacted with a suitably substituted compound of formula (XIX) (wherein the compound of formula (XIX) is present as its corresponding HCl salt as noted in the scheme above), a known compound or compound prepared by known methods; in the presence of a suitably selected aqueous base such as NaOH, KOH, and the like; in a suitably selected Accordingly, a suitably substituted compound of formula (XIIb), (a compound of formula (XII) wherein the R¹ is

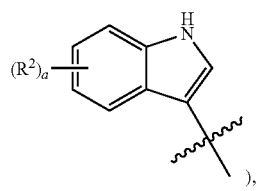

), a known compound or compound prepared by known methods, is reacted with a suitably substituted compound of formula (XV), wherein PG¹ is a suitably selected nitrogen protecting group such as Boc, CBz, benzyl, and the like, preferably Boc, a known compound or compound prepared by known methods; in the presence of a suitably selected organic base such as KOH, NaOH, and the like; in a suitably selected organic solvent such as methanol, ethanol, isopropanol, and the like; to yield the corresponding compound of formula (XXI).

The compound of formula (XXI) is hydrogenated, according to known methods, for example in the presence of hydrogen source, such as $H_2$, ammonium formate, and the like; in the presence of suitably selected catalyst, such as Pd/C, Pt/C and the like, preferably Pd/C; in the presence of suitably selected solvent, such as MeOH, EtOH, and the like; to yield the corresponding compound of formula (XXII).

The compound of formula (XXII) is de-protected according to known methods; to yield the corresponding compound of formula (Vb). For example, wherein PG¹ is Boc, the compound of formula (XXII) may be de-protected by reacting with a suitably selected acid such as HCl, TFA, and the like, in a suitable solvent such as dichloromethane, and the like.

Alternatively, wherein PG¹ is Cbz or benzyl, the protecting group may be de-protected simultaneously during the formation of formula (XXII), under the hydrogenated conditions, as described above.

Compounds of formula (V) wherein R¹ is

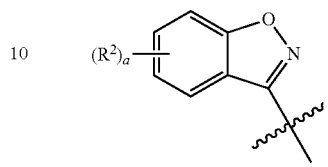

may be prepared as described Scheme 9, below.

Scheme 9

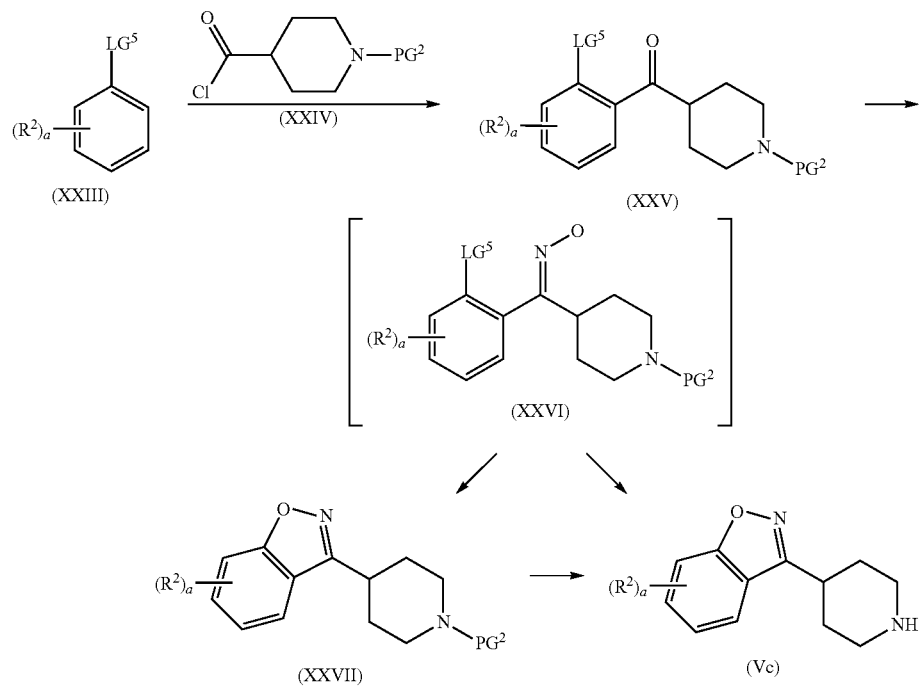

Accordingly, a suitably substituted compound of formula (XXIII), a known compound or compound prepared by known methods, is reacted with a suitably substituted compound of formula (XXIV), wherein LG⁵ is a suitably selected leaving group such as fluoro, bromo, chloro, and the like and wherein PG² is a suitably selected nitrogen protecting group such as acetyl, Cbz, benzyl, and the like, preferably acetyl, a known compound or compound prepared by known methods; in the presence a suitably selected Lewis acid, such as $AlCl_3$, and the like; to yield the corresponding compound of formula (XXV).

The compound of formula (XXV) is reacted with hydroxylamine HCl salt in the presence of a suitably selected base, such as KOH, NaOH, ammonium acetate, and the like; in a suitable selected solvent, such as ethanol, methanol, isopropanol, and the like; at a temperature in the range of from about room temperature to about reflux temperature, preferably at about 85° C., to yield the corresponding compound of formula (XXVI), which compound is preferably not isolated.

The compound of formula (XXVI) is reacted in the presence of a suitably selected base, such as KOH, sodium ethoxide, and the like, at a temperature in the range of from about room temperature to about reflux temperature, to yield the corresponding compound of formula (XXVII).

The compound of formula (XXVII) is de-protected according to known methods, to yield the corresponding compound of formula (Vc). For example, wherein $PG^2$ is Cbz or benzyl, the compound of formula (XXVII) may be de-protected under hydrogenation conditions, according to known methods.

Alternatively, wherein $PG^2$ is acetyl, the compound of formula (XXVI) may be reacted to cyclize and remove the protecting group in step, by reacting with a suitably selected base such as KOH, NaOH, and the like, wherein the base is present in an excess amount, at about reflux temperature, to yield the corresponding compound of formula (Vc).

One skilled in the art will recognize that wherein the $R^3$ group on the compound of formula (I) is substituted (as defined herein), said substituent group(s) may be present in the reactant compound(s) used in the synthesis of the compound of formula (I), as described herein (e.g. in the compound of formula (VIII), in the compound of formula (XI), etc.). Alternatively, said substituent group(s) may be incorporated into the compound of formula (I) by reacting a compound of formula (I) substituted with a precursor group, according to known methods/chemical transformation, to convert said precursor group to the desired substituent group. Representative examples of such transformation are as described below.

Compounds of formula (I) wherein the $R^3$ group is substituted with $-C_{1-2}alkyl-O-C_{1-2}alkyl$ may be prepared from the corresponding compound of formula (I) wherein the $R^3$ group is substituted with $-C_{1-2}alkyl-OH$ by reacting with a suitably selected alkylating agent, according to known methods. (See for example, Example 18 which follows herein.)

Compounds of formula (I) wherein the $R^3$ group is substituted with $-C_2alkyl-OH$ may be prepared from the corresponding compound of formula (I) wherein the $R^3$ group is substituted with $-C_2alkyl-C(O)O-C_{1-2}alkyl$ by reacting with a suitably selected reducing agent, such as $NaBH_4$, and the like; in a suitably selected organic solvent such as EtOH, and the like, according to known methods. (See for example, Example 21 which follows herein.)

Compounds of formula (I) wherein the $R^3$ group is substituted with $-C_{1-2}alkyl-C(O)-NR^AR^B$ may be prepared from the corresponding compound of formula (I) wherein the $R^3$ group is substituted with $-C_{1-2}alkyl-C(O)OCH_3$ or $-C_{1-2}alkyl-C(O)O-CH_2CH_3$ by reacting with a suitably substituted amine of formula $(NHR^AR^B)$, in a suitably selected organic solvent such as EtOH, and the like, according to known methods. (See for example, Example 22 which follows herein.)

Compounds of formula (I) wherein $R^3$

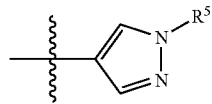

and wherein $R^5$ is $(C_{2-3}alkyl)-O-(C_{1-2}\ alkyl)$ may be prepared by reacting the corresponding compound of formula (I) wherein $R^5$ is hydrogen with a suitably substituted compound of the formula $LG^5-(C_{2-3}alkyl)-O-(C_{1-2}alkyl)$, wherein $LG^5$ is a suitably selected leaving group such as Br, according to known methods. (See for example, Example 23, which follows herein.)

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 1000 mg or any amount or range therein, and may be given at a dosage of from about 0.01 mg/kg/day to about 300 mg/kg/day, or any amount or range therein, preferably from about 0.1 mg/kg/day to about 50 mg/kg/day, or any amount or range therein, preferably from about 0.05 mg/kg/day to about 15 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a mixture of a compound of the present invention, or a pharmaceutically acceptable salt thereof. This solid preformulation composition is then subdivided into unit dosage forms of the type described above containing from about 0.01 mg to about 1,000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating SCD1 disorders described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably from about 1.0 mg to about 500 mg of the compound, or any amount or range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methylcellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment of SCD1 disorders is required.

The daily dosage of the products may be varied over a wide range from about 0.01 mg to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 500 mg/kg of body weight per day, or any amount or range therein. Preferably, the range is from about 0.1 to about 50.0 mg/kg of body weight per day, or any amount or range therein. More preferably, from about 0.5 to about 15.0 mg/kg of body weight per day, or any amount or range therein. More preferably, from about 1.0 to about 7.5 mg/kg of body weight per day, or any amount or range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

In the Examples which follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

EXAMPLE 1

6-fluoro-1-(1-(6-(1-methyl-1H-pyrazol-4-yl)pyridazin-3-yl)piperidin-4-yl)indoline (Compound #11)

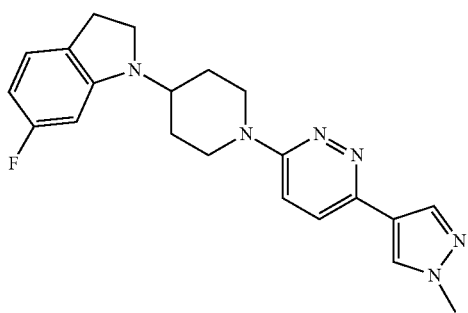 [SMILES: Cn1cc(-c2ccc(N3CCC(N4CCc5ccc(F)cc54)CC3)nn2)cn1]

The title compound was prepared according to two different synthetic methods, as described in more detail below.

Method A

Step 1: tert-butyl 4-(6-fluoroindolin-1-yl)piperidine-1-carboxylate

To a solution of 6-fluoroindoline (9.36 g, 68 mmol) in $CH_2Cl_2$ (100 mL) was added 1-Boc-4-piperidone (13.6 g, 68 mmol). The resulting mixture was stirred at room temperature for 1 h and $NaBH(OAc)_3$ (18 g, 85 mmol, 1.25 equiv) was added. The resulting mixture was stirred at room temperature for 24 h and was then poured slowly to a vigorously stirred $Na_2CO_{3(aq)}$. After 30 min stirring, the layers were separated. The aqueous layer was extracted with $CH_2Cl_2$ (100 mL). The combined organic layer was washed with brine (100 mL), dried ($Na_2SO_4$), and filtered.

The solvent was removed by roto-evaporator and then, $Et_2O$ (10 mL) and then hexane (150 mL) were added to the resulting residue. The resulting mixture was allowed to stand, resulting in the formation of a white solid, which was collected and washed with 5% $Et_2O$/hexane and then dried. This procedure was repeated to yield tert-butyl 4-(6-fluoroindolin-1-yl)piperidine-1-carboxylate as a white solid.

Step 2: 6-fluoro-1-(piperidin-4-yl)indoline

To a solution of tert-butyl 4-(6-fluoroindolin-1-yl)piperidine-1-carboxylate prepared as in STEP 1 above (16.64 g, 52 mmol) in $CH_2Cl_2$ (45 mL) was added TFA (30 mL) slowly at room temperature. The resulting mixture was stirred at room temperature for 3 h (monitor by HPLC). The resulting mixture was then concentrated to remove most of the solvent and TFA. The resulting residue was partitioned in $CH_2Cl_2/H_2O$ (100 mL/50 mL) and stirred. 3N NaOH(aq) was then added slowly until the pH value of aqueous layer was >11. The aqueous layer was then extracted with $CH_2Cl_2$ (100 mL×10). The combined $CH_2Cl_2$ layer was dried ($Na_2SO_4$) and filtered. The solvent was removed and the resulting residue was dissolved in $Et_2O$ (100 mL) and then 1N HCl (1M in $Et_2O$, 60 mL, 60 mmol) was added slowly at 0° C. The resulting mixture was allowed to warm to room temperature for another 30 min. Hexane (100 mL) was added and the resulting mixture was stirred for 15 min. The resulting white solid was filtered and washed with 50% $Et_2O$/hexane (30 mL×3), then dried to yield 6-fluoro-1-(piperidin-4-yl)indoline as a white HCl salt.

Step 3: 1-(1-(6-chloropyridazin-3-yl)piperidin-4-yl)-6-fluoroindoline

In a 100 mL flask was placed 6-fluoro-1-(piperidin-4-yl)indoline as its corresponding HCl salt, prepared as in STEP 2 above (7.7 g, 30 mmol, 1 equiv) and 3,6-dichloropyridazine (4.69 g, 31.5 mmol, 1.05 equiv). DMSO (40 mL) and $Et_3N$ (12.54 mL, 90 mmol, 3 equiv) were added sequentially. The resulting mixture was heated at 80° C. for 7 h. The resulting mixture was then poured into vigorously stirred $H_2O$ (800 mL) and stirred for 1 h. The resulting solid was filtered and washed with $H_2O$ (30 mL×2), 50% $Et_2O$/hexane (30 mL×2), and the dried to yield 1-(1-(6-chloropyridazin-3-yl)piperidin-4-yl)-6-fluoroindoline as a solid.

Step 4: 6-fluoro-1-(1-(6-(1-methyl-1H-pyrazol-4-yl)pyridazin-3-yl)piperidin-4-yl)indoline In a two-neck flask was placed 1-(1-(6-chloropyridazin-3-yl)piperidin-4-yl)-6-fluoroindoline, prepared as in STEP 3 above (2.33 g, 7 mmol, 1 equiv), 1-methylpyrazole-4-boronic acid pinacol ester (1.75 g, 8.4 mmol, 1.2 equiv), $K_2CO_3$ (3.86 g, 28 mmol, 4.0 equiv), and $Pd(PPh_3)_4$ (809 mg, 0.7 mmol, 0.1 equiv). The resulting mixture was degassed and refilled with $N_2$ (3 times). 1,4-Dioxane/$H_2O$ (30 mL/6 mL) was added and the resulting mixture was heated at 100° C. for 3 h. The resulting mixture was poured into EtOAc/$H_2O$ (100 mL/100 mL). The organic layer was washed with brine (100 mL), dried ($Na_2SO_4$), and filtered. The solvent was removed by roto-evaporator, and the resulting residue was purified by column using EtOAc as the eluent to yield the title compound as a solid.

$^1$H NMR (400 MHz, CHLOROFORM-d) δ=7.96 (s, 1 H), 7.91 (s, 1 H), 7.39 (d, J=9.6 Hz, 1 H), 6.98 (d, J=9.6 Hz, 1 H), 6.88-6.96 (m, 1 H), 6.27 (ddd, J=2.3, 7.8, 9.7 Hz, 1 H), 6.15 (dd, J=2.3, 10.6 Hz, 1 H), 4.50-4.61 (m, 2 H), 3.93-4.00 (m, 3

H), 3.52-3.67 (m, 1 H), 3.40 (t, J=8.5 Hz, 2 H), 2.97-3.11 (m, 2 H), 2.90 (t, J=8.3 Hz, 2 H), 1.93 (d, J=13.6 Hz, 2 H), 1.74 (qd, J=3.9, 12.4 Hz, 2 H); MS: 379 (M$^+$+1).

Method B

Step 1: 3-chloro-6-(1-methyl-1H-pyrazol-4-yl)pyridazine

In a two-neck flask was placed 3,6-dichloropyridazine (1.49 g, 10 mmol), 1-methylpyrazole-4-boronic acid pinacol ester (1.04 g, 5 mmol), K$_2$CO$_3$ (1.38 g, 10 mmol), and Pd(PPh$_3$)$_4$ (289 mg, 0.25 mmol). The resulting mixture was degassed and refilled with N$_2$ (3 times). 1,4-Dioxane/H$_2$O (9 mL/2 mL) was added and the resulting mixture was heated at 100° C. for 5 h. The resulting mixture was poured into EtOAc/H$_2$O (30 mL/30 mL). The organic layer was washed with brine (30 mL), dried (Na$_2$SO$_4$), and filtered. The solvent was removed and the resulting residue was purified by column using 90-100% EtOAc/hexane as the eluent to yield 3-chloro-6-(1-methyl-1H-pyrazol-4-yl)pyridazine.

Step 2: 6-fluoro-1-(1-(6-(1-methyl-1H-pyrazol-4-yl)pyridazin-3-yl)piperidin-4-yl)indoline To a mixture of 6-fluoro-1-(piperidin-4-yl)indoline (256 mg, 1 mmol), 3-chloro-6-(1-methyl-1H-pyrazol-4-yl)pyridazine prepared as in STEP 1 above (194 mg, 1.0 mmol) in DMSO (3 mL) was added DIPEA (0.52 mL, 3 mmol). The resulting mixture was sealed and heated at 180° C. for 1.5 h under microwave irradiation. The resulting mixture was poured into H$_2$O (30 mL) and the aqueous layer was extracted with 30% CH$_2$Cl$_2$/Et$_2$O (30 mL×5). The combined organic layer was dried (Na$_2$SO$_4$) and filtered. The solvent was removed and the resulting residue was purified by column using 90-100% EtOAc/hexane as the eluent to yield the title compound, 6-fluoro-1-(1-(6-(1-methyl-1H-pyrazol-4-yl)pyridazin-3-yl)piperidin-4-yl)indoline.

EXAMPLE 2

1-(1-(6-(1-methyl-1H-pyrazol-4-yl)pyridazin-3-yl)piperidin-4-yl)indoline (Compound #10)

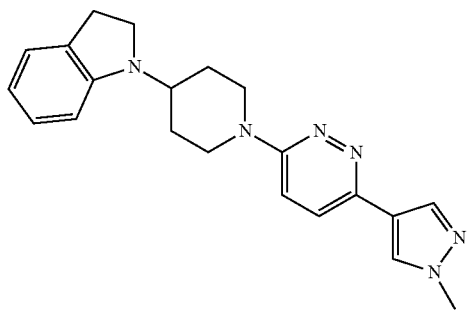 [SMILES: Cn1cc(-c2ccc(N3CCC(N4CCc5ccccc54)CC3)nn2)cn1]

The title compound was prepared according to the procedure as described in Example 1, Method B, reacting 1-(piperidin-4-yl)indoline HCl salt and 3-chloro-6-(1-methyl-1H-pyrazol-4-yl)pyridazine.

$^1$H NMR (400 MHz, CHLOROFORM-d) δ=7.96 (s, 1 H), 7.91 (s, 1 H), 7.39 (d, J=9.6 Hz, 1 H), 7.02-7.11 (m, 2 H), 6.98 (d, J=9.6 Hz, 1 H), 6.63 (t, J=7.3 Hz, 1 H), 6.48 (d, J=7.8 Hz, 1 H), 4.44-4.62 (m, 2 H), 3.91-4.01 (m, 3 H), 3.62-3.75 (m, 1 H), 3.35 (t, J=8.3 Hz, 2 H), 3.04 (td, J=2.4, 12.9 Hz, 2 H), 2.95 (t, J=8.3 Hz, 2 H), 1.94 (d, J=10.6 Hz, 2 H), 1.75 (qd, J=4.2, 12.3 Hz, 2H); MS: 361 (M$^+$+1).

EXAMPLE 3

1-(1-(6-(1-methyl-1H-pyrazol-4-yl)pyridazin-3-yl)piperidin-4-yl)-1H-indole (Compound #9)

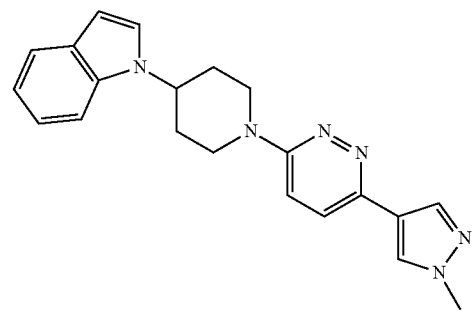 [SMILES: Cn1cc(-c2ccc(N3CCC(n4ccc5ccccc54)CC3)nn2)cn1]

The title compound was prepared according to the procedure as described in Example 1, Method B, reacting 1-(piperidin-4-yl)indole HCl salt and 3-chloro-6-(1-methyl-1H-pyrazol-4-yl)pyridazine.

$^1$H NMR (400 MHz, CHLOROFORM-d) δ=7.98 (s, 1 H), 7.93 (s, 1 H), 7.65 (d, J=7.8 Hz, 1 H), 7.43 (dd, J=3.5, 8.8 Hz, 2 H), 7.20-7.25 (m, 1 H), 7.19 (d, J=3.3 Hz, 1 H), 7.09-7.15 (m, 1 H), 7.04 (d, J=9.6 Hz, 1 H), 6.53 (d, J=2.8 Hz, 1 H), 4.58-4.69 (m, 2 H), 4.46-4.58 (m, 1 H), 3.98 (s, 3 H), 3.11-3.27 (m, 2 H), 2.18-2.31 (m, 2 H), 2.04-2.18 (m, 2 H); MS: 359 (M$^+$+1).

EXAMPLE 4

5-fluoro-3-(1-(6-(1-methyl-1 H-pyrazol-4-yl)pyridazin-3-yl)piperidin-4-yl)benzo[d]isoxazole (Compound #3)

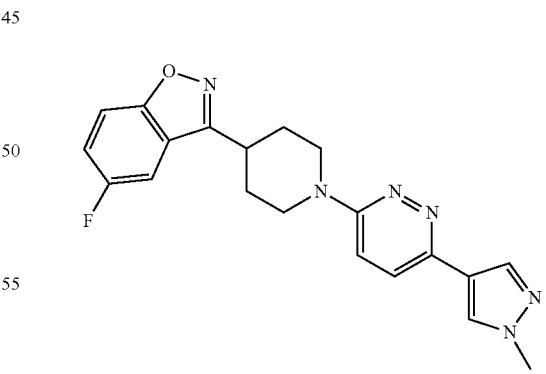

The title compound was prepared following the procedure as described in Example 1, Method B, reacting 5-fluoro-3-(piperidin-4-yl)benzisoxazole HCl salt and 3-chloro-6-(1-methyl-1 H-pyrazol-4-yl)pyridazine.

$^1$H NMR (400 MHz, CHLOROFORM-d) δ=7.97 (s, 1 H), 7.92 (s, 1 H), 7.53 (dd, J=3.7, 9.0 Hz, 1 H), 7.42 (d, J=9.6 Hz, 1 H), 7.27-7.38 (m, 2 H), 7.02 (d, J=9.3 Hz, 1 H), 4.52 (d,

J=13.4 Hz, 2 H), 3.98 (s, 3 H), 3.31-3.45 (m, 1 H), 3.11-3.31 (m, 2 H), 2.03-2.31 (m, 4 H); MS: 379 (M++1).

EXAMPLE 5

4-fluoro-1-(1-(6-(1-methyl-1H-pyrazol-4-yl)pyridazin-3-yl)piperidin-4-yl)indoline (Compound #66)

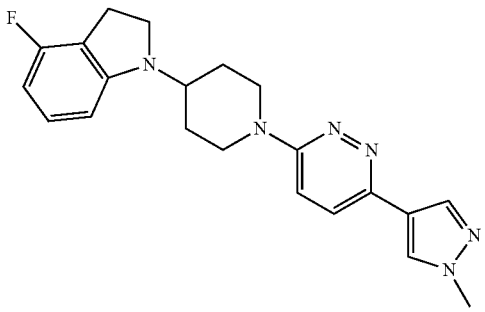 [SMILES: Cn1cc(-c2ccc(N3CCC(N4CCc5c(F)cccc54)CC3)nn2)cn1]

Step 1: 8-(6-chloropyridazin-3-yl)-1,4-dioxa-8-azaspiro[4.5]decane

To a mixture of 3,6-dichloropyridazine (2.98 g, 20 mmol) in DMSO (10 mL) was added 1,4-dioxa-8-azaspiro[4.5]decane (3 g, 21 mmol) and DIPEA (4.18 mL, 24 mmol). The resulting mixture was heated at 80° C. for 4 h and was then poured into $H_2O$ (300 mL). The resulting solid was washed with $H_2O$ (10 mL×3) and hexane (10 mL×3) and then dried to yield 8-(6-chloropyridazin-3-yl)-1,4-dioxa-8-azaspiro[4.5]decane.

Step 2: 8-(6-(1-methyl-1H-pyrazol-4-yl)pyridazin-3-yl-1,4-dioxa-8-azaspiro[4.5]decane In a two-neck flask was placed 8-(6-chloropyridazin-3-yl)-1,4-dioxa-8-azaspiro[4.5]decane, prepared as in STEP 1 above (3.07 g, 12 mmol), 1-methylpyrazole-4-boronic acid pinacol ester (3.24 g, 15.6 mmol), $K_2CO_3$ (6.62 g, 48 mmol), and $Pd(PPh_3)_4$ (693 mg, 0.6 mmol). The resulting mixture was degassed and refilled with $N_2$ (3 times). 1,4-Dioxane/$H_2O$ (15 mL/5 mL) was added and the resulting mixture was heated at 100° C. for 4 h. The resulting mixture was then poured into EtOAc/$H_2O$ (100 mL/100 mL). The organic layer was washed with brine (100 mL), dried ($Na_2SO_4$), and filtered. The solvent was removed by roto-evaporator and the resulting residue purified by column using EtOAc as the eluent to yield 8-(6-(1-methyl-1H-pyrazol-4-yl)pyridazin-3-yl)-1,4-dioxa-8-azaspiro[4.5]decane.

Step 3: 1-(6-(1-methyl-1H-pyrazol-4-yl)pyridazin-3-yl)piperidin-4-one

To a solution of 8-(6-(1-methyl-1H-pyrazol-4-yl)pyridazin-3-yl)-1,4-dioxa-8-azaspiro[4.5]decane, prepared as in STEP 2 above (1.8 g, 6 mmol) in acetone/$H_2O$ (30 mL/30 mL) was added p-TSA.$H_2O$ (1.37 g, 7.2 mmol). The resulting mixture was stirred at 65° C. for 6 h and then concentrated to remove most of organic solvent. The residue was poured into $CH_2Cl_2$/$H_2O$/$Na_2CO_3$(aq) (50 mL/25 mL/25 mL). The aqueous layer was extracted with $CH_2Cl_2$ (50 mL). The combined organic layer was dried ($Na_2SO_4$), and filtered. The solvent was removed by roto-evaporator to yield 1-(6-(1-methyl-1H-pyrazol-4-yl)pyridazin-3-yl)piperidin-4-one as a solid.

Step 4: 4-fluoro-1-(1-(6-(1-methyl-1H-pyrazol-4-yl)pyridazin-3-yl)piperidin-4-yl)indoline To a mixture of 4-fluoroindoline (62 mg, 0.45 mmol) and 1-(6-(1-methyl-1H-pyrazol-4-yl)pyridazin-3-yl)piperidin-4-one, prepared as in STEP 3 above (77 mg, 0.3 mmol) in $CH_2Cl_2$ (3 mL) was added $NaBH(OAc)_3$ (126 mg, 0.6 mmol). The resulting mixture was stirred at room temperature for 24 h and then concentrated. The resulting mixture was purified by column using 90-100% EtOAc/($CH_2Cl_2$/hexane=1/1) as the eluent to yield the 4-fluoro-1-(1-(6-(1-methyl-1H-pyrazol-4-yl)pyridazin-3-yl)piperidin-4-yl)indoline as a residue. The title compound was then converted to its corresponding HCl salt.

$^1$H NMR (400 MHz, DMSO-$d_6$) δ=8.54 (s, 1 H), 8.26 (d, J=10.2 Hz, 1 H), 8.11-8.22 (m, 2 H), 6.96-7.07 (m, 1 H), 6.41 (d, J=7.8 Hz, 1 H), 6.33 (t, J=8.6 Hz, 1 H), 4.45 (d, J=14.1 Hz, 2 H), 3.92 (s, 3 H), 3.79-3.90 (m, 1 H), 3.36 (t, J=10 Hz, 2 H), 3.26 (t, J=12.1 Hz, 2 H), 2.89 (t, J=8.6 Hz, 2 H), 1.76-1.88 (m, 2 H), 1.60-1.76 (m, 2 H); MS: 379 (M++1).

EXAMPLE 6

5-fluoro-1-(1-(6-(1-methyl-1H-pyrazol-4-yl)pyridazin-3-yl)piperidin-4-yl)indoline (Compound #46)

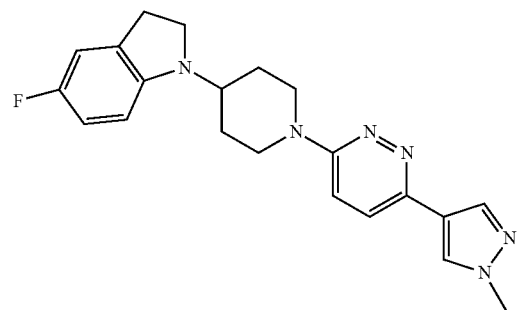 [SMILES: Cn1cc(-c2ccc(N3CCC(N4CCc5cc(F)ccc54)CC3)nn2)cn1]

The title compound was prepared following the procedure as described in Example 5, STEP 4, reacting 5-fluoroindoline and 1-(6-(1-methyl-1H-pyrazol-4-yl)pyridazin-3-yl)piperidin-4-one.

$^1$H NMR (400 MHz, CHLOROFORM-d) δ=7.96 (s, 1 H), 7.90 (s, 1 H), 7.39 (d, J=9.3 Hz, 1 H), 6.98 (d, J=9.3 Hz, 1 H), 6.69-6.85 (m, 2 H), 6.35 (dd, J=4.2, 8.5 Hz, 1 H), 4.48-4.61 (m, 2 H), 3.93-4.01 (m, 3 H), 3.61 (tt, J=3.7, 11.7 Hz, 1 H), 3.33 (t, J=8.3 Hz, 2 H), 3.03 (td, J=2.3, 12.9 Hz, 2 H), 2.92 (t, J=8.3 Hz, 2 H), 1.92 (d, J=13.6 Hz, 2 H), 1.72 (qd, J=4.0, 12.4 Hz, 2 H); MS: 379 (M++1).

EXAMPLE 7

5-chloro-1-(1-(6-(1-methyl-1H-pyrazol-4-yl)pyridazin-3-yl)piperidin-4-yl)indoline (Compound #65)

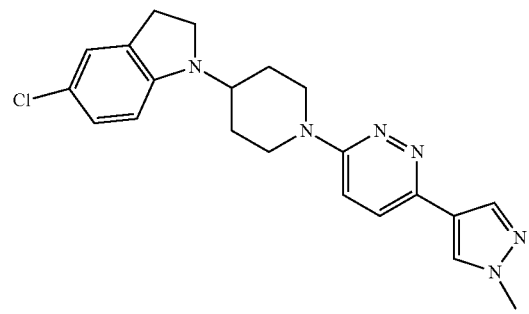 [SMILES: Cn1cc(-c2ccc(N3CCC(N4CCc5cc(Cl)ccc54)CC3)nn2)cn1]

The title compound was prepared following the procedure as described in Example 5, STEP 4, reacting 5-chloroindoline and 1-(6-(1-methyl-1H-pyrazol-4-yl)pyridazin-3-yl)piperidin-4-one.

$^1$H NMR (400 MHz, DMSO-$d_6$) δ=8.56 (s, 1 H), 8.28 (d, J=9.8 Hz, 1 H), 8.21 (s, 1 H), 8.16 (d, J=10.2 Hz, 1 H), 6.98-7.07 (m, 2 H), 6.58 (d, J=8.2 Hz, 1 H), 4.47 (d, J=12.9 Hz, 2 H), 3.94 (s, 3 H), 3.74-3.91 (m, 1 H), 3.17-3.34 (m, 4 H), 2.88 (t, J=8.6 Hz, 2 H), 1.76-1.90 (m, 2 H), 1.60-1.76 (m, 2 H); MS: 395 (M$^+$+1).

EXAMPLE 8

6-chloro-1-(1-(6-(1-methyl-1H-pyrazol-4-yl)pyridazin-3-yl)piperidin-4-yl)indoline (Compound #59)

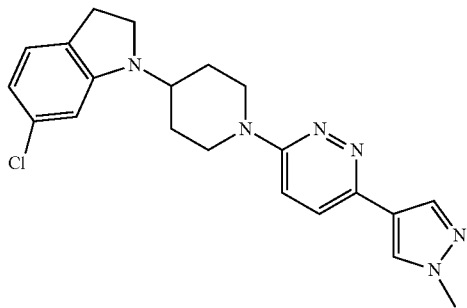 [SMILES: Cn1cc(-c2ccc(N3CCC(N4CCc5ccc(Cl)cc54)CC3)nn2)cn1]

The title compound was prepared following the procedure as described in Example 5, STEP 4, reacting 6-chloroindoline and 1-(6-(1-methyl-1H-pyrazol-4-yl)pyridazin-3-yl)piperidin-4-one.

$^1$H NMR (400 MHz, DMSO-$d_6$) δ=8.55 (s, 1 H), 8.22-8.30 (m, 1 H), 8.20 (s, 1 H), 8.15 (d, J=9.9 Hz, 1 H), 6.98 (d, J=7.8 Hz, 1 H), 6.57-6.65 (m, 1 H), 6.52 (dd, J=1.6, 7.7 Hz, 1 H), 4.46 (d, J=12.4 Hz, 2 H), 3.94 (s, 3 H), 3.82-3.93 (m, 1 H), 3.20-3.42 (m, 4 H), 2.85 (t, J=8.2 Hz, 2 H), 1.82 (d, J=11.6 Hz, 2 H), 1.59-1.77 (m, 2 H); MS: 395 (M$^+$+1).

EXAMPLE 9

6-methyl-1-(1-(6-(1-methyl-1H-pyrazol-4-yl)pyridazin-3-yl)piperidin-4-yl)indoline (Compound #57)

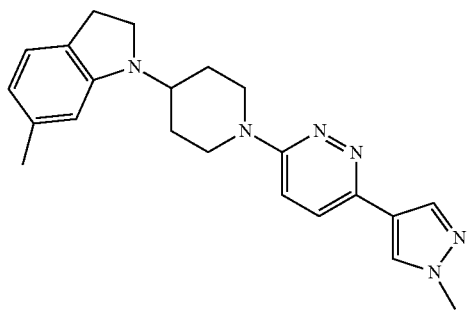 [SMILES: Cc1ccc2c(c1)N(C1CCN(c3ccc(-c4cnn(C)c4)nn3)CC1)CC2]

The title compound was prepared following the procedure as described in Example 5, STEP 4, reacting 6-methylindoline and 1-(6-(1-methyl-1H-pyrazol-4-yl)pyridazin-3-yl)piperidin-4-one.

$^1$H NMR (400 MHz, DMSO-$d_6$) δ=8.55 (s, 1 H), 8.23-8.31 (m, 1 H), 8.20 (s, 1 H), 8.16 (d, J=9.9 Hz, 1 H), 6.91 (d, J=6.6 Hz, 1 H), 6.36-6.55 (m, 2 H), 4.47 (d, J=13.4 Hz, 2 H), 3.94 (s, 3 H), 3.79-3.91 (m, 1 H), 3.21-3.35 (m, 4 H), 2.82 (t, J=8.0 Hz, 2 H), 2.23 (s, 3 H), 1.78-1.89 (m, 2 H), 1.61-1.78 (m, 2H); MS: 375 (M$^+$+1).

EXAMPLE 10

6-methoxy-1-(1-(6-(1-methyl-1H-pyrazol-4-yl)pyridazin-3-yl)piperidin-4-yl)indoline (Compound #62)

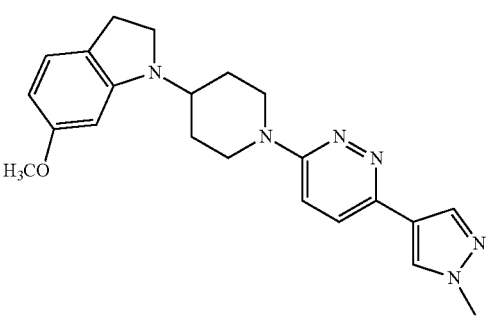 [SMILES: COc1ccc2c(c1)N(C1CCN(c3ccc(-c4cnn(C)c4)nn3)CC1)CC2]

The title compound was prepared following the procedure as described in Example 5, STEP 4, reacting 6-methoxyinoline and 1-(6-(1-methyl-1H-pyrazol-4-yl)pyridazin-3-yl)piperidin-4-one.

$^1$H NMR (400 MHz, DMSO-$d_6$) δ=8.56 (s, 1 H), 8.28 (d, J=9.9 Hz, 1 H), 8.09-8.23 (m, 2 H), 6.90 (d, J=7.8 Hz, 1 H), 6.22 (s, 1 H), 6.08-6.17 (m, 1 H), 4.46 (d, J=13.1 Hz, 2 H), 3.94 (s, 3 H), 3.78-3.91 (m, 1 H), 3.69 (s, 3 H), 3.20-3.35 (m, 4 H), 2.79 (t, J=8.1 Hz, 2 H), 1.84 (d, J=12.1 Hz, 2 H), 1.61-1.78 (m, 2 H); MS: 391 (M$^+$+1).

EXAMPLE 11

1-(1-(6-(1-methyl-1H-pyrazol-4-yl)pyridazin-3-yl)piperidin-4-yl)-6-(trifluoromethyl)indoline (Compound #60)

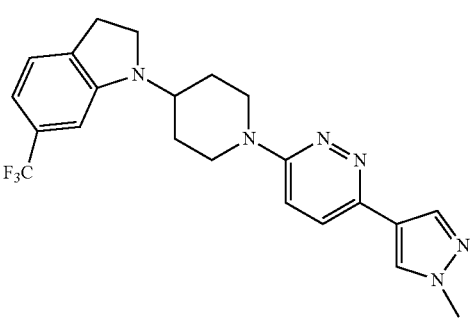 [SMILES: Cn1cc(-c2ccc(N3CCC(N4CCc5ccc(C(F)(F)F)cc54)CC3)nn2)cn1]

The title compound was prepared following the procedure as described in Example 5, STEP 4, reacting 6-trifluoromethylindoline and 1-(6-(1-methyl-1H-pyrazol-4-yl)pyridazin-3-yl)piperidin-4-one.

$^1$H NMR (400 MHz, DMSO-$d_6$) δ=8.53 (s, 1 H), 8.21-8.30 (m, 1 H), 8.19 (s, 1 H), 8.14 (d, J=10.6 Hz, 1 H), 7.17 (d, J=7.3 Hz, 1 H), 6.84 (d, J=7.1 Hz, 1 H), 6.80 (s, 1 H), 4.46 (d, J=13.6 Hz, 2H), 3.96-4.05 (m, 1 H), 3.94 (s, 3 H), 3.35-3.45 (m, 2 H), 3.21-3.35 (m, 2 H), 2.95 (t, J=8.0 Hz, 2 H), 1.73-1.89 (m, 2 H), 1.62-1.73 (m, 2 H); MS: 429 (M++1).

EXAMPLE 12

6-fluoro-1-(1-(6-(1-methyl-1H-pyrazol-4-yl)pyridazin-3-yl)piperidin-4-yl)-1H-indole (Compound #63)

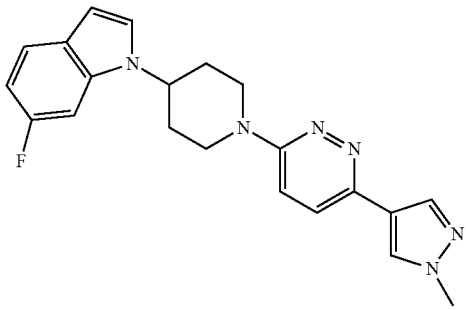 [SMILES: Cn1cc(-c2ccc(N3CCC(n4ccc5ccc(F)cc54)CC3)nn2)cn1]

To a solution of 6-fluoro-1-(1-(6-(1-methyl-1H-pyrazol-4-yl)pyridazin-3-yl)piperidin-4-yl)indoline (75 mg, 0.2 mmol) in THF (3 mL) was added DDQ (54 mg, 0.24 mmol). The resulting mixture was stirred at room temperature for 30 min and was poured into EtOAc (30 mL). The organic layer washed with Na₂CO₃(aq) (30 mL), H₂O (30 mL), dried (Na₂SO₄), and filtered. The solvent was removed and the resulting residue purified by column using 80-90-100% EtOAc/(CH₂Cl₂/hexane=1/1) as the eluent to yield 6-fluoro-1-(1-(6-(1-methyl-1H-pyrazol-4-yl)pyridazin-3-yl)piperidin-4-yl)-1H-indole, which was then converted to its corresponding HCl salt.

¹H NMR (400 MHz, DMSO-d₆) δ=8.53 (s, 1 H), 8.16-8.30 (m, 2 H), 8.11 (d, J=10.4 Hz, 1 H), 7.41-7.60 (m, 3 H), 6.8-6.96 (m, 1 H), 6.48 (d, J=3.0 Hz, 1 H), 4.79 (t, J=7.8 Hz, 1 H), 4.55 (d, J=13.1 Hz, 2 H), 3.94 (s, 3 H), 3.26-3.46 (m, 2 H), 1.97-2.15 (m, 4 H); MS: 377 (M++1).

EXAMPLE 13

6-fluoro-1-(1-(6-(4-methyl-1H-imidazol-1-yl)pyridazin-3-yl)piperidin-4-yl)indoline (Compound #4)

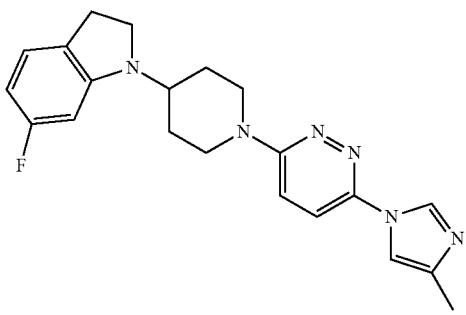 [SMILES: Cc1cn(-c2ccc(N3CCC(N4CCc5ccc(F)cc54)CC3)nn2)cn1]

To a mixture of 6-fluoro-1-(piperidin-4-yl)indoline (128 mg, 0.5 mmol), 3-chloro-6-(4-methylimidazol-1-yl)pyridazine (78 mg, 0.4 mmol) in DMSO (1.5 mL) was added DIPEA (0.25 mL, 1.5 mmol). The resulting mixture was sealed and heated at 180° C. for 1.5 h under microwave irradiation. The resulting mixture was then poured into H₂O (30 mL) and the aqueous layer was extracted with 10% CH₂Cl₂/Et₂O (80 mL×4). The combined organic layer was dried (Na₂SO₄) and filtered. The solvent was removed and the resulting residue was purified by column (dry loading) using EtOAc then 3% MeOH/EtOAc as the eluent to yield 6-fluoro-1-(1-(6-(4-methyl-1H-imidazol-1-yl)pyridazin-3-yl)piperidin-4-yl)indoline.

¹H NMR (400 MHz, CHLOROFORM-d) δ=8.15 (d, J=1.3 Hz, 1 H), 7.29-7.37 (m, 2 H), 7.12 (d, J=9.6 Hz, 1 H), 6.89-6.97 (m, 1 H), 6.28 (ddd, J=2.3, 7.9, 9.8 Hz, 1 H), 6.15 (dd, J=2.1, 10.5 Hz, 1 H), 4.47-4.60 (m, 2 H), 3.53-3.69 (m, 1 H), 3.40 (t, J=8.5 Hz, 2 H), 3.01-3.15 (m, 2 H), 2.91 (t, J=8.3 Hz, 2H), 2.31 (s, 3 H), 1.88-2.01 (m, 2 H), 1.67-1.84 (m, 2 H); MS: 379 (M++1).

EXAMPLE 14

1-(6-(4-(6-fluoroindolin-1-yl)piperidin-1-yl)pyridazin-3-yl)-1H-imidazol-4-yl)methanol (Compound #15

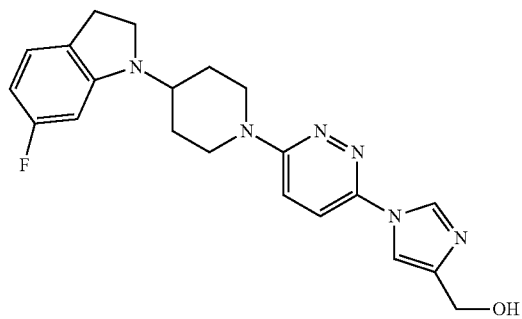 [SMILES: OCc1cn(-c2ccc(N3CCC(N4CCc5ccc(F)cc54)CC3)nn2)cn1]

Step 1: (1-(6-chloropyridazin-3-yl)-1H-imidazol-4-yl)methanol

To a mixture of 3,6-dichloropyridazine (3.73 g, 25 mmol), 4(5)-hydroxymethylimidazole (1.96 g, 20 mmol), and Cs₂CO₃ (8.14 g, 25 mmol) was added acetonitrile (80 mL). The resulting mixture was refluxed for 3 h and was then poured into H₂O (200 mL). 1N HCl(aq) was added slowly until the pH was ~7-8. The aqueous layer was extracted with EtOAc (150 mL) and then CH₂Cl₂ (100 mL×5). The combined organic layer was dried (Na₂SO₄) and filtered. The solvent was removed and the resulting residue was triturated with 10% CH₂Cl₂/Et₂O (30 mL×3) to yield (1-(6-chloropyridazin-3-yl)-1H-imidazol-4-yl)methanol. The filtrate was concentrated and was purified by column using 60-70-80% EtOAc/(CH₂Cl₂/hexane=1/1) as the eluent to yield a second crop of (1-(6-chloropyridazin-3-yl)-1H-imidazol-4-yl)methanol.

Step 2: (1-(6-(4-(6-fluoroindolin-1-yl)piperidin-1-yl)pyridazin-3-yl)-1H-imidazol-4-yl)methanol To a mixture of 6-fluoro-1-(piperidin-4-yl)indoline (100 mg, 0.4 mmol) and (1-(6-chloropyridazin-3-yl)-1H-imidazol-4-yl)methanol, prepared as in STEP 1 above (63 mg, 0.3 mmol) in DMSO (1.5 mL) was added DIPEA (0.16 mL, 0.9 mmol). The resulting mixture was sealed and heated at 180° C. for 1.5 h under microwave irradiation. The resulting mixture was then poured into H₂O (30 mL) and the aqueous layer was extracted with 10% CH₂Cl₂/Et₂O (80 mL×4). The combined organic layer was dried (Na₂SO₄) and filtered. The solvent was removed and the resulting residue was purified by column using EtOAc then 3-5% MeOH/EtOAc as the eluent to yield (1-(6-(4-(6-fluoroindolin-1-yl)piperidin-1-yl)pyridazin-3-yl)-1H-imidazol-4-yl)methanol.

¹H NMR (400 MHz, CHLOROFORM-d) δ=8.24 (s, 1 H), 7.57 (s, 1 H), 7.35 (d, J=9.9 Hz, 1 H), 7.13 (d, J=9.9 Hz, 1 H), 6.87-6.98 (m, 1 H), 6.29 (ddd, J=2.3, 7.8, 9.7 Hz, 1 H), 6.15 (dd, J=2.3, 10.6 Hz, 1 H), 4.70 (s, 2 H), 4.46-4.64 (m, 2 H), 3.51-3.72 (m, 1 H), 3.41 (t, J=8.3 Hz, 2 H), 3.10 (td, J=2.3, 12.9 Hz, 2 H), 2.91 (t, J=8.3 Hz, 2 H), 1.88-2.02 (m, 2 H), 1.75 (qd, J=4.0, 12.5 Hz, 2 H) (OH not seen); MS: 395 (M⁺+1).

EXAMPLE 15

6-fluoro-1-(1-(6-(4-methyl-1H-pyrazol-1-yl)pyridazin-3-yl)piperidin-4-yl)indoline (Compound #16)

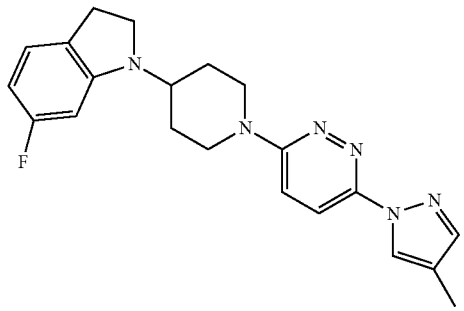 [SMILES: Cc1cnn(-c2ccc(N3CCC(N4CCc5ccc(F)cc54)CC3)nn2)c1]

The title compound was prepared following the procedure as described in Example 14, reacting 4-methylpyrazole, 3,6-dichloropyridazine, and 6-fluoro-1-(piperidin-4-yl)indoline.

¹H NMR (400 MHz, CHLOROFORM-d) δ=8.37 (s, 1 H), 7.97 (d, J=9.6 Hz, 1 H), 7.51-7.58 (m, 1 H), 7.14 (d, J=9.6 Hz, 1 H), 6.87-6.98 (m, 1 H), 6.28 (ddd, J=2.3, 7.8, 9.7 Hz, 1 H), 6.15 (dd, J=2.3, 10.4 Hz, 1 H), 4.52 (dt, J=2.1, 13.6 Hz, 2 H), 3.50-3.68 (m, 1 H), 3.41 (t, J=8.5 Hz, 2 H), 3.07 (td, J=2.5, 13.0 Hz, 2 H), 2.91 (t, J=8.3 Hz, 2 H), 2.17 (s, 3 H), 1.88-1.99 (m, 2 H), 1.76 (qd, J=4.0, 12.5 Hz, 2 H); MS: 379 (M⁺+1).

EXAMPLE 16

1-(6-(4-(6-fluoroindolin-1-yl)piperidin-1-yl)pyridazin-3-yl)-1H-pyrazol-4-yl)methanol (Compound #22)

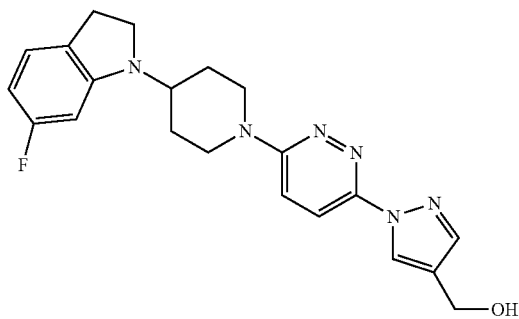 [SMILES: OCc1cnn(-c2ccc(N3CCC(N4CCc5ccc(F)cc54)CC3)nn2)c1]

The title compound was prepared following the procedure as described in Example 14, reacting 4-hydroxymethylpyrazole, 3,6-dichloropyridazine, and 6-fluoro-1-(piperidin-4-yl)indoline.

¹H NMR (400 MHz, CHLOROFORM-d) δ=8.60 (s, 1 H), 7.98 (d. J=9.9 Hz, 1 H), 7.76 (s, 1 H), 7.16 (d, J=9.9 Hz, 1 H), 6.85-6.97 (m, 1 H), 6.28 (ddd, J=2.3, 7.8, 9.7 Hz, 1 H), 6.16 (dd, J=2.3, 10.6 Hz, 1 H), 4.70 (d, J=5.8 Hz, 2 H), 4.46-4.61 (m, 2 H), 3.52-3.69 (m, 1 H), 3.41 (t, J=8.3 Hz, 2 H), 2.99-3.15 (m, 2 H), 2.91 (t, J=8.3 Hz, 2 H), 1.87-2.02 (m, 2 H), 1.66-1.84 (m, 2 H) (OH not seen); MS: 395 (M⁺+1).

EXAMPLE 17

2-(1-(6-(4-(6-fluoroindolin-1-yl)piperidin-1-yl)pyridazin-3-yl)-1H-pyrazol-4-yl)ethanol (Compound #43)

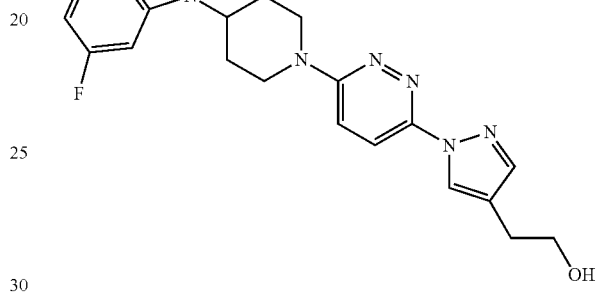

The title compound was prepared following the procedure as described in Example 14, reacting 4-(2-hydroxyethyl)pyrazole, 3,6-dichloropyridazine, and 6-fluoro-1-(piperidin-4-yl)indoline.

¹H NMR (400 MHz, CHLOROFORM-d) δ=8.49 (s, 1 H), 7.97 (d. J=9.6 Hz, 1 H), 7.63 (s, 1 H), 7.15 (d, J=9.9 Hz, 1 H), 6.93 (dd, J=5.9, 8.0 Hz, 1 H), 6.28 (ddd, J=2.3, 7.8, 9.7 Hz, 1 H), 6.15 (dd, J=2.3, 10.6 Hz, 1 H), 4.53 (dd, J=2.0, 11.4 Hz, 2 H), 3.86 (q, J=6.4 Hz, 2 H), 3.51-3.68 (m, 1 H), 3.32-3.47 (m, 2 H), 3.08 (td, J=2.4, 12.8 Hz, 2 H), 2.91 (t, J=8.5 Hz, 2 H), 2.83 (t, J=6.4 Hz, 2 H), 1.95 (d, J=11.6 Hz, 2 H), 1.76 (qd, J=3.9, 12.4 Hz, 2 H) (OH not seen); MS: 409 (M⁺+1).

EXAMPLE 18

1-(1-(6-(4-(ethoxymethyl)-1H-pyrazol-1-yl)pyridazin-3-yl)piperidin-4-yl)-6-fluoroindoline (Compound #72)

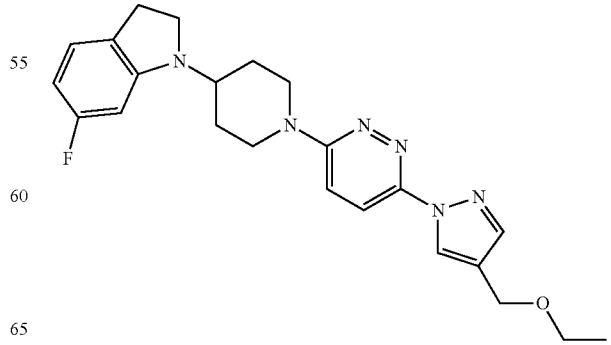

To a mixture of (1-(6-(4-(6-fluoroindolin-1-yl)piperidin-1-yl)pyridazin-3-yl)-1H-pyrazol-4-yl)methanol (59 mg, 0.15 mmol, 1 equiv) and ethyl iodide (93 mg, 0.6 mmol, 4 equiv) was added solvent THF (5 mL) and DMF (1 mL). NaH (36 mg, 60% in mineral oil, 0.9 mmol, 6 equiv) was then added. The resulting mixture was stirred at room temperature for 1.5 h and then poured into Et$_2$O/H$_2$O (20 mL/20 mL). The organic layer was washed with brine (20 mL), dried (Na$_2$SO$_4$), and filtered. The solvent was removed and the resulting residue was purified by column using 40-60% EtOAc/hexane as the eluent to yield 1-(1-(6-(4-(ethoxymethyl)-1H-pyrazol-1-yl)pyridazin-3-yl)piperidin-4-yl)-6-fluoroindoline, which was then re-crystallized from CH$_2$Cl$_2$/hexane upon slow evaporation.

$^1$H NMR (400 MHz, CHLOROFORM-d) δ=8.58 (s, 1 H), 7.98 (d, J=9.6 Hz, 1 H), 7.73 (s, 1 H), 7.15 (d, J=9.6 Hz, 1 H), 6.93 (dd, J=5.8, 7.8 Hz, 1 H), 6.28 (ddd, J=2.4, 7.8, 9.7 Hz, 1 H), 6.16 (dd, J=2.1, 10.5 Hz, 1 H), 4.46-4.60 (m, 4 H), 3.50-3.68 (m, 3 H), 3.35-3.46 (m, 2 H), 3.01-3.14 (m, 2 H), 2.91 (t, J=8.3 Hz, 2 H), 1.95 (d, J=12.9 Hz, 2 H), 1.76 (qd, J=3.8, 12.5 Hz, 2 H), 1.17-1.29 (m, 3 H); MS: 423 (M$^+$+1).

EXAMPLE 19

1-(1-(6-(1-ethyl-1H-pyrazol-4-yl)pyridazin-3-yl)piperidin-4-yl)-6-fluoroindoline (Compound #21)

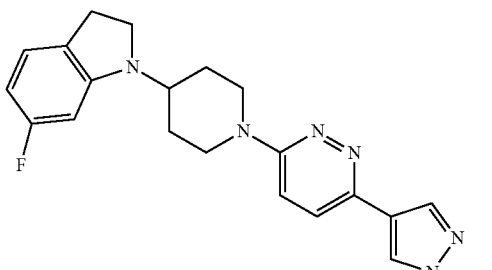

The title compound was prepared following the procedure as described in Example 1, Method A, reacting 1-ethylpyrazole-4-boronic acid pinacol ester and 1-(1-(6-chloropyridazin-3-yl)piperidin-4-yl)-6-fluoroindoline.

$^1$H NMR (400 MHz, CHLOROFORM-d) δ=8.01 (s, 1 H), 7.92 (s, 1 H), 7.40 (d, J=9.6 Hz, 1 H), 6.99 (d, J=9.6 Hz, 1 H), 6.89-6.96 (m, 1 H), 6.27 (ddd, J=2.3, 7.8, 9.7 Hz, 1 H), 6.15 (dd, J=2.3, 10.6 Hz, 1 H), 4.49-4.61 (m, 2H), 4.24 (q, J=7.3 Hz, 2 H), 3.51-3.66 (m, 1 H), 3.40 (t, J=8.5 Hz, 2 H), 3.04 (td, J=2.3, 12.9 Hz, 2 H), 2.90 (t, J=8.3 Hz, 2 H), 1.86-1.98 (m, 2 H), 1.75 (qd, J=3.9, 12.4 Hz, 2 H), 1.54 (t, J=7.0 Hz, 3 H); MS: 393 (M$^+$+1).

EXAMPLE 20

6-fluoro-1-(1-(6-(1-propyl-1H-pyrazol-4-yl)pyridazin-3-yl)piperidin-4-yl)indoline (Compound #79)

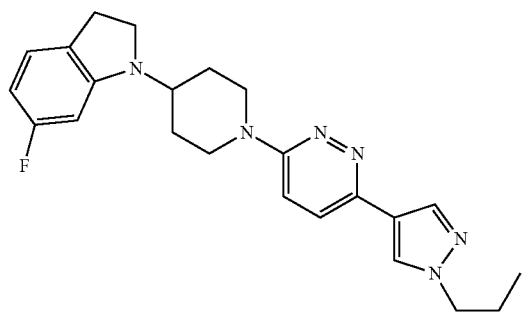 [SMILES: CCCn1cc(-c2ccc(N3CCC(N4CCc5ccc(F)cc54)CC3)nn2)cn1]

The title compound was prepared following the procedure as described in Example 1, Method A, reacting 1-propylpyrazole-4-boronic acid pinacol ester and 1-(1-(6-chloropyridazin-3-yl)piperidin-4-yl)-6-fluoroindoline.

$^1$H NMR (400 MHz, DMSO-d$_6$) δ=8.60 (s, 1 H), 8.28 (d, J=10.1 Hz, 1H), 8.22 (s, 1 H), 8.16 (d, J=9.9 Hz, 1 H), 6.96 (dd, J=6.1, 7.8 Hz, 1 H), 6.45 (dd, J=2.4, 11.0 Hz, 1 H), 6.27 (ddd, J=2.5, 7.8, 9.9 Hz, 1 H), 4.47 (d, J=13.4 Hz, 2 H), 4.16 (t, J=6.9 Hz, 2 H), 3.77-3.90 (m, 1 H), 3.21-3.43 (m, 4 H), 2.84 (t, J=8.5 Hz, 2 H), 1.77-1.89 (m, 4 H), 1.60-1.72 (m, 2 H), 0.86 (t, J=7.3 Hz, 3 H); MS: 407 (M$^+$+1).

EXAMPLE 21

2-(4-(6-(4-(6-fluoroindolin-1-yl)piperidin-1-yl)pyridazin-3-yl)-1H-pyrazol-1-yl)ethanol (Compound #49)

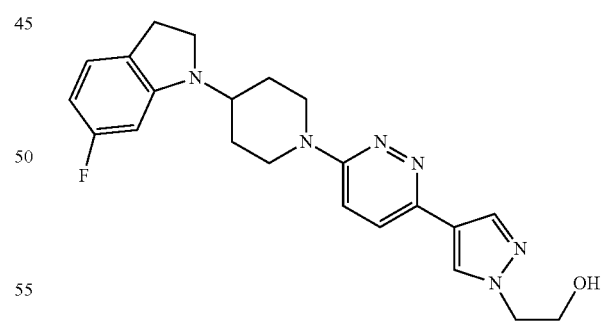

Step 1: Ethyl 2-(4-(6-(4-(6-fluoroindolin-1-yl)piperidin-1-yl)pyridazin-3-yl)-1H-pyrazol-1-yl)acetate Ethyl 2-(4-(6-(4-(6-fluoroindolin-1-yl)piperidin-1-yl)pyridazin-3-yl)-1H-pyrazol-1-yl)acetate was prepared according to the procedure as described in Example 1, Method A, STEP 4, reacting 1-(ethoxycarbonylmethyl)pyrazole-4-boronic acid pinacol ester and 1-(1-(6-chloropyridazin-3-yl)piperidin-4-yl)-6-fluoroindoline.

Step 2: 2-(4-(6-(4-(6-fluoroindolin-1-yl)piperidin-1-yl)pyridazin-3-yl)-1H-pyrazol-1-yl)ethanol To a solution of ethyl 2-(4-(6-(4-(6-fluoroindolin-1-yl)piperidin-1-yl)pyridazin-3-yl)-1H-pyrazol-1-yl)acetate (90 mg, 0.2 mmol) in EtOH (3 mL) was added NaBH$_4$ (76 mg, 2 mmol). The resulting mixture was heated at 65° C. for 2 h and then poured into CH$_2$Cl$_2$/H$_2$O (50 mL/50 mL). The aqueous layer was extracted with CH$_2$Cl$_2$ (50 ml). The combined organic layer was dried (Na$_2$SO$_4$) and filtered. The solvent was removed and the resulting residue was purified by silica gel column using EtOAc to 2% MeOH/EtOAc as the eluent to yield 2-(4-(6-(4-(6-fluoroindolin-1-yl)piperidin-1-yl)pyridazin-3-yl)-1H-pyrazol-1-yl)ethanol.

$^1$H NMR (400 MHz, CHLOROFORM-d) δ=8.03 (s, 1 H), 7.97 (s, 1 H), 7.40 (d, J=9.6 Hz, 1 H), 6.99 (d, J=9.3 Hz, 1 H), 6.88-6.96 (m, 1 H), 6.27 (ddd, J=2.3, 7.7, 9.7 Hz, 1 H), 6.15 (dd, J=2.3, 10.4 Hz, 1 H), 4.48-4.62 (m, 2 H), 4.26-4.36 (m, 2 H), 3.99-4.10 (m, 2 H), 3.53-3.67 (m, 1 H), 3.40 (t, J=8.3 Hz, 2 H), 2.96-3.11 (m, 3 H), 2.90 (t, J=8.3 Hz, 2 H), 1.93 (d, J=12.1 Hz, 2 H), 1.66-1.84 (m, 2 H); MS: 409 (M$^+$+1).

EXAMPLE 22

2-(4-(6-(4-(6-fluoroindolin-1-yl)piperidin-1-yl)pyridazin-3-yl)-1H-pyrazol-1-yl)-N-methylacetamide (Compound #64)

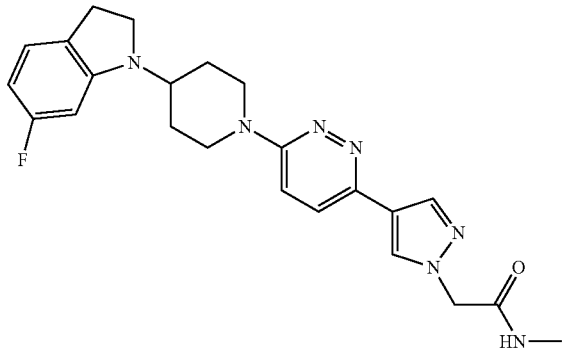 [SMILES: CNC(=O)Cn1cc(-c2ccc(N3CCC(N4CCc5ccc(F)cc54)CC3)nn2)cn1]

In a flask was placed ethyl 2-(4-(6-(4-(6-fluoroindolin-1-yl)piperidin-1-yl)pyridazin-3-yl)-1H-pyrazol-1-yl)acetate (45 mg, 0.1 mmol) and MeOH (2 mL) was added. Then, 40 wt % CH$_3$NH$_{2(aq)}$ (8 mL) was added. The resulting mixture was stirred at room temperature for 30 min and H$_2$O (10 mL) was added. The solid was filtered and washed with H$_2$O (5 mL×3), then dried to yield 2-(4-(6-(4-(6-fluoroindolin-1-yl)piperidin-1-yl)pyridazin-3-yl)-1H-pyrazol-1-yl)-N-methylacetamide as a white solid.

$^1$H NMR (400 MHz, CHLOROFORM-d) δ=8.10 (s, 1 H), 8.00 (s, 1 H), 7.40 (d, J=9.8 Hz, 1 H), 7.00 (d, J=9.4 Hz, 1 H), 6.87-6.97 (m, 1 H), 6.20-6.34 (m, 2 H), 6.15 (dd, J=2.0, 10.6 Hz, 1 H), 4.87 (s, 2 H), 4.57 (d, J=12.9 Hz, 2 H), 3.61 (t, J=11.7 Hz, 1 H), 3.40 (t, J=8.4 Hz, 2 H), 3.06 (t, J=12.1 Hz, 2 H), 2.90 (t, J=8.2 Hz, 2 H), 2.81 (d, J=5.1 Hz, 3 H), 1.94 (d, J=11.7 Hz, 2 H), 1.57-1.85 (m, 2 H); MS: 436 (M$^+$+1).

EXAMPLE 23

1-(1-(6-(1-(2-ethoxyethyl)-1H-pyrazol-4-yl)pyridazin-3-yl)piperidin-4-yl)-6-fluoroindoline (Compound #78)

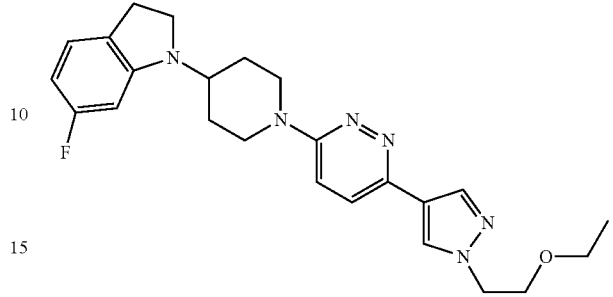

Step 1: 1-(1-(6-(1H-pyrazol-4-yl)pyridazin-3-yl)piperidin-4-yl)-6-fluoroindoline 1-(1-(6-(1H-pyrazol-4-yl)pyridazin-3-yl)piperidin-4-yl)-6-fluoroindoline was prepared according to the procedure described in Example 1, Method A, STEP 4, reacting pyrazole-4-boronic acid pinacol ester and 1-(1-(6-chloropyridazin-3-yl)piperidin-4-yl)-6-fluoroindoline.

Step 2: 1-(1-(6-(1-(2-ethoxyethyl)-1H-pyrazol-4-yl)pyridazin-3-yl)piperidin-4-yl)-6-fluoroindoline To a mixture of 1-(1-(6-(1H-pyrazol-4-yl)pyridazin-3-yl)piperidin-4-yl)-6-fluoroindoline (55 mg, 0.15 mmol, 1.0 equiv) and 2-ethoxyethylbromide (0.17 mL, 1.5 mmol, 10 equiv) was added THF (2 mL) and DMF (0.5 mL). NaH (30 mg, 60% in mineral oil, 0.75 mmol, 5 equiv) was then added. The resulting mixture was stirred at room temperature for 1.5 h and then poured into Et$_2$O/H$_2$O (20 mL/20 mL). The organic layer was washed with brine (20 mL), dried (Na$_2$SO$_4$), and filtered. The solvent was removed and the resulting residue was purified by column using 90-100% EtOAc/hexane as the eluent to yield 1-(1-(6-(1-(2-ethoxyethyl)-1H-pyrazol-4-yl)pyridazin-3-yl)piperidin-4-yl)-6-fluoroindoline.

$^1$H NMR (400 MHz, CHLOROFORM-d) δ=8.07 (s, 1 H), 7.96 (s, 1 H), 7.40 (d, J=9.3 Hz, 1 H), 6.98 (d, J=9.6 Hz, 1 H), 6.89-6.96 (m, 1 H), 6.27 (ddd, J=2.4, 7.8, 9.7 Hz, 1 H), 6.15 (dd, J=2.3, 10.6 Hz, 1 H), 4.55 (dd, J=2.1, 11.2 Hz, 2 H), 4.34 (t, J=5.3 Hz, 2 H), 3.77-3.88 (m, 2 H), 3.53-3.66 (m, 1 H), 3.44-3.53 (m, 2 H), 3.40 (t, J=8.3 Hz, 2 H), 3.04 (td, J=2.4, 12.9 Hz, 2 H), 2.90 (t, J=8.5 Hz, 2 H), 1.93 (d, J=9.9 Hz, 2 H), 1.66-1.82 (m, 2 H), 1.11-1.21 (m, 3 H); MS: 437 (M$^+$+1).

EXAMPLE 24

6-fluoro-1-(1-(6-(5-methylthiophen-2-yl)pyridazin-3-yl)piperidin-4-yl)indoline (Compound #52)

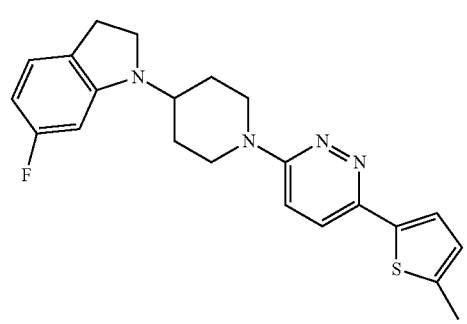 [SMILES: Cc1ccc(-c2ccc(N3CCC(N4CCc5ccc(F)cc54)CC3)nn2)s1]

The title compound was prepared following the procedure as described in Example 1, Method A, STEP 4, reacting 5-methylthiophene-2-boronic acid pinacol ester and 1-(1-(6-chloropyridazin-3-yl)piperidin-4-yl)-6-fluoroindoline.

¹H NMR (400 MHz, CHLOROFORM-d) δ=7.48-7.54 (m, 1 H), 7.24 (d, J=3.5 Hz, 1 H), 6.88-6.99 (m, 2 H), 6.75 (dd, J=1.0, 3.5 Hz, 1 H), 6.27 (ddd, J=2.3, 7.8, 9.6 Hz, 1 H), 6.15 (dd, J=2.3, 10.6 Hz, 1 H), 4.57 (d, J=13.4 Hz, 2 H), 3.53-3.67 (m, 1 H), 3.39 (t, J=8.5 Hz, 2 H), 3.04 (t, J=13.0 Hz, 2 H), 2.83-2.96 (m, 2 H), 2.52 (s, 3 H), 1.92 (d, J=13.4 Hz, 2 H), 1.66-1.81 (m, 2 H); MS: 395 (M⁺+1).

EXAMPLE 25

2-(6-(4-(6-fluoroindolin-1-yl)piperidin-1-yl)pyridazin-3-yl)-5-methylthiazole (Compound #31)

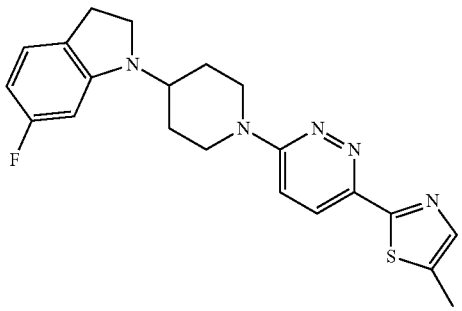 [SMILES: Cc1cnc(-c2ccc(N3CCC(N4CCc5ccc(F)cc54)CC3)nn2)s1]

To a mixture of 1-(1-(6-chloropyridazin-3-yl)piperidin-4-yl)-6-fluoroindoline (100 mg, 0.3 mmol) and Pd(PPh₃)₄ (35 mg, 0.03 mmol) was added 1,4-dioxane (2 mL) and then 3-methyl-2-tributylstannylthiazole (232 mg, 0.6 mmol). The resulting mixture was sealed and heated at 140° C. for 1.5 h. The resulting mixture was then absorbed on silica gel and purified by silica gel column using 40% EtOAc/hexane as the eluent to yield 2-(6-(4-(6-fluoroindolin-1-yl)piperidin-1-yl)pyridazin-3-yl)-5-methylthiazole.

¹H NMR (400 MHz, CHLOROFORM-d) δ=8.01 (d, J=8.0 Hz, 1 H), 7.52 (d, J=1.3 Hz, 1 H), 7.02 (d, J=9.6 Hz, 1 H), 6.90-6.96 (m, 1 H), 6.28 (ddd, J=2.3, 7.7, 9.7 Hz, 1 H), 6.16 (dd, J=2.3, 10.6 Hz, 1 H), 4.60-4.72 (m, 2 H), 3.55-3.71 (m, 1 H), 3.39 (t, J=8.3 Hz, 2 H), 3.09 (td, J=2.1, 12.9 Hz, 2 H), 2.90 (t, J=8.5 Hz, 2 H), 2.53 (d, J=1.0 Hz, 3 H), 1.90-2.00 (m, 2 H), 1.74 (qd, J=4.0, 12.5 Hz, 2 H); MS: 396 (M⁺+1).

EXAMPLE 26

2-(6-(4-(6-fluoroindolin-1-yl)piperidin-1-yl)pyridazin-3-yl)-4-methylthiazole (Compound #29)

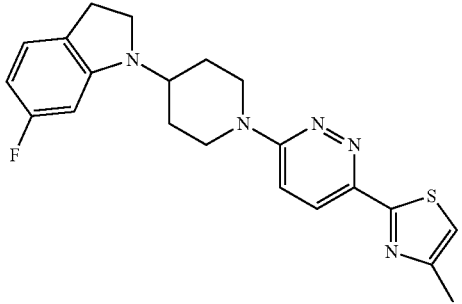 [SMILES: Cc1csc(-c2ccc(N3CCC(N4CCc5ccc(F)cc54)CC3)nn2)n1]

The title compound was prepared following the procedure as described in Example 25, reacting 4-methylthiophene-2-boronic acid pinacol ester and 1-(1-(6-chloropyridazin-3-yl)piperidin-4-yl)-6-fluoroindoline.

¹H NMR (400 MHz, DMSO-d₆) δ=7.95 (d, J=9.6 Hz, 1 H), 7.42 (d, J=9.6 Hz, 1 H), 7.31 (d, J=1.0 Hz, 1 H), 6.94 (t, J=6.9 Hz, 1 H), 6.42 (dd, J=2.3, 11.1 Hz, 1 H), 6.25 (ddd, J=2.5, 7.8, 9.9 Hz, 1 H), 4.62 (d, J=12.9 Hz, 2 H), 3.80 (t, J=11.7 Hz, 1 H), 3.34-3.40 (m, 2 H), 3.10 (t, J=13.0 Hz, 2 H), 2.82 (t, J=8.5 Hz, 2 H), 2.43 (s, 3 H), 1.80 (d, J=12.4 Hz, 2 H), 1.49-1.70 (m, 2 H); MS: 396 (M⁺+1).

EXAMPLE 27

5-(6-(4-(6-fluoroindolin-1-yl)piperidin-1-yl)pyridazin-3-yl)-3-methyl-1,2,4-thiadiazole (Compound #12)

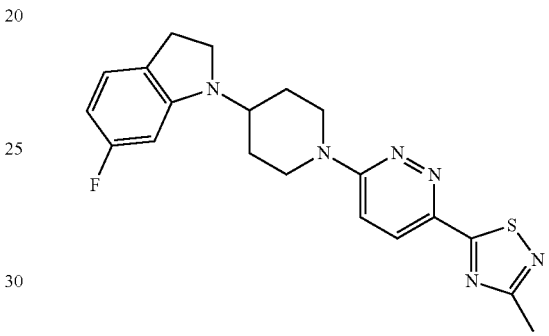

Step 1: 5-(6-chloropyridazin-3-yl)-3-methyl-1,2,4-thiadiazole

To 3-chloro-6-methylpyridazine (5 g, 39 mmol) was added SOCl₂ (29 mL) and the resulting mixture was heated at 73-75° C. for 20 h. The resulting mixture then was concentrated and the residue was dried in vacuo for 30 min. The residue was then dissolved in CH₂Cl₂ (80 mL) and ethanimidamide hydrochloride (3.69 g, 39 mmol) was added. 50% NaOH(aq) (10 mL) was then added dropwise at 0° C. The resulting mixture was allowed to warm to room temperature and stirred for another 1 h. The resulting mixture was then poured into CH₂Cl₂/H₂O (100 mL/200 mL). The aqueous layer was extracted with CH₂Cl₂ (200 mL). The combined organic layer was dried (Na₂SO₄) and filtered. The solvent was removed and the resulting residue was purified by column using EtOAc/CH₂Cl₂/hexane (40/10/50) as the eluent to yield 5-(6-chloropyridazin-3-yl)-3-methyl-1,2,4-thiadiazole.

Step 2: 5-(6-(4-(6-fluoroindolin-1-yl)piperidin-1-yl)pyridazin-3-yl)-3-methyl-1,2,4-thiadiazole 5-(6-(4-(6-Fluoroindolin-1-yl)piperidin-1-yl)pyridazin-3-yl)-3-methyl-1,2,4-thiadiazole was prepared according to the procedure as described in Example 1, Method B, STEP 2, reacting 6-fluoro-1-(piperidin-4-yl)indoline as its corresponding HCl salt and 5-(6-chloropyridazin-3-yl)-3-methyl-1,2,4-thiadiazole, prepared as in STEP 1 above.

¹H NMR (400 MHz, CHLOROFORM-d) δ=7.98 (d, J=9.6 Hz, 1 H), 7.03 (d, J=9.9 Hz, 1 H), 6.89-6.99 (m, 1 H), 6.23-6.35 (m, 1 H), 6.16 (dd, J=2.3, 10.6 Hz, 1 H), 4.72 (d, J=13.9 Hz, 2 H), 3.56-3.73 (m, 1 H), 3.33-3.47 (m, 2H), 3.05-3.21 (m, 2 H), 2.91 (t, J=8.3 Hz, 2 H), 2.73 (s, 3 H), 1.92-2.04 (m, 2 H), 1.74 (qd, J=4.3, 12.5 Hz, 2 H); MS: 397 (M⁺+1).

EXAMPLE 28

6-fluoro-1-(1-(6-(p-tolyl)pyridazin-3-yl)piperidin-4-yl)indoline (Compound #36)

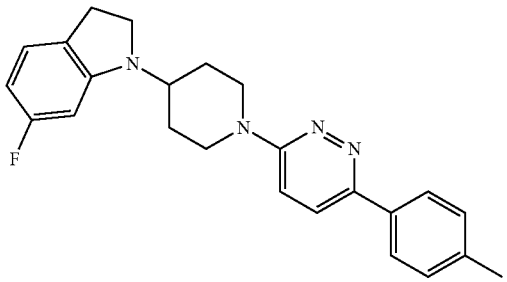 [SMILES: Cc1ccc(-c2ccc(N3CCC(N4CCc5ccc(F)cc54)CC3)nn2)cc1]

The title compound was prepared following the procedure as described in Example 1, Method A, STEP 4, reacting 4-methylphenylboronic acid and 1-(1-(6-chloropyridazin-3-yl)piperidin-4-yl)-6-fluoroindoline.

$^1$H NMR (400 MHz, DMSO-$d_6$) δ=7.82-7.99 (m, 3 H), 7.38 (d, J=9.9 Hz, 1 H), 7.29 (d, J=7.8 Hz, 2 H), 6.87-7.00 (m, 1 H), 6.41 (dd, J=2.3, 11.1 Hz, 1 H), 6.25 (ddd, J=2.5, 7.8, 9.9 Hz, 1 H), 4.56 (br. s., 2 H), 3.68-3.85 (m, 1 H), 3.33-3.41 (m, 2 H), 2.95-3.12 (m, 2 H), 2.82 (t, J=8.5 Hz, 2 H), 2.28-2.40 (m, 3 H), 1.77 (br. s., 2 H), 1.50-1.70 (m, 2 H); MS: 389 (M$^+$+1).

EXAMPLE 29

4-(6-(4-(6-fluoroindolin-1-yl)piperidin-1-yl)pyridazin-3-yl)phenyl)methanol (Compound #51

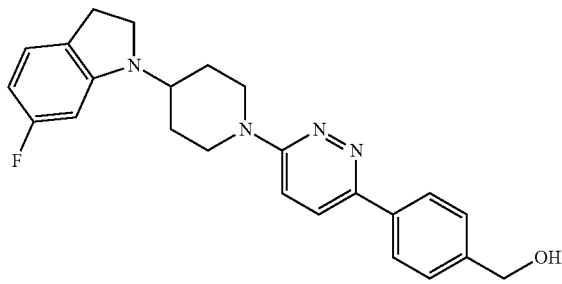 [SMILES: OCc1ccc(-c2ccc(N3CCC(N4CCc5ccc(F)cc54)CC3)nn2)cc1]

The title compound was prepared following the procedure as described in Example 1, Method A, STEP 4, reacting 4-hydroxymethylphenylboronic acid and 1-(1-(6-chloropyridazin-3-yl)piperidin-4-yl)-6-fluoroindoline.

$^1$H NMR (400 MHz, DMSO-$d_6$) δ=8.49 (d, J=9.9 Hz, 1 H), 8.20 (d, J=10.1 Hz, 1 H), 7.94-8.08 (m, J=8.1 Hz, 2 H), 7.45-7.58 (m, J=8.3 Hz, 2 H), 6.89-7.03 (m, 1 H), 6.47 (dd, J=2.1, 11.0 Hz, 1 H), 6.21-6.34 (m, 1 H), 5.76 (s, 1 H), 4.49-4.66 (m, 4 H), 3.78-3.97 (m, 1 H), 3.29-3.45 (m, 4 H), 2.84 (t, J=8.3 Hz, 2 H), 1.61-1.85 (m, 4 H); MS: 405 (M$^+$+1).

EXAMPLE 30

6-fluoro-1-(1-(6-(4-fluorophenyl)pyridazin-3-yl)piperidin-4-yl)indoline (Compound #53)

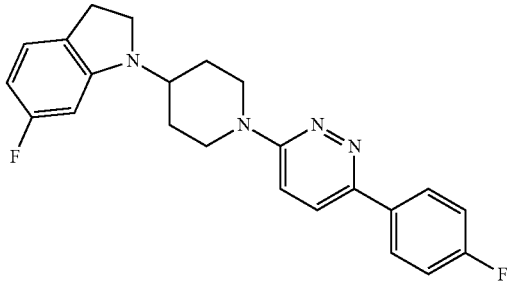 [SMILES: Fc1ccc(-c2ccc(N3CCC(N4CCc5ccc(F)cc54)CC3)nn2)cc1]

The title compound was prepared following the procedure as described in Example 1, Method A, STEP 4, reacting 4-fluorophenylboronic acid and 1-(1-(6-chloropyridazin-3-yl)piperidin-4-yl)-6-fluoroindoline.

$^1$H NMR (400 MHz, DMSO-$d_6$) δ=8.42 (d, J=9.9 Hz, 1 H), 7.99-8.19 (m, 3 H), 7.36-7.48 (m, 2 H), 6.90-7.01 (m, 1 H), 6.46 (dd, J=2.3, 11.1 Hz, 1 H), 6.27 (ddd, J=2.3, 7.8, 9.9 Hz, 1 H), 4.54 (d, J=13.6 Hz, 2 H), 3.76-3.95 (m, 1 H), 3.22-3.45 (m, 4 H), 2.84 (t, J=8.3 Hz, 2 H), 1.81-1.93 (m, 2 H), 1.63-1.81 (m, 2 H); MS: 393 (M$^+$+1).

EXAMPLE 31

6-fluoro-1-(1-(6-(4-(trifluoromethyl)phenyl)pyridazin-3-yl)piperidin-4-yl)indoline (Compound #54)

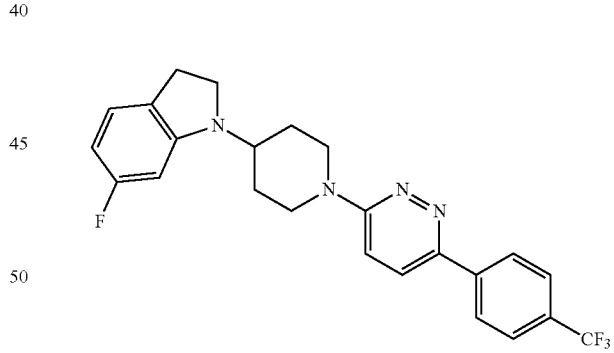

The title compound was prepared following the procedure as described in Example 1, Method A, STEP 4, reacting 4-trifluoromethylphenylboronic acid and 1-(1-(6-chloropyridazin-3-yl)piperidin-4-yl)-6-fluoroindoline.

$^1$H NMR (400 MHz, DMSO-$d_6$) δ=8.41 (d, J=9.6 Hz, 1 H), 8.19-8.33 (m, J=8.3 Hz, 2 H), 8.00 (br. s., 1 H), 7.86-7.96 (m, J=8.3 Hz, 2 H), 6.96 (t, J 10=6.9 Hz, 1 H), 6.46 (dd, J=2.1, 11.0 Hz, 1 H), 6.27 (ddd, J=2.3, 7.9, 9.8 Hz, 1 H), 4.58 (d, J=13.1 Hz, 2 H), 3.87 (t, J=11.7 Hz, 1 H), 3.20-3.43 (m, 4 H), 2.84 (t, J=8.2 Hz, 2 H), 1.80-1.93 (m, 2 H), 1.63-1.80 (m, 2 H); MS: 443 (M$^+$+1).

EXAMPLE 32

4-(6-(4-(6-fluoroindolin-1-yl)piperidin-1-yl)pyridazin-3-yl)benzoic acid (Compound #58)

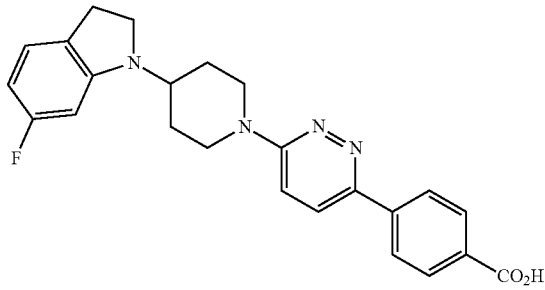 [SMILES: O=C(O)c1ccc(-c2ccc(N3CCC(N4CCc5ccc(F)cc54)CC3)nn2)cc1]

The title compound was prepared following the procedure as described in Example 1, Method A, STEP 4, reacting 4-(t-butylcarbonyl)phenylboronic acid and 1-(1-(6-chloropyridazin-3-yl)piperidin-4-yl)-6-fluoroindoline to yield the corresponding Boc-protected title compound, which was then subjected to TFA de-protection.

$^1$H NMR (400 MHz, DMSO-$d_6$) δ=13.01 (br. s., 1 H), 8.17 (d, J=8.6 Hz, 2 H), 7.95-8.10 (m, 3 H), 7.43 (d, J=9.6 Hz, 1 H), 6.83-7.04 (m, 1 H), 6.42 (dd, J=2.3, 11.1 Hz, 1 H), 6.25 (ddd, J=2.4, 7.9, 9.9 Hz, 1 H), 4.55-4.72 (m, 2 H), 3.69-3.88 (m, 1 H), 3.34-3.43 (m, 2 H), 3.08 (t, J=12.8 Hz, 2 H), 2.82 (t, J=8.3 Hz, 2 H), 1.80 (d, J=10.4 Hz, 2 H), 1.50-1.70 (m, 2 H); MS: 419 (M$^+$+1).

EXAMPLE 33

6-fluoro-1-(1-(6-(6-methylpyridin-3-yl)pyridazin-3-yl)piperidin-4-yl)indoline (Compound #30)

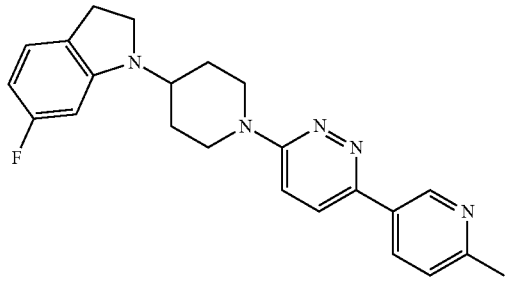 [SMILES: Cc1ccc(-c2ccc(N3CCC(N4CCc5ccc(F)cc54)CC3)nn2)cn1]

The title compound was prepared following the procedure as described in Example 1, Method A, STEP4, reacting 2-methylpyridine-5-boronic acid and 1-(1-(6-chloropyridazin-3-yl)piperidin-4-yl)-6-fluoroindoline.

$^1$H NMR (400 MHz, CHLOROFORM-d) δ=9.04 (d, J=2.0 Hz, 1 H), 8.28 (dd, J=2.3, 8.1 Hz, 1 H), 7.66 (d, J=9.6 Hz, 1 H), 7.28 (d, J=8.0 Hz, 1 H), 7.05 (d, J=9.6 Hz, 1 H), 6.89-6.97 (m, 1 H), 6.24-6.33 (m, 1 H), 6.16 (dd, J=2.1, 10.5 Hz, 1 H), 4.57-4.69 (m, 2 H), 3.56-3.70 (m, 1 H), 3.40 (t, J=8.3 Hz, 2 H), 3.09 (td, J=2.4, 12.9 Hz, 2 H), 2.90 (t, J=8.5 Hz, 2 H), 2.62 (s, 3 H), 1.89-2.02 (m, 2 H), 1.75 (qd, J=3.7, 12.2 Hz, 2 H); MS: 390 (M$^+$+1).

EXAMPLE 34

5-(6-(4-(6-fluoroindolin-1-yl)piperidin-1-yl)pyridazin-3-yl)pyridin-2-yl)methanol (Compound #39)

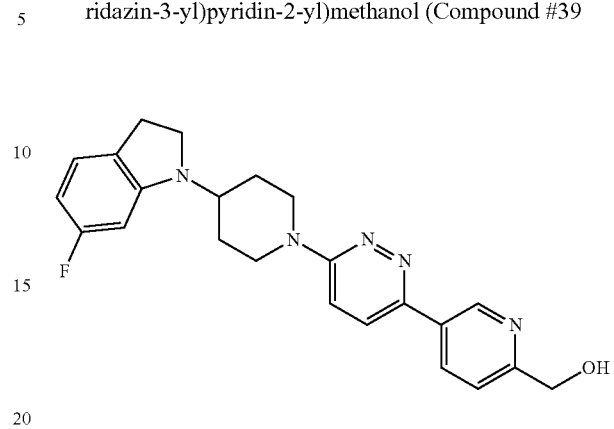

The title compound was prepared following the procedure as described in Example 1, Method A, STEP 4, reacting 2-hydroxymethylpyridine-5-boronic acid and 1-(1-(6-chloropyridazin-3-yl)piperidin-4-yl)-6-fluoroindoline.

$^1$H NMR (400 MHz, DMSO-$d_6$) δ=9.18-9.32 (m, 1 H), 8.84 (br. s., 1 H), 8.40 (d, J=9.9 Hz, 1 H), 7.93 (d, J=8.1 Hz, 2 H), 6.90-7.03 (m, 1 H), 6.46 (dd, J=2.1, 11.0 Hz, 1 H), 6.19-6.34 (m, 1 H), 5.76 (s, 1 H, OH), 4.83 (s, 2 H), 4.62 (d, J=13.1 Hz, 2 H), 3.74-3.94 (m, 1 H), 3.20-3.45 (m, 4 H), 2.84 (t, J=8.3 Hz, 2 H), 1.85 (d, J=11.9 Hz, 2 H), 1.57-1.77 (m, 2 H); MS: 406 (M$^+$+1).

EXAMPLE 35

6-fluoro-1-(1-(6-(6-(trifluoromethyl)pyridin-3-yl)pyridazin-3-yl)piperidin-4-yl)indoline (Compound #76)

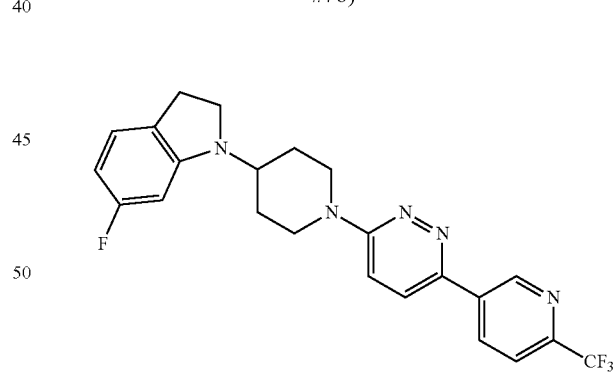

The title compound was prepared following the procedure as described in Example 1, Method A, STEP 4, reacting 2-trifluoromethylpyridine-5-boronic acid and 1-(1-(6-chloropyridazin-3-yl)piperidin-4-yl)-6-fluoroindoline.

$^1$H NMR (400 MHz, DMSO-$d_6$) δ=9.41 (s, 1 H), 8.62-8.76 (m, 1 H), 8.33 (d, J=9.9 Hz, 1 H), 8.07 (d, J=8.3 Hz, 1 H), 7.83 (br. s., 1 H), 6.89-7.03 (m, 1H), 6.45 (dd, J=2.4, 11.0 Hz, 1 H), 6.18-6.33 (m, 1 H), 4.62 (d, J=13.1 Hz, 2H), 3.85 (t, J=11.6 Hz, 1 H), 3.36 (t, J=8.3 Hz, 2 H), 3.23 (t, J=12.5 Hz, 2 H), 2.83 (t, J=8.2 Hz, 2 H), 1.84 (d, J=12.1 Hz, 2 H), 1.68 (q, J=12.5 Hz, 2 H); MS: 444 (M$^+$+1).

EXAMPLE 36

6-fluoro-1-(1-(6-(6-methoxypyridin-3-yl)pyridazin-3-yl)piperidin-4-yl)indoline (Compound #37)

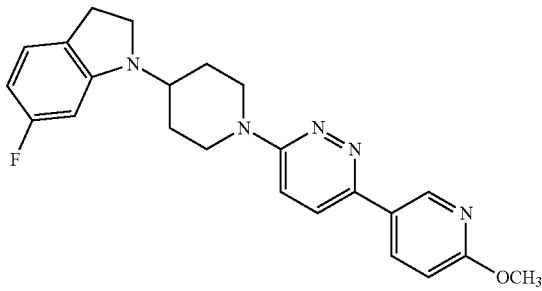 [SMILES: COc1ccc(-c2ccc(N3CCC(N4CCc5ccc(F)cc54)CC3)nn2)cn1]

The title compound was prepared following the procedure as described in Example 1, Method A, STEP 4, reacting 2-methoxypyridine-5-boronic acid and 1-(1-(6-chloropyridazin-3-yl)piperidin-4-yl)-6-fluoroindoline.

$^1$H NMR (400 MHz, DMSO-$d_6$) δ=8.80 (d, J=2.5 Hz, 1 H), 8.35 (dd, J=2.5, 8.6 Hz, 1 H), 7.94 (d, J=9.6 Hz, 1 H), 7.41 (d, J=9.6 Hz, 1 H), 6.89-6.98 (m, 2 H), 6.41 (dd, J=2.3, 11.1 Hz, 1 H), 6.16-6.30 (m, 1 H), 4.58 (d, J=13.1 Hz, 2 H), 3.91 (s, 3 H), 3.67-3.84 (m, 1 H), 3.34-3.42 (m, 2 H), 3.05 (t, J=12.6 Hz, 2 H), 2.82 (t, J=8.5 Hz, 2 H), 1.79 (d, J=14.1 Hz, 2 H), 1.51-1.69 (m, 2H); MS: 406 (M$^+$+1).

EXAMPLE 37

5-(6-(4-(6-fluoroindolin-1-yl)piperidin-1-yl)pyridazin-3-yl)-N,N-dimethylpyridin-2-amine (Compound #44)

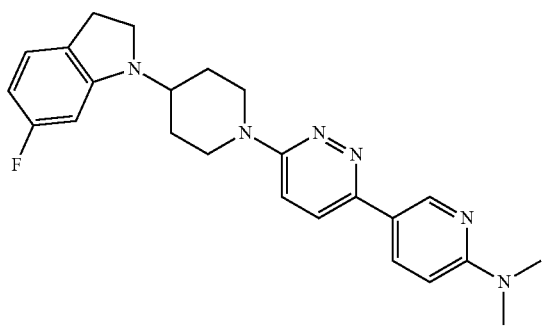 [SMILES: CN(C)c1ccc(-c2ccc(N3CCC(N4CCc5ccc(F)cc54)CC3)nn2)cn1]

The title compound was prepared following the procedure as described in Example 1, Method A, STEP 4, reacting 2-(N,N-dimethylamino)pyridine-5-boronic acid and 1-(1-(6-chloropyridazin-3-yl)piperidin-4-yl)-6-fluoroindoline.

$^1$H NMR (400 MHz, CHLOROFORM-d) δ=8.67 (d, J=2.5 Hz, 1 H), 8.27 (dd, J=2.4, 9.0 Hz, 1 H), 7.58 (d, J=9.6 Hz, 1 H), 7.01 (d, J=9.6 Hz, 1 H), 6.89-6.97 (m, 1 H), 6.63 (d, J=9.1 Hz, 1 H), 6.27 (ddd, J=2.3, 7.8, 9.7 Hz, 1 H), 6.16 (dd, J=2.3, 10.6 Hz, 1 H), 4.58 (d, J=2.0, 11.4 Hz, 2 H), 3.60 (tt, J=3.8, 11.7 Hz, 1 H), 3.40 (t, J=8.5 Hz, 2 H), 3.16 (s, 6 H), 3.05 (td, J=2.4, 12.9 Hz, 2 H), 2.90 (t, J=8.5 Hz, 2 H), 1.88-2.00 (m, 2 H), 1.75 (qd, J=4.3, 12.4 Hz, 2 H); MS: 419 (M$^+$+1).

EXAMPLE 38

5-(6-(4-(6-fluoroindolin-1-yl)piperidin-1-yl)pyridazin-3-yl)-N-methylpicolinamide (Compound #42)

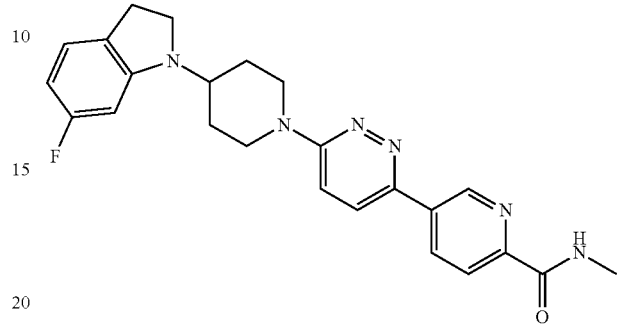

The title compound was prepared following the procedure as described in Example 1, Method A, STEP 4, reacting 2-(N-methylaminocarbonyl)pyridine-5-boronic acid and 1-(1-(6-chloropyridazin-3-yl)piperidin-4-yl)-6-fluoroindoline.

$^1$H NMR (400 MHz, CHLOROFORM-d) δ=9.21 (d, J=1.5 Hz, 1 H), 8.40 (dd, J=2.3, 8.3 Hz, 1 H), 8.28 (d, J=7.6 Hz, 1 H), 8.05 (q, J=5.3 Hz, 1 H), 7.67-7.73 (m, 1 H), 7.07 (d, J=9.6 Hz, 1 H), 6.89-6.98 (m, 1 H), 6.29 (ddd, J=2.3, 7.7, 9.7 Hz, 1 H), 6.16 (dd, J=2.3, 10.4 Hz, 1 H), 4.68 (d, J=13.6 Hz, 2 H), 3.58-3.71 (m, 1 H), 3.40 (t, J=8.5 Hz, 2 H), 3.08-3.17 (m, 2 H), 3.07 (d, J=5.1 Hz, 3 H), 2.91 (t, J=8.5 Hz, 2 H), 1.98 (d, J=12.4 Hz, 2 H), 1.75 (qd, J=3.9, 12.3 Hz, 2 H); MS: 433 (M$^+$+1).

EXAMPLE 39

6-fluoro-1-(1-(6-(1-methyl-1H-pyrazol-4-yl)pyridazin-3-yl)piperidin-4-yl)-1H-indazole (Compound #47)

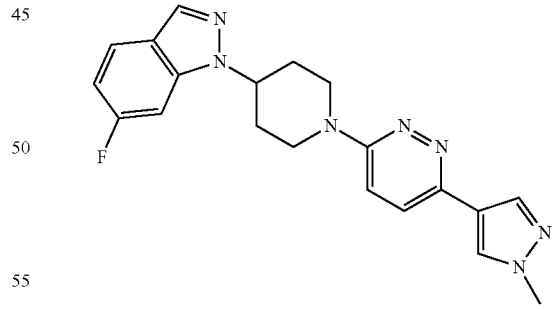

Step 1: tert-butyl 4-(6-fluoro-1H-indazol-1-yl)piperidine-1-carboxylate

To 6-fluoro-1H-indazole (6.46 mmol, 880 mg) in DMF (15 mL) cooled to 0° C. under Ar was added 95% NaH (6.46 mmol, 163 mg). The resulting mixture was stirred for 15 minutes before tert-butyl 4-(tosyloxy)piperidine-1-carboxylate (7.11 mmol, 2.52 g) was added. After an additional 15 minutes at 0° C., the ice bath was removed and the reaction vessel placed in a 110° C. bath for 2.75 hours. After cooling to ambient temperature, the DMF was removed in vacuo and ethyl acetate (100 mL) was added. The organic layer was washed with water and brine, dried (MgSO$_4$), filtered and the solvent removed in vacuo. The resulting residue was purified by SiO$_2$ column chromatography (0-40% EtOAc/hexanes) to yield tert-butyl 4-(6-fluoro-1H-indazol-1-yl)piperidine-1-carboxylate.

Step 2: 6-fluoro-1-(piperidin-4-yl)-1H-indazole

To tert-butyl 4-(6-fluoro-1H-indazol-1-yl)piperidine-1-carboxylate prepared as in STEP 1 above (998 mg, 3.10 mmol) in DCM (20 mL) at 0° C. was added TFA (10 mL). The resulting mixture was then stirred for 1 hour. The solvent was removed in vacuo. To the resulting residue was added 0.5N NaOH (15 mL), followed repeated extraction with CHCl$_3$. The organic layer was dried with MgSO$_4$ and filtered to yield 6-fluoro-1-(piperidin-4-yl)-1H-indazole.

Step 3: 6-fluoro-1-(1-(6-(1-methyl-1H-pyrazol-4-yl)pyridazin-3-yl)piperidin-4-yl)-1H-indazole 6-Fluoro-1-(piperidin-4-yl)-1H-indazole (260 mg, 1.19 mmol), 3-chloro-6-(1-methyl-1H-pyrazol-4-yl)pyridazine (230 mg, 1.19 mmol) and DIEA (269 uL) in DMSO (4 ml) under Ar were heated in a microwave reactor at 200° C. for 1 hour. After removal of most of the DMSO in vacuo, water (10 mL) was added and the aqueous layer extracted several times with CHCl$_3$ (50 mL). The organic layer was washed with brine, dried (MgSO$_4$), decolorized with NORITE, filtered and the solvent removed in vacuo. The resulting residue was purified via ISCO column chromatography (Amine "Redisep" 14 gram column eluded 0-100% EtOAc/hexane over 20 column volumes), then re-crystallized from DCM with heptanes to yield 6-fluoro-1-(1-(6-(1-methyl-1H-pyrazol-4-yl)pyridazin-3-yl)piperidin-4-yl)-1H-indazole.

$^1$H NMR (400 MHz) δ 2.17-2.20 (m, 2H), 2.32-2.43 (dq, 2H), 3.20-.3.25 (t, 2H), 4.00 (s, 3H), 4.58-4.54 (m, 3H), 6.90-6.97 (t, 1H), 7.02-7.06 (d, 1H), 7.40-7.42 (d, 1H), 7.68-7.71 (m, 1H), 7.92 (s, 1H), 7.98 (s, 2H); MS: 378.0 (M$^+$+1); Elemental analysis for C$_{20}$H$_{20}$FN$_7$: Theory(+0.1% water) C, 63.34; H, 5.37; N, 25.85. Found C, 63.17; H, 5.27; N, 25.81

Additional representative compounds of the present invention were similarly prepared according to the procedures as described in the general synthesis schemes and examples, above. Table 3 below, lists measured $^1$HMR and/or MS values for the prepared compounds of formula (I).

TABLE 3

Measured Properties for Prepared Compounds of Formula (I)

| ID No. | Compound Name, Structure and Measured $^1$HNMR and/or MS |
|---|---|
| 1 | 1-(1-(6-(4-methyl-1H-imidazol-1-yl)pyridazin-3-yl)piperidin-4-yl)indoline 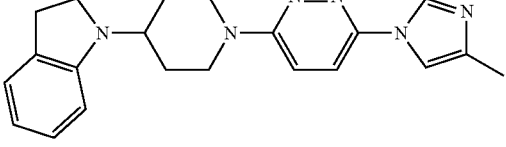 $^1$H NMR (400 MHz, CHLOROFORM-d) δ = 8.15 (s, 1 H), 7.28-7.37 (m, 2 H), 7.04-7.14 (m, 3 H), 6.64 (t, J = 7.3 Hz, 1 H), 6.48 (d, J = 8.3 Hz, 1 H), 4.54 (d, J = 13.4 Hz, 2 H), 3.64-3.76 (m, 1 H), 3.29-3.40 (m, 2 H), 3.02-3.15 (m, 2 H), 2.95 (t, J = 8.3 Hz, 2 H), 2.31 (s, 3 H), 1.97 (d, J = 11.9 Hz, 2 H), 1.75 (qd, J = 4.2, 12.4 Hz, 2 H); MS: 361 (M$^+$ + 1) |
| 5 | 5-fluoro-3-(1-(6-(3-methyl-1,2,4-thiadiazol-5-yl)pyridazin-3-yl)piperidin-4-yl)benzo[d]isoxazole 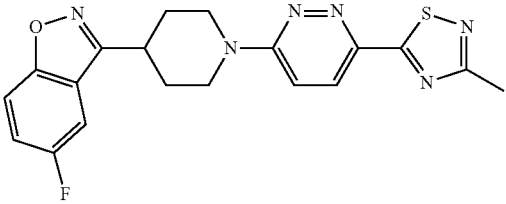 [SMILES: Cc1nsc(-c2ccc(N3CCC(c4noc5ccc(F)cc45)CC3)nn2)n1] $^1$H NMR (400 MHz, CHLOROFORM-d) δ = 8.01 (d, J = 9.6 Hz, 1 H), 7.55 (dd, J = 3.9, 9.0 Hz, 1 H), 7.28-7.37 (m, 2 H), 7.07 (d, J = 9.6 Hz, 1 H), 4.66 (d, J = 13.6 Hz, 2 H), 3.33-3.49 (m, 3 H), 2.73 (s, 3 H), 2.24-2.33 (m, 2 H), 2.06-2.19 (m, 2 H); MS: 397 (M$^+$ + 1) |

TABLE 3-continued

Measured Properties for Prepared Compounds of Formula (I)

| ID No. | Compound Name, Structure and Measured $^1$HNMR and/or MS |
|---|---|
| 6 | 5-(6-(4-(1H-indol-1-yl)piperidin-1-yl)pyridazin-3-yl)-3-methyl-1,2,4-thiadiazole 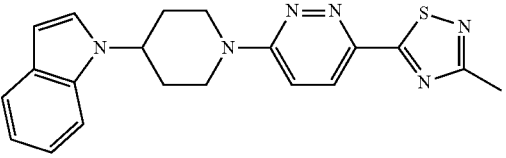 [SMILES: Cc1nsc(-c2ccc(N3CCC(n4ccc5ccccc54)CC3)nn2)n1] $^1$H NMR (400 MHz, CHLOROFORM-d) δ = 8.03 (d, J = 9.6 Hz, 1 H), 7.65 (d, J = 7.8 Hz, 1 H), 7.42 (d, J = 7.8 Hz, 1 H), 7.20-7.25 (m, 1 H), 7.17 (d, J = 3.3 Hz, 1 H), 7.11-7.16 (m, 1 H), 7.09 (d, J = 9.6 Hz, 1 H), 6.54 (d, J = 2.8 Hz, 1 H), 4.80 (d, J = 13.6 Hz, 2 H), 4.61 (tt, J = 3.9, 11.7 Hz, 1 H), 3.22-3.36 (m, 2 H), 2.74 (s, 3 H), 2.25-2.35 (m, 2 H), 2.10 (qd, J = 4.0, 12.5 Hz, 2 H); MS: 377 (M$^+$ + 1) |
| 7 | 5-(6-(4-(indolin-1-yl)piperidin-1-yl)pyridazin-3-yl)-3-methyl-1,2,4-thiadiazole 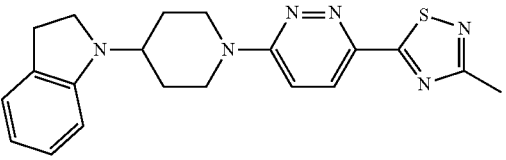 [SMILES: Cc1nsc(-c2ccc(N3CCC(N4CCc5ccccc54)CC3)nn2)n1] $^1$H NMR (400 MHz, CHLOROFORM-d) δ = 7.98 (d, J = 9.6 Hz, 1 H), 7.05-7.11 (m, 2 H), 7.02 (d, J = 9.6 Hz, 1 H), 6.65 (t, J = 7.3 Hz, 1 H), 6.48 (d, J = 8.1 Hz, 1 H), 4.72 (d, J = 13.6 Hz, 2 H), 3.75 (tt, J = 3.8, 11.8 Hz, 1 H), 3.34 (t, J = 8.3 Hz, 2 H), 3.14 (td, J = 2.3, 13.0 Hz, 2 H), 2.95 (t, J = 8.3 Hz, 2 H), 2.72 (s, 3 H), 2.00 (d, J = 10.9 Hz, 2 H), 1.74 (qd, J = 4.3, 12.5 Hz, 2 H); MS: 379 (M$^+$ + 1) |
| 8 | 5-fluoro-3-(1-(6-(pyridin-3-yl)pyridazin-3-yl)piperidin-4-yl)benzo[d]isoxazole 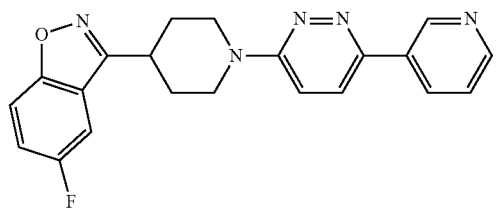 [SMILES: Fc1ccc2onc(C3CCN(c4ccc(-c5cccnc5)nn4)CC3)c2c1] MS: 376 (M$^+$ + 1) |
| 13 | 3-(1-(6-(1-ethyl-1H-pyrazol-4-yl)pyridazin-3-yl)piperidin-4-yl)-5-fluorobenzo[d]isoxazole 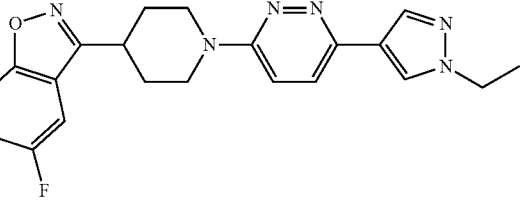 $^1$H NMR (400 MHz, CHLOROFORM-d) δ = 8.02 (s, 1 H), 7.93 (s, 1 H), 7.53 (dd, J = 3.8, 9.1 Hz, 1 H), 7.43 (d, J = 9.6 Hz, 1 H), 7.27-7.38 (m, 2 H), 7.03 (d, J = 9.3 Hz, 1 H), 4.47-4.57 (m, 2 H), 4.24 (q, J = 7.3 Hz, 2 H), 3.37 (tt, J = 3.9, 11.3 Hz, 1 H), 3.18-3.29 (m, 2 H), 2.19-2.27 (m, 3 H), 2.06-2.18 (m, 2 H), 1.55 (t, J = 8 Hz, 3 H); MS: 393 (M$^+$ + 1) |

TABLE 3-continued

Measured Properties for Prepared Compounds of Formula (I)

| ID No. | Compound Name, Structure and Measured ¹HNMR and/or MS |
|---|---|
| 18 | 5-fluoro-3-(1-(6-(5-methyl-1,3,4-oxadiazol-2-yl)pyridazin-3-yl)piperidin-4-yl)benzo[d]isoxazole |

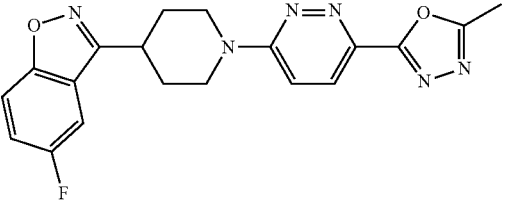 [SMILES: Cc1nnc(-c2ccc(N3CCC(c4noc5ccc(F)cc45)CC3)nn2)o1]

¹H NMR (400 MHz, DMSO-d$_6$) δ = 8.03 (d, J = 9.6 Hz, 1 H), 7.95 (dd, J = 2.5, 8.3 Hz, 1 H), 7.79 (dd, J = 3.8, 9.1 Hz, 1 H), 7.52-7.62 (m, 2H), 4.64 (d, J = 13.4 Hz, 2 H), 3.58 (tt, J = 3.3, 11.5 Hz, 1 H), 3.26-3.39 (m, 2 H), 2.62 (s, 3 H), 2.22 (d, J = 10.9 Hz, 2 H), 1.81-1.97 (m, 2 H); MS: 381 (M$^+$ + 1)

| 19 | (5-(6-(4-(5-fluorobenzo[d]isoxazol-3-yl)piperidin-1-yl)pyridazin-3-yl)-1,3,4-oxadiazol-2-yl)methyl acetate |
|---|---|

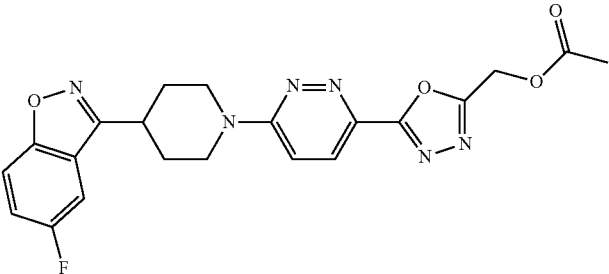 [SMILES: CC(=O)OCc1nnc(-c2ccc(N3CCC(c4noc5ccc(F)cc45)CC3)nn2)o1]

¹H NMR (400 MHz, CHLOROFORM-d) δ = 8.09 (d, J = 9.6 Hz, 1 H), 7.51-7.58 (m, 1 H), 7.28-7.37 (m, 2 H), 7.07 (d, J = 9.6 Hz, 1 H), 5.38 (s, 2 H), 4.67 (d, J = 13.9 Hz, 2 H), 3.34-3.51 (m, 3 H), 2.23-2.33 (m, 2 H), 2.18 (s, 3 H), 2.06-2.17 (m, 2 H); MS: 439 (M$^+$ + 1)

| 20 | (5-(6-(4-(5-fluorobenzo[d]isoxazol-3-yl)piperidin-1-yl)pyridazin-3-yl)-1,3,4-oxadiazol-2-yl)methanol |
|---|---|

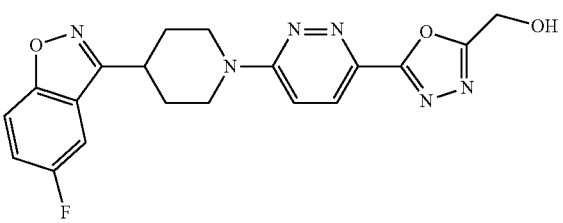 [SMILES: OCc1nnc(-c2ccc(N3CCC(c4noc5ccc(F)cc45)CC3)nn2)o1]

¹H NMR (400 MHz, DMSO-d$_6$) δ = 8.01 (d, J = 9.6 Hz, 1 H), 7.95 (d, J = 7.6 Hz, 1 H), 7.79 (d, J = 5.3 Hz, 1 H), 7.45-7.63 (m, 2 H), 6.01 (t, J = 5.8 Hz, 1 H), 4.75 (d, J = 6.1 Hz, 2 H), 4.66 (d, J = 12.1 Hz, 2 H), 3.57 (br. s., 1 H), 3.23-3.32 (m, 2 H), 2.22 (d, J = 11.9 Hz, 2 H), 1.79-1.98 (m, 2 H); MS: 397 (M$^+$ + 1)

TABLE 3-continued

Measured Properties for Prepared Compounds of Formula (I)

| ID No. | Compound Name, Structure and Measured $^1$HNMR and/or MS |
|---|---|
| 23 | 5-fluoro-3-(1-(6-(4-methylthiazol-2-yl)pyridazin-3-yl)piperidin-4-yl)benzo[d]isoxazoie 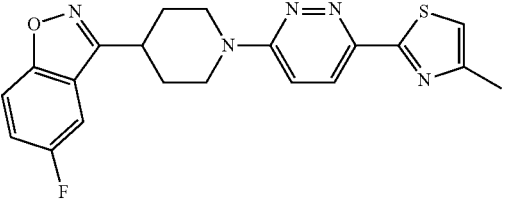 [SMILES: Cc1csc(-c2ccc(N3CCC(c4noc5ccc(F)cc45)CC3)nn2)n1] $^1$H NMR (400 MHz, CHLOROFORM-d) δ = 8.07 (d, J = 9.6 Hz, 1 H), 7.54 (dd, J = 4.0, 9.6 Hz, 1 H), 7.28-7.38 (m, 2 H), 7.06 (d, J = 9.6 Hz, 1 H), 6.93 (d, J = 1.0 Hz, 1 H), 4.62 (dt, J = 3.1, 13.5 Hz, 2 H), 3.41 (tt, J = 4.0, 11.2 Hz, 1 H), 3.27-3.37 (m, 2 H), 2.51 (d, J = 1.0 Hz, 3 H), 2.20-2.30 (m, 2 H), 2.05-2.19 (m, 2 H); MS: 396 (M$^+$ + 1) |
| 24 | 5-fluoro-3-(1-(6-(6-methylpyridin-3-yl)pyridazin-3-yl)piperidin-4-yl)benzo[d]isoxazote 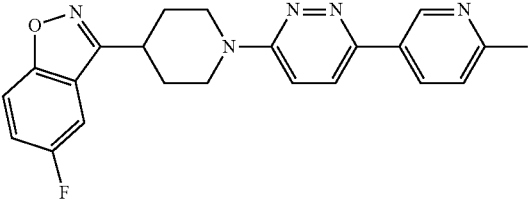 $^1$H NMR (400 MHz, DMSO-d$_6$) δ = 9.09 (d, J = 2.3 Hz, 1 H), 8.29 (dd, J = 2.3, 8.1 Hz, 1 H), 8.01 (d, J = 9.6 Hz, 1 H), 7.93 (dd, J = 2.5, 8.3 Hz, 1 H), 7.79 (dd, J = 3.8, 9.1 Hz, 1 H), 7.55 (td, J = 2.8, 9.1 Hz, 1 H), 7.47 (d, J = 9.6 Hz, 1 H), 7.37 (d, J = 8.1 Hz, 1 H), 4.58 (d, J = 13.6 Hz, 2 H), 3.47-3.61 (m, 1 H), 3.17-3.28 (m, 2 H), 2.53 (s, 3 H), 2.19 (d, J = 10.4 Hz, 2 H), 1.87 (qd, J = 3.8, 12.3 Hz, 2 H); MS: 390 (M$^+$ + 1) |
| 25 | 5-fluoro-3-(1-(6-(2-methylpyridin-4-yl)pyridazin-3-yl)piperidin-4-yl)benzo[d]isoxazole 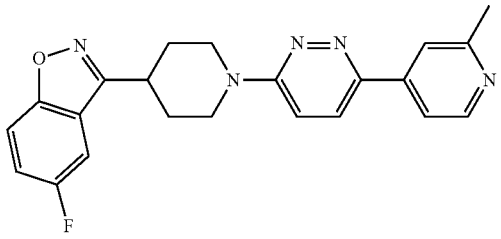 [SMILES: Cc1cc(-c2ccc(N3CCC(c4noc5ccc(F)cc45)CC3)nn2)ccn1] $^1$H NMR (400 MHz, CHLOROFORM-d) δ = 8.60 (d, J = 5.1 Hz, 1 H), 7.83 (s, 1 H), 7.66-7.74 (m, 2 H), 7.51-7.58 (m, 1 H), 7.28-7.38 (m, 2 H), 7.08 (d, J = 9.6 Hz, 1 H), 4.63 (d, J = 13.6 Hz, 2 H), 3.38-3.48 (m, 1 H), 3.34 (ddd, J = 2.7, 11.4, 13.8 Hz, 2 H), 2.65 (s, 3 H), 2.21-2.32 (m, 2 H), 2.08-2.20 (m, 2 H); MS: 390 (M$^+$ + 1) |

TABLE 3-continued

Measured Properties for Prepared Compounds of Formula (I)

| ID No. | Compound Name, Structure and Measured ¹HNMR and/or MS |
|---|---|
| 26 | 3-(1-(6-(1H-pyrazol-4-yl)pyridazin-3-yl)piperidin-4-yl)-5-fluorobenzo[d]isoxazole |

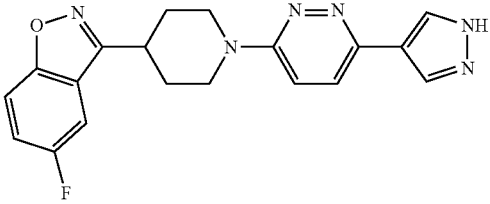 [SMILES: Fc1ccc2onc(C3CCN(c4ccc(-c5cn[nH]c5)nn4)CC3)c2c1]

¹H NMR (400 MHz, CHLOROFORM-d) δ = 10.23 (br s, 1 H), 8.14 (s, 2 H), 7.53 (dd, J = 3.9, 9.0 Hz, 1 H), 7.47 (d, J = 9.3 Hz, 1 H), 7.27-7.38 (m, 2 H), 7.04 (d, J = 9.3 Hz, 1 H), 4.48-4.59 (m, 2 H), 3.38 (tt, J = 4.0, 11.2 Hz, 1 H), 3.19-3.31 (m, 2 H), 2.19-2.29 (m, 2 H), 2.05-2.19 (m, 2 H); MS: 365 (M⁺ + 1)

| 27 | 5-fluoro-3-(1-(6-(4-methylthiophen-2-yl)pyridazin-3-yl)piperidin-4-yl)benzo[d]isoxazole |

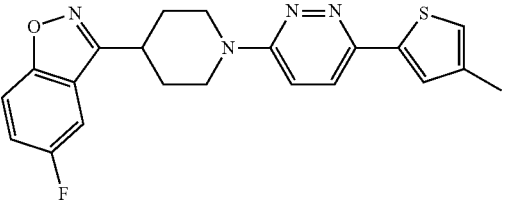 [SMILES: Cc1csc(-c2ccc(N3CCC(c4noc5ccc(F)cc45)CC3)nn2)c1]

¹H NMR (400 MHz, CHLOROFORM-d) δ = 7.51-7.58 (m, 2 H), 7.27-7.37 (m, 3 H), 7.01 (d, J = 9.3 Hz, 1 H), 6.94 (s, 1 H), 4.55 (dt, J = 3.1, 13.5 Hz, 2 H), 3.38 (tt, J = 3.9, 11.4 Hz, 1 H), 3.20-3.31 (m, 2 H), 2.30 (s, 3 H), 2.19-2.27 (m, 2 H), 2.05-2.18 (m, 2 H); MS: 395 (M⁺ + 1)

| 28 | 5-fluoro-3-(1-(6-(5-methylthiazol-2-yl)pyridazin-3-yl)piperidin-4-yl)benzo[d]isoxazole |

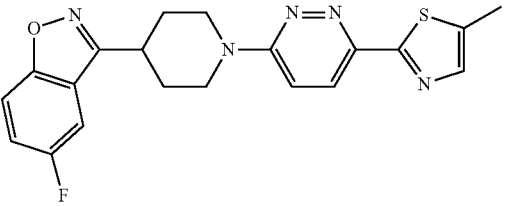 [SMILES: Cc1cnc(-c2ccc(N3CCC(c4noc5ccc(F)cc45)CC3)nn2)s1]

¹H NMR (400 MHz, CHLOROFORM-d) δ = 8.04 (d, J = 9.6 Hz, 1 H), 7.50-7.57 (m, 2 H), 7.28-7.38 (m, 2 H), 7.06 (d, J = 9.6 Hz, 1 H), 4.61 (dt, J = 3.2, 13.8 Hz, 2 H), 3.41 (tt, J = 4.0, 11.3 Hz, 1 H), 3.26-3.36 (m, 2 H), 2.53 (d, J = 1.3 Hz, 3 H), 2.20-2.29 (m, 2 H), 2.05-2.19 (m, 2 H); MS: 396 (M⁺ + 1)

TABLE 3-continued

Measured Properties for Prepared Compounds of Formula (I)

| ID No. | Compound Name, Structure and Measured ¹HNMR and/or MS |
|---|---|
| 32 | 5-fluoro-3-(1-(6-(p-tolyl)pyridazin-3-yl)piperidin-4-yl)benzo[d]isoxazole |

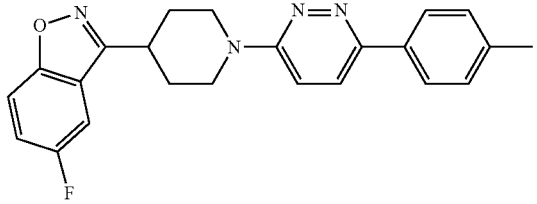 [SMILES: Cc1ccc(-c2ccc(N3CCC(c4noc5ccc(F)cc45)CC3)nn2)cc1]

¹H NMR (400 MHz, CHLOROFORM-d) δ = 7.92 (d, J = 8.3 Hz, 2 H), 7.67 (d, J = 9.6 Hz, 1 H), 7.53 (dd, J = 3.7, 9.0 Hz, 1 H), 7.27-7.38 (m, 4 H), 7.07 (d, J = 9.6 Hz, 1 H), 4.58 (d, J = 13.4 Hz, 2 H), 3.39 (tt, J = 3.8, 11.4 Hz, 1 H), 3.23-3.32 (m, 2 H), 2.41 (s, 3 H), 2.20-2.29 (m, 2 H), 2.07-2.20 (m, 2 H); MS: 389 (M⁺ + 1)

| 33 | 5-fluoro-3-(1-(6-(6-methoxypyridin-3-yl)pyridazin-3-yl)piperidin-4-yl)benzo[d]isoxazole |
|---|---|

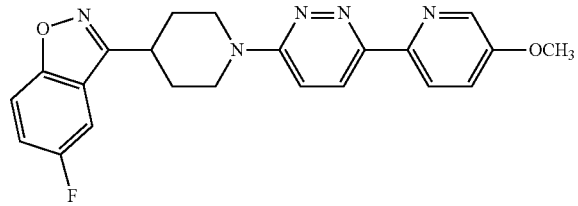 [SMILES: COc1ccc(-c2ccc(N3CCC(c4noc5ccc(F)cc45)CC3)nn2)nc1]

¹H NMR (400 MHz, DMSO-d₆) δ = 8.89 (d, J = 2.3 Hz, 1 H), 8.51 (d, J = 10.1 Hz, 1 H), 8.35 (dd, J = 2.5, 8.8 Hz, 1 H), 8.23 (d, J = 10.1 Hz, 1 H), 8.01 (dd, J = 2.3, 8.3 Hz, 1 H), 7.81 (dd, J = 3.9, 9.0 Hz, 1 H), 7.52-7.61 (m, 1 H), 7.05 (d, J = 8.6 Hz, 1 H), 4.55 (d, J = 13.1 Hz, 2 H), 3.95 (s, 3 H), 3.65 (t, J = 11.2 Hz, 1 H), 3.52 (t, J = 12.3 Hz, 2 H), 2.24 (d, J = 12.4 Hz, 2 H), 1.94-2.11 (m, 2 H); MS: 406 (M⁺ + 1)

| 34 | 5-fluoro-3-(1-(6-(2-methoxypyrimidin-5-yl)pyridazin-3-yl)piperidin-4-yl)benzo[d]isoxazole |
|---|---|

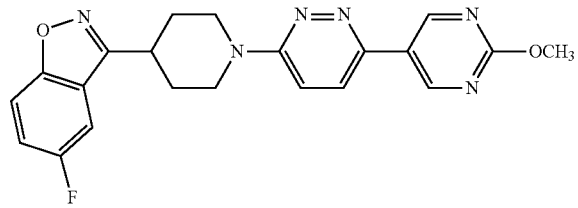 [SMILES: COc1ncc(-c2ccc(N3CCC(c4noc5ccc(F)cc45)CC3)nn2)cn1]

¹H NMR (400 MHz, DMSO-d₆) δ = 9.24 (s, 2 H), 8.41 (d, J = 10.1 Hz, 1 H), 8.09 (d, J = 9.1 Hz, 1 H), 7.99 (dd, J = 2.5, 8.3 Hz, 1 H), 7.80 (dd, J = 3.8, 9.1 Hz, 1 H), 7.57 (td, J = 2.5, 9.1 Hz, 1 H), 4.55 (d, J = 13.6 Hz, 2 H), 4.02 (s, 3 H), 3.55-3.69 (m, 1 H), 3.40-3.52 (m, 2 H), 2.24 (d, J = 10.9 Hz, 2 H), 1.90-2.07 (m, 2 H); MS: 407 (M⁺ + 1)

TABLE 3-continued

Measured Properties for Prepared Compounds of Formula (I)

| ID No. | Compound Name, Structure and Measured ¹HNMR and/or MS |
|---|---|
| 35 | (5-(6-(4-(5-fluorobenzo[d]isoxazol-3-yl)piperidin-1-yl)pyridazin-3-yl)pyridin-2-yl)methanol |

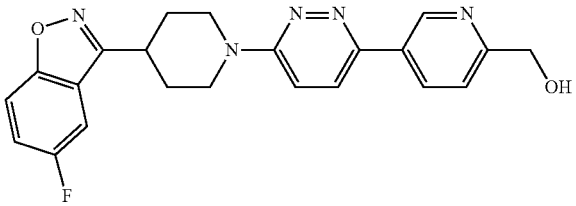 [SMILES: OCc1ccc(-c2ccc(N3CCC(c4noc5ccc(F)cc45)CC3)nn2)cn1]

¹H NMR (400 MHz, DMSO-d$_6$) δ = 9.17-9.28 (m, 1 H), 8.77 (d, J = 6.6 Hz, 1 H), 8.38 (d, J = 9.9 Hz, 1 H), 7.97 (dd, J = 2.3, 8.3 Hz, 1 H), 7.87 (d, J = 8.8 Hz, 2 H), 7.80 (dd, J = 3.9, 9.2 Hz, 1 H), 7.52-7.62 (m, 1 H), 4.79 (s, 2 H), 4.59 (d, J = 13.1 Hz, 2 H), 3.51-3.68 (m, 1 H), 3.33-3.48 (m, 3 H), 2.23 (d, J = 11.6 Hz, 2 H), 1.90-2.00 (m, 2 H); MS: 406 (M$^+$ + 1)

| | |
|---|---|
| 38 | 6-fluoro-1-(1-(6-(2-methoxypyrimidin-5-yl)pyridazin-3-yl)piperidin-4-yl)indoline |

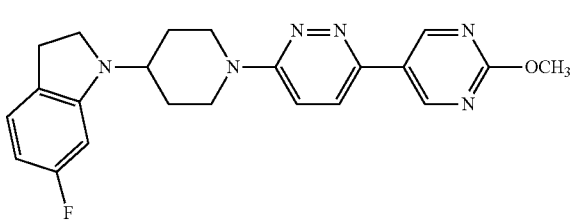 [SMILES: COc1ncc(-c2ccc(N3CCC(N4CCc5ccc(F)cc54)CC3)nn2)cn1]

¹H NMR (400 MHz, DMSO-d$_6$) δ = 9.21 (s, 2 H), 8.00 (d, J = 9.6 Hz, 1 H), 7.46 (d, J = 9.6 Hz, 1 H), 6.89-6.98 (m, 1 H), 6.42 (dd, J = 2.3, 11.1 Hz, 1 H), 6.25 (ddd, J = 2.3, 7.8, 9.9 Hz, 1 H), 4.60 (d, J = 12.9 Hz, 2 H), 3.98 (s, 3 H), 3.72-3.85 (m, 1 H), 3.33-3.39 (m, 2 H), 3.07 (t, J = 11.9 Hz, 2 H), 2.82 (t, J = 8.3 Hz, 2 H), 1.79 (d, J = 12.1 Hz, 2 H), 1.50-1.67 (m, 2 H); MS: 407 (M$^+$ + 1)

| | |
|---|---|
| 40 | 1-(1-(6-(1-methyl-1H-pyrazol-4-yl)pyridazin-3-yl)piperidin-4-yl)-1H-indazole |

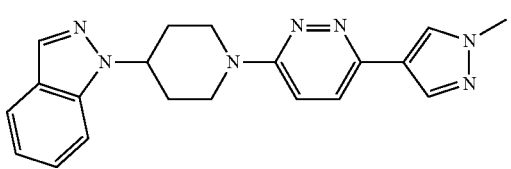 [SMILES: Cn1cc(-c2ccc(N3CCC(n4ncc5ccccc54)CC3)nn2)cn1]

¹H NMR(400 MHz, CHLOROFORM-d) δ 8.00 (s, 1H), 7.99 (s, 1H), 7.95 (s, 1H), 7.75 (d, 1H), 7.38-7.52 (m, 3H), 7.15-7.19 (m, 1H), 7.02 (d, 1H), 4.69-4.79 (m, 1H), 4.58-4.62 (m, 2H), 3.97 (s, 3H), 3.20-3.29 (t, 2H), 2.37-2.48 (dq, 2H), 2.10-2.20 (m, 2H); MS: 360.0 (M$^+$ + 1)

| | |
|---|---|
| 41 | 1-(1-(6-(1-methyl-1H-pyrazol-4-yl)pyridazin-3-yl)piperidin-4-yl)-2-(trifluoromethyl)-1H-benzo[d]imidazole |

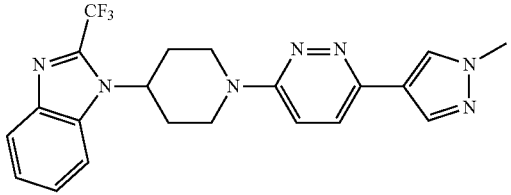 [SMILES: Cn1cc(-c2ccc(N3CCC(n4c(C(F)(F)F)nc5ccccc54)CC3)nn2)cn1]

¹H NMR(400 MHz, CHLOROFORM-d) δ 8.01 (s, 1H), 7.95 (s, 1H), 7.90 (m, 1H), 7.48-7.53 (m, 2H), 7.30-7.37 (m, 2H), 7.06 (d, 1H), 4.62-4.81 (m, 3H), 4.00 (s, 3H), 3.11-3.21 (t, 2H), 2.60-2.76 (dq, 2H), 2.08-2.17 (m, 2H),; MS: 428 (M$^+$ + 1)

TABLE 3-continued

Measured Properties for Prepared Compounds of Formula (I)

| ID No. | Compound Name, Structure and Measured $^1$HNMR and/or MS |
|---|---|
| 45 | N-(5-(6-(4-(6-fluoroindolin-1-yl)piperidin-1-yl)pyridazin-3-yl)pyridin-2-yl)acetamide |

$^1$H NMR (400MHz, CHLOROFORM-d) δ = 8.91 (t, J = 1.5 Hz, 1 H), 8.31 (d, J = 2.3 Hz, 2 H), 8.00 (s, 1 H), 7.63 (d, J = 9.6 Hz, 1 H), 7.05 (d, J = 9.6 Hz, 1 H), 6.93 (dd, J = 5.8, 7.8 Hz, 1 H), 6.28 (ddd, J = 2.3, 7.8, 9.7 Hz, 1 H), 6.16 (dd, J = 2.0, 10.6 Hz, 1 H), 4.64 (d, J = 13.4 Hz, 2 H), 3.63 (tt, J = 3.9, 11.8 Hz, 1 H), 3.40 (t, J = 8.3 Hz, 2 H), 3.03-3.15 (m, 2 H), 2.90 (t, J = 8.3 Hz, 2 H), 2.24 (s, 3 H), 1.90-2.01 (m, 2 H), 1.75 (qd, J = 4.4, 12.3 Hz, 2 H); MS: 433 (M$^+$ + 1)

| 48 | 1-(1-(6-(1-methyl-1H-pyrazol-4-yl)pyridazin-3-yl)piperidin-4-yl)-1H-benzo[d][1,2,3]triazoie |

$^1$H NMR(400 MHz, CHLOROFORM-d) δ 8.10 (d, 1H), 7.99 (s, 1H), 7.97 (s, 1H), 7.59 (m, 1H), 7.48-7.52 (m, 2H), 7.38-7.41 (m, 1H), 7.08 (d, 1H), 4.95-5.03 (m, 1H), 4.60-4.63 (m, 2H), 3.99 (s, 3H), 3.29-.3.38 (t, 2H), 2.49-2.59 (dq, 2H), 2.25-2.28 (m, 2H); MS: 361 (M$^+$ + 1)

| 50 | ethyl 2-(4-(6-(4-(6-fluoroindolin-1-yl)piperidin-1-yl)pyridazin-3-yl)-1H-pyrazol-1-yl)acetate |

MS: 451 (M$^+$ + 1)

| 55 | tert-butyl 4-(6-(4-(6-fluoroindolin-1-yl)piperidin-1-yl)pyridazin-3-yl)benzoate |

$^1$H NMR (400 MHz, CHLOROFORM-d) δ = 8.07 (s, 4 H), 7.70 (d, J = 9.6 Hz, 1 H), 7.04 (d, J = 9.6 Hz, 1 H), 6.88-6.97 (m, 1 H), 6.28 (ddd, J = 2.4, 7.8, 9.7 Hz, 1 H), 6.16 (dd, J = 2.0, 10.4 Hz, 1 H), 4.66 (d, J = 13.9 Hz, 2 H), 3.57-3.69 (m, 1 H), 3.34-3.45 (m, 2 H), 3.03-3.16 (m, 2 H), 2.90 (t, J = 8.6 Hz, 2 H), 1.91-2.01 (m, 2 H), 1.69-1.84 (m, 2 H), 1.62 (s, 9 H); MS: 475 (M$^+$ + 1)

TABLE 3-continued

Measured Properties for Prepared Compounds of Formula (I)

| ID No. | Compound Name, Structure and Measured ¹HNMR and/or MS |
|---|---|

56   4-(6-(4-(6-fluoroindolin-1-yl)piperidin-1-yl)pyridazin-3-yl)benzamide

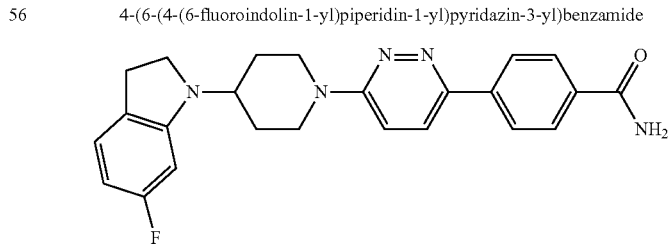

¹H NMR (400 MHz, DMSO-d$_6$) δ = 8.42 (d, J = 9.9 Hz, 1 H), 8.13 (d, J = 8.6 Hz, 2 H), 8.04 (d, J = 8.3 Hz, 2 H), 7.52 (br. s., 1 H), 6.96 (t, J = 6.9 Hz, 1 H), 6.46 (dd, J = 2.4, 11.0 Hz, 1 H), 6.21-6.31 (m, 1 H), 4.56 (d, J = 13.1 Hz, 2 H), 3.78-3.93 (m, 1 H), 3.31-3.43 (m, 4 H), 2.84 (t, J = 8.5 Hz, 2 H), 1.80-1.91 (m, 2 H), 1.64-1.80 (m, 2 H) (NH$_2$ not shown); MS: 418 (M$^+$ + 1)

61   4-chloro-1-(1-(6-(1-methyl-1H-pyrazol-4-yl)pyridazin-3-yl)piperidin-4-yl)-1H-indazole

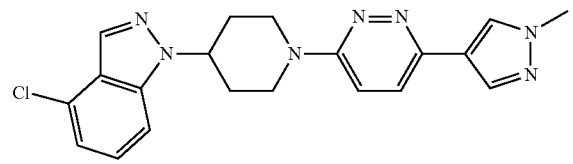 [SMILES: Cn1cc(-c2ccc(N3CCC(n4ncc5c(Cl)cccc54)CC3)nn2)cn1]

¹H NMR (400 MHz, CHLOROFORM-d) δ = 7.98 (s, 1 H), 7.97 (s, 1 H), 7.65 (d, 1 H), 7.42-7.45 (m, 3 H), 7.20-7.24 (m, 1 H), 7.02 (d, 1 H), 3.99 (s, 3 H), 3.18-3.25 (t, 2 H), 2.36-2.43 (dq, 2 H), 2.15-2.19 (m, 2 H), 4.58-4.67 (m, 2 H); MS: 394 (M$^+$ + 1)

67   4-chloro-1-(1-(6-(1-methyl-1H-pyrazol-4-yl)pyridazin-3-yl)piperidin-4-yl)indoline

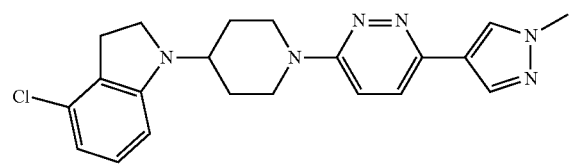 [SMILES: Cn1cc(-c2ccc(N3CCC(N4CCc5c(Cl)cccc54)CC3)nn2)cn1]

MS: 395 (M$^+$ + 1)

68   4,6-dichloro-1-(1-(6-(1-methyl-1H-pyrazol-4-yl)pyridazin-3-yl)piperidin-4-yl)indoline

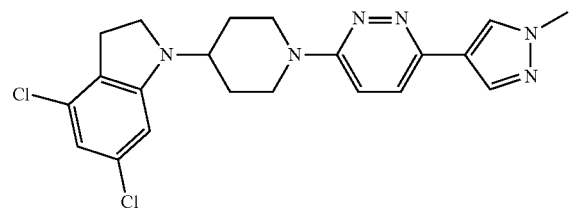 [SMILES: Cn1cc(-c2ccc(N3CCC(N4CCc5c(Cl)cc(Cl)cc54)CC3)nn2)cn1]

¹H NMR (400 MHz, DMSO-d$_6$) δ = 8.51 (s, 1 H), 8.20 (d, J = 9.6 Hz, 1 H), 8.17 (s, 1 H), 8.07 (d, J = 10.1 Hz, 1 H), 6.57-6.64 (m, 2 H), 4.46 (d, J = 13.4 Hz, 2 H), 3.93 (s, 3 H), 3.84-3.91 (m, 1 H), 3.45 (t, J = 8.6 Hz, 2 H), 3.25 (t, J = 12.3 Hz, 2 H), 2.90 (t, J = 8.6 Hz, 2 H), 1.76-1.86 (m, 2 H), 1.70 (qd, J = 3.3, 12.1 Hz, 2 H); MS: 430 (M$^+$ + 1)

TABLE 3-continued

Measured Properties for Prepared Compounds of Formula (I)

| ID No. | Compound Name, Structure and Measured $^1$HNMR and/or MS |
|---|---|
| 69 | 2-(4-(6-(4-(6-fluoroindolin-1-yl)piperidin-1-yl)pyridazin-3-yl)-1H-pyrazol-1-yl)acetamide |

$^1$H NMR (400 MHz, CHLOROFORM-d) δ = 8.10 (s, 1 H), 8.03 (s, 1 H), 7.40 (d, J = 9.3 Hz, 1 H), 7.00 (d, J = 9.6 Hz, 1 H), 6.93 (d, J = 13.6 Hz, 1 H), 6.20-6.35 (m, 2 H), 6.15 (d, J = 10.6 Hz, 1 H), 5.56 (br. s., 1 H), 4.88 (s, 2 H), 4.57 (d, J = 13.4 Hz, 2 H), 3.53-3.68 (m, 1 H), 3.40 (t, J = 8.3 Hz, 2 H), 3.06 (t, J = 12.6 Hz, 2 H), 2.90 (t, J = 8.2 Hz, 2 H), 1.94 (d, J = 11.4 Hz, 2 H), 1.68-1.83 (m, 2 H); MS: 422 (M$^+$ + 1)

| 70 | 4-fluoro-1-(1-(6-(1-methyl-1H-pyrazol-4-yl)pyridazin-3-yl)piperidin-4-yl)-1H-indazole |

$^1$H NMR(400 MHz, CHLOROFORM-d) δ = 8.06 (s, 1H), 7.97 (s, 1 H), 7.92 (s, 1 H), 7.42 (d, 1 H), 7.24-7.34 (m, 2 H), 7.04 (d, 1 H), 6.77-6.81 (m, 1 H), 4.67-4.75 (m, 1 H), 4.59-4.63 (m, 2 H), 3.99 (s, 3 H), 3.21-.3.28 (t, 2 H), 2.35-2.45 (dq, 2 H), 2.16-2.19 (m, 2 H); MS: 378 (M$^+$ + 1)

| 71 | 4-(2-(4-(6-(4-(6-fluoroindolin-1-yl)piperidin-1-yl)pyridazin-3-yl)-1H-pyrazol-1-yl)ethyl)morpholine |

$^1$H NMR (400 MHz, CHLOROFORM-d) δ = 8.07 (s, 1 H), 7.91 (s, 1 H), 7.40 (d, J = 9.6 Hz, 1 H), 6.99 (d, J = 9.6 Hz, 1 H), 6.89-6.96 (m, 1 H), 6.27 (ddd, J = 2.3, 7.9, 9.8 Hz, 1 H), 6.15 (dd, J = 2.3, 10.6 Hz, 1 H), 4.55 (d, J = 13.6 Hz, 2 H), 4.30 (t, J = 6.4 Hz, 2 H), 3.66-3.74 (m, 4 H), 3.60 (tt, J = 3.7, 11.7 Hz, 1 H), 3.40 (t, J = 8.5 Hz, 2 H), 2.99-3.10 (m, 2 H), 2.82-2.94 (m, 4 H), 2.47-2.54 (m, 4 H), 1.93 (d, J = 11.6 Hz, 2 H), 1.67-1.82 (m, 2 H); MS: 478 (M$^+$ + 1)

TABLE 3-continued

Measured Properties for Prepared Compounds of Formula (I)

| ID No. | Compound Name, Structure and Measured $^1$HNMR and/or MS |
|---|---|
| 73 | 5-fluoro-1-(1-(6-(1-methyl-1H-pyrazol-4-yl)pyridazin-3-yl)piperidin-4-yl)-1H-indazole |

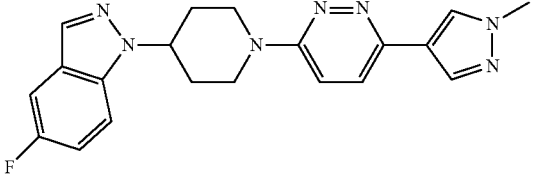 [SMILES: Cn1cc(-c2ccc(N3CCC(n4ncc5cc(F)ccc54)CC3)nn2)cn1]

$^1$H NMR (400 MHz, CHLOROFORM-d) δ = 7.98 (s, 2 H), 7.92 (s, 1 H), 7.40-7.45 (m, 2 H), 7.34-7.38 (m, 1 H), 7.14-7.20 (t, 1 H), 7.02-7.06 (d, 1 H), 4.66-4.72 (m, 1 H), 4.58-4.62 (m, 2 H), 3.97 (s, 3 H), 3.20-.3.27 (t, 2 H), 2.34-2.44 (dq, 2 H), 2.17-2.20 (m, 2 H); MS: 378 (M$^+$ + 1)

| 74 | 6-chloro-1-(1-(6-(1-methyl-1H-pyrazol-4-yl)pyridazin-3-yl)piperidin-4-yl)-1H-indazole |
|---|---|

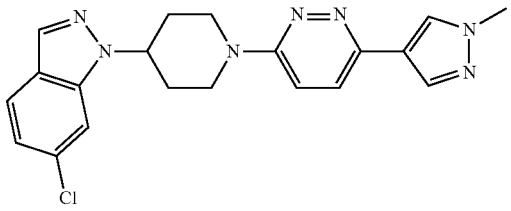 [SMILES: Cn1cc(-c2ccc(N3CCC(n4ncc5ccc(Cl)cc54)CC3)nn2)cn1]

$^1$H NMR (400 MHz, CHLOROFORM-d) δ = 7.97 (s, 2 H), 7.92 (s, 1 H), 7.65 (d, 1 H), 7.50 (s, 1 H), 7.42 (d, 1 H), 7.13 (d, 1 H), 7.04 (d, 1 H), 4.59-4.65 (m, 3 H), 3.98 (s, 3 H), 3.20-.3.27 (t, 2 H), 2.37-2.41 (dq, 2 H), 2.15-2.18 (m, 2 H); MS: 394 (M$^+$ + 1)

| 75 | 3-(1-(6-(1-(2-ethoxyethyl)-1H-pyrazol-4-yl)pyridazin-3-yl)piperidin-4-yl)-5-fluorobenzo[d]isoxazole |
|---|---|

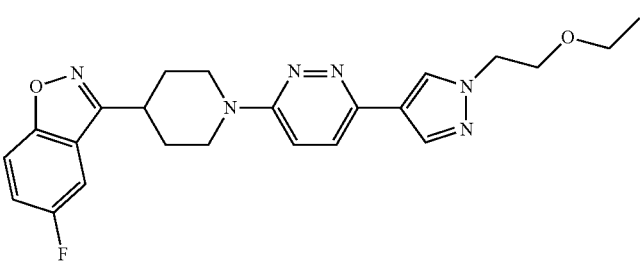 [SMILES: CCOCCn1cc(-c2ccc(N3CCC(c4noc5ccc(F)cc45)CC3)nn2)cn1]

$^1$H NMR (400 MHz, CHLOROFORM-d) δ = 8.08 (s, 1 H), 7.97 (s, 1 H), 7.53 (dd, J = 3.8, 9.1 Hz, 1 H), 7.43 (d, J = 9.6 Hz, 1 H), 7.29-7.39 (m, 2 H), 7.03 (d, J = 9.6 Hz, 1 H), 4.52 (d, J = 13.1 Hz, 2 H), 4.35 (t, J = 5.3 Hz, 2 H), 3.79-3.88 (m, 2 H), 3.49 (q, J = 7.0 Hz, 2 H), 3.31-3.44 (m, 1 H), 3.17-3.31 (m, 2 H), 2.19-2.29 (m, 2 H), 2.11-2.19 (m, 2 H), 1.17 (t, J = 6.9 Hz, 3 H); MS: 437 (M$^+$ + 1)

TABLE 3-continued

Measured Properties for Prepared Compounds of Formula (I)

| ID No. | Compound Name, Structure and Measured ¹HNMR and/or MS |
|---|---|
| 77 | 1-(1-(6-(1H-pyrazol-4-yl)pyridazin-3-yl)piperidin-4-yl)-6-fluoroindoline |

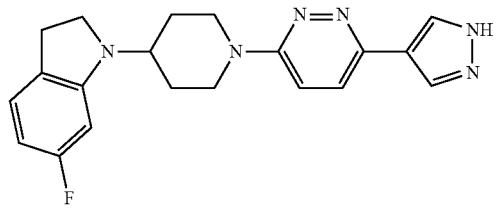 [SMILES: Fc1ccc2c(c1)N(C1CCN(c3ccc(-c4cn[nH]c4)nn3)CC1)CC2]

$^1$H NMR (400 MHz, CHLOROFORM-d) δ = 8.13 (s, 2 H), 7.44 (d, J = 9.3 Hz, 1 H), 7.00 (d, J = 9.6 Hz, 1 H), 6.89-6.97 (m, 1 H), 6.27 (ddd, J = 2.3, 7.9, 9.8 Hz, 1 H), 6.15 (dd, J = 2.3, 10.6 Hz, 1 H), 4.51-4.62 (m, 2 H), 3.53-3.69 (m, 1 H), 3.40 (t, J = 8.3 Hz, 2 H), 3.05 (td, J = 2.3, 12.9 Hz, 2 H), 2.90 (t, J = 8.5 Hz, 2 H), 1.88-2.00 (m, 2 H), 1.69-1.81 (m, 2 H) (NH not shown); MS: 365 (M$^+$ + 1)

| 80 | 1-(1-(6-(1-methyl-1H-pyrazol-4-yl)pyridazin-3-yl)piperidin-4-yl)-4-(trifluoromethyl)-1H-indazole |

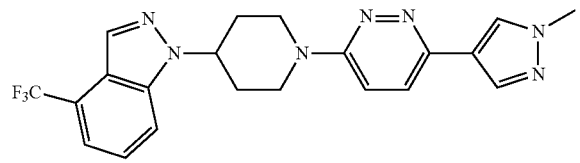 [SMILES: Cn1cc(-c2ccc(N3CCC(n4ncc5c(C(F)(F)F)cccc54)CC3)nn2)cn1]

MS: 428 (M$^+$ + 1)

| 81 | 1-(1-(6-(1-methyl-1H-pyrazol-4-yl)pyridazin-3-yl)piperidin-4-yl)-6-(trifluoromethyl)-1H-indazole |

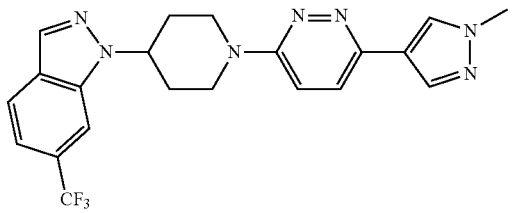 [SMILES: Cn1cc(-c2ccc(N3CCC(n4ncc5ccc(C(F)(F)F)cc54)CC3)nn2)cn1]

MS: 428 (M$^+$ + 1)

| 82 | 2-(4-(6-(4-(6-fluoro-1H-indazo-1-yl)piperidin-1-yl)pyridazin-3-yl)-1H-pyrazol-1-yl)ethanol |

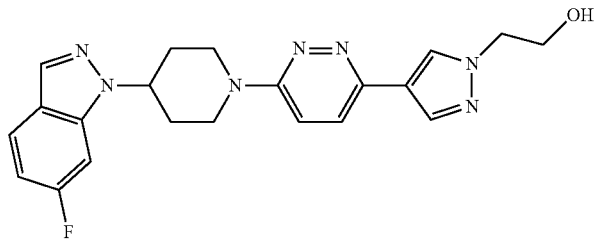 [SMILES: OCCn1cc(-c2ccc(N3CCC(n4ncc5ccc(F)cc54)CC3)nn2)cn1]

$^1$H NMR (400 MHz, CHLOROFORM-d) δ 8.04 (s, 1H), 7.96 (s, 2H), 7.66-7.69 (m, 1H), 7.41 (d, 1H), 7.12 (d, 1H), 7.03 (d, 1H), 6.92-6.96 (m, 1H), 4.59-4.62 (m, 3H), 4.31-4.33 (m, 2H), 4.05-4.07 (m, 2H), 3.21-.3.28 (t, 2H), 2.37-2.40 (dq, 2H), 2.15-2.18 (m, 2H); MS: 408 (M$^+$ + 1)

TABLE 3-continued

Measured Properties for Prepared Compounds of Formula (I)

| ID No. | Compound Name, Structure and Measured ¹HNMR and/or MS |
|---|---|
| 83 | 3-chloro-1-(1-(6-(1-methyl-1H-pyrazol-4-yl)pyridazin-3-yl)piperidin-4-yl)-1H-indazole 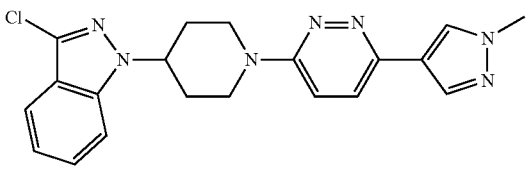 [SMILES: Cn1cc(-c2ccc(N3CCC(n4nc(Cl)c5ccccc54)CC3)nn2)cn1] ¹H NMR (400 MHz, CHLOROFORM-d) δ = 7.97 (s, 1 H), 7.92 (s, 1 H), 7.69 (d, 1 H), 7.41-7.45 (m, 2 H), 7.19-7.26 (m, 2 H), 7.02 (d, 1 H), 4.58-4.68 (m, 3 H), 3.98 (s, 3 H), 3.18-3.25 (t, 2 H), 2.36-2.41 (dq, 2 H), 2.13-2.19 (m, 2H); MS: 394 (M⁺ + 1) |
| 84 | 3-(1-(6-(1H-imidazol-1-yl)pyridazin-3-yl)piperidin-4-yl)-5-fluorobenzo[d]isoxazole 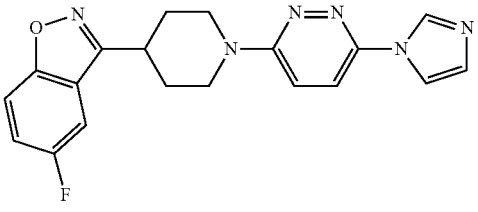 [SMILES: Fc1ccc2onc(C3CCN(c4ccc(-n5ccnc5)nn4)CC3)c2c1] ¹H NMR (400 MHz, DMSO-d₆) δ = 8.47 (br. s., 1 H), 7.94 (d, J = 9.1 Hz, 3 H), 7.79 (dd, J = 3.8, 9.3 Hz, 1 H), 7.65 (d, J = 9.6 Hz, 1 H), 7.55 (td, J = 2.0, 9.1 Hz, 1 H), 7.15 (br. s., 1 H), 4.52 (d, J = 12.9 Hz, 2 H), 3.45-3.59 (m, 1 H), 3.21 (t, J = 11.4 Hz, 2 H), 2.19 (d, J = 12.4 Hz, 2 H), 1.79-1.95 (m, 2 H); MS: 365 (M⁺ + 1) |
| 85 | 5-fluoro-3-(1-(6-(4-methyl-1H-imidazol-1-yl)pyridazin-3-yl)piperidin-4-yl)benzo[d]isoxazole 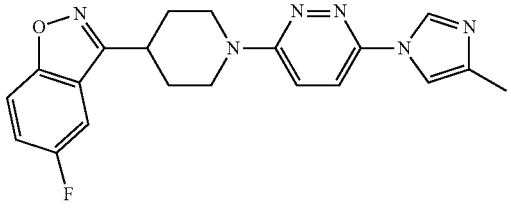 [SMILES: Cc1cn(-c2ccc(N3CCC(c4noc5ccc(F)cc45)CC3)nn2)cn1] ¹H NMR (400 MHz, CHLOROFORM-d) δ = 8.17 (br. s., 1 H), 7.54 (dd, J = 3.9, 9.0 Hz, 1 H), 7.28-7.41 (m, 4 H), 7.16 (d, J = 9.9 Hz, 1 H), 4.50 (d, J = 13.6 Hz, 2 H), 3.34-3.46 (m, 1 H), 3.22-3.34 (m, 2 H), 2.32 (s, 3 H), 2.21-2.29 (m, 2 H), 2.05-2.19 (m, 2 H); MS: 379 (M⁺ + 1) |
| 87 | 3-(1-(6-(1H-pyrazol-1-yl)pyridazin-3-yl)piperidin-4-yl)-5-fluorobenzo[d]isoxazole 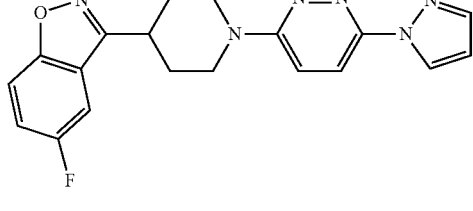 ¹H NMR (400 MHz, CHLOROFORM-d) δ = 8.64 (d, J = 2.5 Hz, 1 H), 8.04 (d, J = 9.6 Hz, 1 H), 7.75 (d, J = 1.5 Hz, 1 H), 7.54 (dd, J = 3.9, 9.0 Hz, 1 H), 7.27-7.39 (m, 2 H), 7.21 (d, J = 9.9 Hz, 1 H), 6.43-6.54 (m, 1 H), 4.51 (d, J = 13.6 Hz, 2 H), 3.39 (tt, J = 3.9, 11.3 Hz, 1 H), 3.22-3.33 (m, 2 H), 2.20-2.31 (m, 2 H), 2.06-2.20 (m, 2 H); MS: 365 (M⁺ + 1) |

TABLE 3-continued

Measured Properties for Prepared Compounds of Formula (I)

| ID No. | Compound Name, Structure and Measured ¹HNMR and/or MS |
|---|---|
| 88 | 1-(1-(6-(4-methyl-1H-imidazol-1-yl)pyridazin-3-yl)piperidin-4-yl)-1H-indole 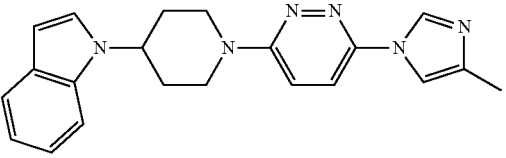 ¹H NMR (400 MHz, CHLOROFORM-d) δ = 8.17 (s, 1 H), 7.65 (d, J = 7.8 Hz, 1 H), 7.42 (d, J = 7.8 Hz, 1 H), 7.33-7.39 (m, 2 H), 7.20-7.25 (m, 2 H), 7.08-7.20 (m, 2 H), 6.54 (d, J = 3.3 Hz, 1 H), 4.48-4.67 (m, 3 H), 3.17-3.30 (m, 2 H), 2.32 (s, 3 H), 2.18-2.31 (m, 2 H), 2.04-2.18 (m, 2 H); MS: 359 (M⁺ + 1) |
| 89 | 6-fluoro-3-(1-(6-(4-methyl-1H-imidazol-1-yl)pyridazin-3-yl)piperidin-4-yl)benzo[d]isoxazole 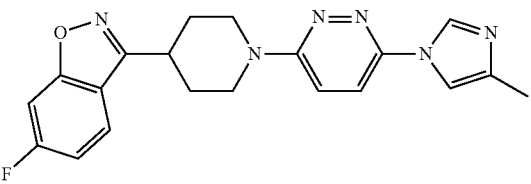 [SMILES: Cc1cn(-c2ccc(N3CCC(c4noc5cc(F)ccc45)CC3)nn2)cn1] ¹H NMR (400 MHz, CHLOROFORM-d) δ = 8.11-8.19 (m, 1 H), 7.66 (dd, J = 5.1, 8.8 Hz, 1 H), 7.31-7.39 (m, 2 H), 7.21-7.30 (m, 1 H), 7.16 (d, J = 9.6 Hz, 1 H), 7.08 (td, J = 2.3, 8.8 Hz, 1 H), 4.40-4.56 (m, 2 H), 3.42 (tt, J = 3.9, 11.2 Hz, 1 H), 3.21-3.35 (m, 2 H), 2.31 (s, 3 H), 2.19-2.29 (m, 2 H), 2.05-2.19 (m, 2 H); MS: 379 (M⁺ + 1) |
| 90 | 1-(1-(6-(4-methyl-1H-imidazol-1-yl)pyridazin-3-yl)piperidin-4-yl)-1,2,3,4-tetrahydroquinoline 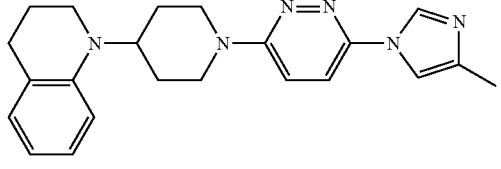 [SMILES: Cc1cn(-c2ccc(N3CCC(N4CCCc5ccccc54)CC3)nn2)cn1] ¹H NMR (400 MHz, CHLOROFORM-d) δ = 8.15 (d, J = 1.0 Hz, 1 H), 7.35 (s, 1 H), 7.32 (d, J = 9.9 Hz, 1 H), 7.12 (d, J = 9.9 Hz, 1 H), 7.04-7.10 (m, 1 H), 6.97 (s, 1 H), 6.73 (d, J = 8.3 Hz, 1 H), 6.60 (t, J = 7.1 Hz, 1 H), 4.48-4.60 (m, 2 H), 3.89-4.02 (m, 1 H), 3.15-3.21 (m, 2 H), 3.04-3.15 (m, 2 H), 2.74 (t, J = 6.2 Hz, 2 H), 2.31 (s, 3 H), 1.79-1.98 (m, 6 H); MS: 375 (M⁺ + 1) |
| 91 | (1-(6-(4-(5-fluorobenzo[d]isoxazol-3-yl)piperidin-1-yl)pyridazin-3-yl)-1H-imidazol-4-yl)methanol 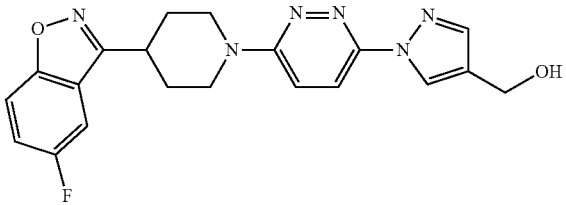 [SMILES: OCc1cnn(-c2ccc(N3CCC(c4noc5ccc(F)cc45)CC3)nn2)c1] MS: 395 (M⁺ + 1) |

TABLE 3-continued

Measured Properties for Prepared Compounds of Formula (I)

| ID No. | Compound Name, Structure and Measured ¹HNMR and/or MS |
|---|---|
| 92 | 5-fluoro-3-(1-(6-(3-methyl-1H-pyrazol-1-yl)pyridazin-3-yl)piperidin-4-yl)benzo[d]isoxazole |

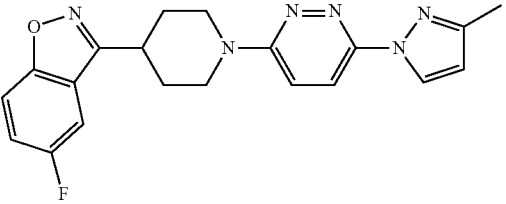 [SMILES: Cc1ccn(-c2ccc(N3CCC(c4noc5ccc(F)cc45)CC3)nn2)n1]

¹H NMR (400 MHz, CHLOROFORM-d) δ = 8.52 (d, J = 2.3 Hz, 1 H), 7.99 (d, J = 9.6 Hz, 1 H), 7.54 (dd, J = 3.7, 9.2 Hz, 1 H), 7.27-7.38 (m, 2 H), 7.18 (d, J = 9.9 Hz, 1 H), 6.27 (d, J = 2.5 Hz, 1 H), 4.49 (dt, J = 3.1, 13.5 Hz, 2 H), 3.38 (tt, J = 4.1, 11.3 Hz, 1 H), 3.20-3.32 (m, 2 H), 2.38 (s, 3 H), 2.20-2.29 (m, 2 H), 2.07-2.20 (m, 2 H); MS: 379 (M$^+$ + 1)

| 93 | 5-fluoro-3-(1-(6-(2-methyl-1H-imidazol-1-yl)pyridazin-3-yl)piperidin-4-yl)benzo[d]isoxazole |

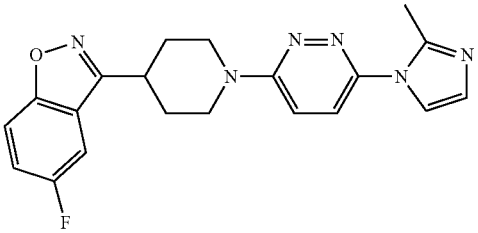 [SMILES: Cc1nccn1-c1ccc(N2CCC(c3noc4ccc(F)cc34)CC2)nn1]

¹H NMR (400 MHz, CHLOROFORM-d) δ = 7.55 (dd, J = 3.2, 9.0 Hz, 1 H), 7.28-7.38 (m, 3 H), 7.20 (d, J = 1.3 Hz, 1 H), 7.14 (d, J = 9.6 Hz, 1 H), 7.06 (d, J = 1.5 Hz, 1 H), 4.51-4.62 (m, 2 H), 3.28-3.48 (m, 3 H), 2.58 (s, 3 H), 2.28 (d, J = 18.2 Hz, 2 H), 2.08-2.20 (m, 2 H); MS: 379 (M$^+$ + 1)

| 94 | 5-fluoro-3-(1-(6-(4-methyl-1H-pyrazol-1-yl)pyridazin-3-yl)piperidin-4-yl)benzo[d]isoxazote |

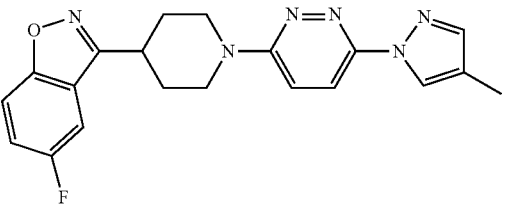 [SMILES: Cc1cnn(-c2ccc(N3CCC(c4noc5ccc(F)cc45)CC3)nn2)c1]

¹H NMR (400 MHz, CHLOROFORM-d) δ = 8.39 (s, 1 H), 7.99 (d, J = 9.9 Hz, 1 H), 7.55 (s, 1 H), 7.51-7.55 (m, 1 H), 7.28-7.38 (m, 2 H), 7.18 (d, J = 9.9 Hz, 1 H), 4.49 (dt, J = 3.1, 13.3 Hz, 2 H), 3.38 (tt, J = 3.9, 11.3 Hz, 1 H), 3.21-3.32 (m, 2 H), 2.21-2.29 (m, 2 H), 2.18 (s, 3 H), 2.07-2.17 (m, 2 H); MS: 379 (M$^+$ + 1)

TABLE 3-continued

Measured Properties for Prepared Compounds of Formula (I)

| ID No. | Compound Name, Structure and Measured ¹HNMR and/or MS |
|---|---|

95     (1-(6-(4-(5-fluorobenzo[d]isoxazol-3-yl)piperidin-1-yl)pyridazin-3-yl)-1H-pyrazol-4-yl)methanol

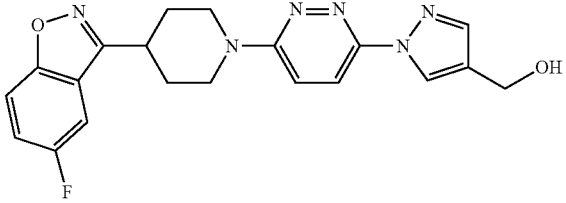 [SMILES: OCc1cnn(-c2ccc(N3CCC(c4noc5ccc(F)cc45)CC3)nn2)c1]

¹H NMR (400 MHz, CHLOROFORM-d) δ = 8.61 (s, 1 H), 8.01 (d, J = 9.6 Hz, 1 H), 7.77 (s, 1 H), 7.54 (dd, J = 3.8, 9.1 Hz, 1 H), 7.27-7.38 (m, 2 H), 7.20 (d, J = 9.9 Hz, 1 H), 4.71 (d, J = 5.8 Hz, 2 H), 4.51 (dt, J = 3.3, 13.5 Hz, 2 H), 3.39 (tt, J = 3.8, 11.3 Hz, 1 H), 3.22-3.33 (m, 2 H), 2.20-2.30 (m, 2 H), 2.07-2.20 (m, 2 H), 1.59 (t, J = 5.7 Hz, 1 H); MS: 395 (M⁺ + 1)

96     5-fluoro-3-(1-(6-(4-(methoxymethyl)-1H-pyrazol-1-yl)pyridazin-3-yl)piperidin-4-yl)benzo[d]isoxazole

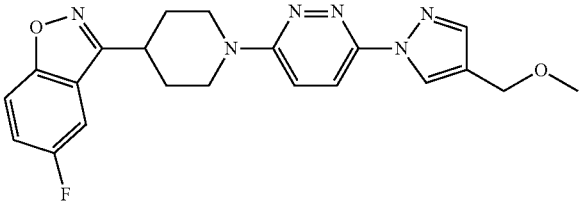 [SMILES: COCc1cnn(-c2ccc(N3CCC(c4noc5ccc(F)cc45)CC3)nn2)c1]

¹H NMR (400 MHz, CHLOROFORM-d) δ = 8.59 (s, 1 H), 8.01 (d, J = 9.9 Hz, 1 H), 7.74 (s, 1 H), 7.54 (dd, J = 3.4, 9.0 Hz, 1 H), 7.28-7.38 (m, 2 H), 7.19 (d, J = 9.9 Hz, 1 H), 4.50 (dt, J = 3.1, 13.5 Hz, 2 H), 4.46 (s, 2 H), 3.39 (s, 3 H), 3.34-3.44 (m, 1 H), 3.23-3.33 (m, 2 H), 2.21-2.30 (m, 2 H), 2.07-2.20 (m, 2 H); MS: 409 (M⁺ + 1)

97     1-(1-(6-(4-(5-fluorobenzo[d]isoxazol-3-yl)piperidin-1-yl)pyridazin-3-yl)-1H-pyrazol-4-yl)-N-methylmethanamine

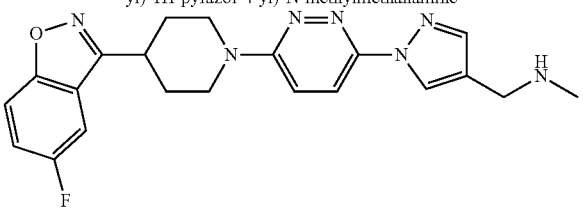

¹H NMR (400 MHz, CHLOROFORM-d) δ = 8.55 (s, 1 H), 8.00 (d, J = 9.6 Hz, 1 H), 7.72 (s, 1 H), 7.54 (dd, J = 4.0, 9.3 Hz, 1 H), 7.28-7.38 (m, 2 H), 7.19 (d, J = 9.6 Hz, 1 H), 4.50 (dt, J = 3.1, 13.7 Hz, 2 H), 3.77 (s, 2 H), 3.38 (tt, J = 3.8, 11.2 Hz, 1 H), 3.21-3.33 (m, 2 H), 2.51 (s, 3 H), 2.20-2.31 (m, 2 H), 2.07-2.20 (m, 2 H) (NH not shown); MS: 408 (M⁺ + 1)

TABLE 3-continued

Measured Properties for Prepared Compounds of Formula (I)

| ID No. | Compound Name, Structure and Measured ¹HNMR and/or MS |
|---|---|
| 98 | 2-(1-(6-(4-(5-fluorobenzo[d]isoxazol-3-yl)piperidin-1-yl)pyridazin-3-yl)-1H-pyrazol-4-yl)ethanol |

¹H NMR (400 MHz, CHLOROFORM-d) δ = 8.50 (s, 1 H), 8.00 (d, J = 9.9 Hz, 1 H), 7.64 (s, 1 H), 7.54 (dd, J = 3.8, 9.1 Hz, 1 H), 7.28-7.38 (m, 2 H), 7.19 (d, J = 9.9 Hz, 1 H), 4.44-4.55 (m, 2 H), 3.86 (q, J = 6.3 Hz, 2 H), 3.38 (tt, J = 3.9, 11.3 Hz, 1 H), 3.21-3.33 (m, 2 H), 2.83 (t, J = 6.4 Hz, 2 H), 2.21-2.30 (m, 2 H), 2.06-2.21 (m, 2 H), 1.54 (t, J = 5.8 Hz, 1 H); MS: 409 (M⁺ + 1)

| I1 | 6-(4-(5-fluorobenzo[d]isoxazol-3-yl)piperidin-1-yl)pyridazine-3-carbohydrazide |
|---|---|

¹H NMR (400 MHz, CHLOROFORM-d) δ = 8.83 (br. s., 1 H), 7.99 (d, J = 9.6 Hz, 1 H), 7.54 (dd, J = 3.0, 8.8 Hz, 1 H), 7.28-7.37 (m, 2 H), 7.05 (d, J = 9.6 Hz, 1 H), 4.55-4.66 (m, 2 H), 4.08 (br. s., 2 H), 3.30-3.49 (m, 3 H), 2.18-2.33 (m, 2 H), 2.04-2.18 (m, 2 H); MS: 357 (M⁺ + 1)

| I2 | N'-acetyl-6-(4-(5-fluorobenzo[d]isoxazol-3-yl)piperidin-1-yl)pyridazine-3-carbohydrazide |
|---|---|

¹H NMR (400 MHz, CHLOROFORM-d) δ = 9.86 (d, J = 4.5 Hz, 1 H), 8.01 (d, J = 4.8 Hz, 1 H), 7.97 (d, J = 9.6 Hz, 1 H), 7.49-7.59 (m, 1 H), 7.28-7.38 (m, 2 H), 7.04 (d, J = 9.6 Hz, 1 H), 4.62 (d, J = 13.4 Hz, 2 H), 3.29-3.52 (m, 3 H), 2.28 (d, J = 13.6 Hz, 2 H), 2.14 (s, 3 H), 2.00-2.19 (m, 2 H); MS: 399 (M⁺ + 1)

BIOLOGICAL EXAMPLE 1

SCD1 Enzymatic Assay (In Vitro Assay)

Step 1: Preparation of Rat Liver Microsome (RLM):

Sprague Dawley rats from Charles River (200-225 g) underwent 2-cycle of fast-re-feeding (24-hour fast followed by 24-hour feeding with fat-free high carbohydrate diet, Reseach Diet, D00042802). The livers were removed and homogenized 1:4 (w/v) with pre-chilled, homogenizing buffer (10 mM Tris-HCl, 0.25 M sucrose, 1 mM EDTA, pH 7.4, supplemented with protease inhibitor cocktail). The homogenate was spun at 12,000×g for 15 min at 4° C. The supernatant was then re-centrifuged at 100,000×g for 60 min at 4° C. The pellet was re-suspended in 2 ml pre-chilled 0.2 mM potassium phosphate buffer, pH 7.2, 10 mM EDTA at a concentration of 20 mg/ml. The resulting rat liver microsome (RLM) preparation was stored at −80° C.

Step 2: SCD1 Enzymatic Assay in RLM:

The SCD1 enzymatic assay was done in a volume of 50 μL using 10 μg of RLM (prepared as described above) in a 96-well polypropylene plate (enzyme reaction buffer contains 0.1 M K-Phosphate Buffer, 10 mM ATP, 6 mM MgCl₂, 1 mM CoA, 1 mM β-NADH, 1.6 mM L-glutathione, 20 μM Stearoyl-CoA). Stearoyl-[9,10-³H]-CoA (ARC-0390, 1 mCi/mL, 60 Ci/mmol,) was added at a final concentration of 2

μCi/mL. Test compound was then added to the reaction mixture at the selected concentration. After incubation at room temperature for 2 hours, 5 μL 1 N HCl was added to stop the reaction, followed by addition of 25 μL of 10% charcoal. The reaction mixture was then transferred to 96-well Multiscreen plate (Millipore, Cat#MSFCN6B50). [$^3H_2O$] was collected into Opti-plate (PE, Cat#6005290) by centrifuge, at 1,000 rpm for 2 minutes. 150 μL Microscint 40 (PE, cat #6013641) was then added to each well and counted on Topcount for [$^3H$] counts per minute (cpm). The measured cpm values were fitted with Sigmoidal dose-response curve fit with Graphpad Prism.

BIOLOGICAL EXAMPLE 2

SCD1 $^{13}$C-Palmitic Acid Assay in A431 Cells (In Vitro Assay)

Human epithelial carcinoma A431 cells were seeded at 100,000 cells/well in complete growth medium (DMEM, Cellgro#10-013-CM, 4.5 g/L glucose, 10% FBS) in the presence of 0.05 mg/mL human insulin (Hannas Pharmaceutical Supply Co Inc, Humanlin 100 U/ml, 4 mg/ml) in 96-well tissue culture plate. 24 hr later, the cells were washed extensively with Assay Buffer (DMEM, Cellgro#10-013-CM, 4.5 g/L glucose, supplemented with 0.05 mg/mL Human Insulin and 0.1% Fatty Acid Free BSA). Assay Buffer including 20 μM U-$^{13}$C16 palmitic acid (100 μL) was then added to each well (Cambridge Isotope Laboratories, CLM-409-0.5) followed by addition of 5 μL of vehicle or test compound. The cells were then returned to the tissue culture incubator (37° C. and 5% $CO_2$) for 4 hrs. At the end of incubation, the cells were washed three times with 200 μL/well Hanks buffer (HBSS) and then stored at −20° C. until extraction.

For fatty acid extraction, after thawing out the plates, 40 μL of 1N KOH (containing 5 μM of internal standard 7,7,8,8-D4 palmitate) was added to each well and cell plates were incubated at 37° C. for 30 minutes. Subsequently, 30 μL of cell lysate was transferred to the 96-well plate (Axygen, PCR-96-FS-C plate, Cat#321-60-051) and the plate incubate at 85° C. for 30 minutes. Heated cell lysate was quickly spun at room temperature and 5 μL formic acid (Sigma, Cat#251364) was added to neutralize the solution. Acetonitrile (100 μL) was then added to extract fatty acids, followed by centrifugation at 3000 rpm for 10 minutes. 75 μL of extract was then transferred to a new glass vial in a 96-well cluster plate. 5 μL was injected for LC/MS analysis for detection of $^{13}$C-palmitic acid and $^{13}$C-palmitoleic acid. Formation of product $^{13}$C-palmitoleic acid was determined as an index of SCD1 activity.

LC/MS analysis was performed as following. An Agilent 1100 Liquid Chromatographic System (Palo Alto, Calif.) consisting of a binary pump, a degasser and an autosampler was used. Separation of free fatty acids was performed on a Zorbax SB-$C_8$ column (2.1×50 mm, particle size=3.5 μm). An isocratic elution was carried out with 10 mM triethylamine acetate in water: acetonitrile (3:7) at a flow rate of 0.3 mL/min. The column temperature was set at 30° C. and the sample injection volume was 5 μL. The LC run cycle was 4 min. A Micromass triple-quadrupole Quattro Micro mass spectrophotometer (Waters, Beverly, Mass.) was interfaced with the LC system through a Z-spray electrospray ion source and was operated in the negative ion mode. Nitrogen was used as nebulizing gas, desolvation gas and cone curtain gas and argon was chosen as collision gas. The triple quadrupole MS source parameters were set as follows: capillary voltage, 3200V; cone voltage, 25V; exctractor 2V; source temperature, 120° C.; desolvation temperature, 300° C.; cone gas flow, 50 L/h; and desolvation gas flow, 700 L/h. Selected ion recording (SIR) was applied to detection of U-$^{13}$C-palmitoleic acid at m/z 269.4 (M-H), U-$^{13}$C-palmitic acid at m/z 271.4 (M-H) and 7,7,8,8-D4 palmitate (internal standard) at m/z 259.4 (M-H). MassLynx software version 4.0 was used for system control and data processing. The signal of U-$^{13}$C-palmitoleic acid was normalized to an internal standard.

Plasma Desaturation Index Determination:

Total plasma lipid fatty acid desaturation index (C16:1/C16:0 and C18:1/C18:0) was determined after alkaline digestion. Briefly, 10 μl of plasma was added to 50 μL of 1 M KOH in 65% ethanol containing 10 μM internal standard (7,7,8,8-D4 palmitate) and incubated at 55° C. for 1 hr. After neutralization with 10 μL formic acid, fatty acids were extracted with acetonitrile and subjected to LC/MS measurement as described above.

BIOLOGICAL EXAMPLE 3

SCD1 $^{14}$C-Palmitate Assay in A431 Cells (In Vitro Assay)

Human epithelial carcinoma A431 cells were seeded at 400,000 cells per well in 48-well tissue culture plate and treated with 2 cycles of fasting in low glucose medium (DMEM, Cellgro#10-014-CV, 1 g/L glucose, 2% Charcoal Filtered FBS) for 24 hours; and re-feeding with high glucose medium for 24 hours (DMEM, Cellgro#10-013-CM, 4.5 g/L glucose, 10% Charcoal Filtered FBS and 0.05 mg/mL Lilly Humulin R, Cat.#, HI-210). Prior to running the assay, the cells were washed twice with high glucose medium (400 μL), followed by addition of 250 μL assay buffer (DMEM, 4.5 g/L glucose, 0.05 mg/mL Human Insulin, 0.1% Fatty Acid Free BSA) to each well. Then, 100 μL of assay buffer containing 20 μM Palmitic Acid, 0.05 μCi $^{14}$C Palmitic Acid (Perkin Elmer, NEC075H) and test compound (at selected concentration) was added to each well. The cells were then Incubated at 37° C. and 5% $CO_2$ tissue culture incubator for 4 hours, followed by extensive washes with pre-chilled PBS. The cell plates were then frozen at −20° C. overnight. After thawing out the plates, 100 μL of 1N KOH was added to each well and the plates were incubated at 37° C. for 30 mins. Cell lysates were transferred to 1 mL Eppendorf tubes and incubated at 95° C. for 1 hour, followed by addition of 10 μL formic acid and 220 μL acetonitrile. The tubes were then centrifuged at 12,000 rpm and the supernatant dried under $N_2$ for 2-3 hours. Dried extract was re-suspended in 60 μL hexane and loaded onto TLC plates (pre-coated with 10% $AgNO_3$ in acetonitrile). The TLC plates were placed into glass running chamber containing 200 mL running solution (100 mL running solution: 92.5 mL chloroform, 6 mL methanol, 750 μL acetic acid, 750 μL $dH_2O$). After running, the TLC plates were air dried and scanned on Bioscan AR-2000 for quantification of $^{14}$C-palmitioleate and $^{14}$C-palmitate peaks. Area under the curve of the peaks were used to calculate product/substrate ratio, an index of SCD1 activity.

Representative compounds of the present invention were tested according to the procedures as outlined in Biological Examples 1-3 above, with results as listed in Table 4, below. Where a particular compound was tested multiple times, multiple measured values are listed below.

TABLE 4

Biological Activity for Representative Compounds of Formula (I)

| ID | % Inh.@ 1 μM | IC$_{50}$ (μM) | A431 cells $^{13}$C-PA IC$_{50}$ (μM) | A431 cells $^{14}$C-PA IC$_{50}$ (μM) |
|---|---|---|---|---|
| 1 | 86 | 0.076 | | 0.257 |
| 3 | 87 | 0.126 | | 0.377 |
| 4 | 95, 95, 93 | 0.020, 0.012 | 0.009 | 0.068 |
| 5 | 89 | 0.068 | | 0.139 |
| 6 | 79 | 0.034 | | 0.062, 0.102 |
| 7 | 95 | 0.014 | | 0.024 |
| 8 | 86 | 0.165 | | 0.577 |
| 9 | 81 | 0.422 | | 0.359 |
| 10 | 84 | 0.394 | | 0.383 |
| 11 | 99, 100, 94, 102 | 0.021, 0.019, 0.091, 0.016 | 0.015, 0.012, 0.017 | 0.12 |
| 12 | 95, 97 | 0.011, 0.011 | | 0.362 |
| 13 | 98 | 0.070 | 0.985 | |
| 15 | 101 | 0.011 | 0.003 | |
| 16 | 100 | 0.021 | 0.023 | |
| 18 | 56, 52, 34, 27 | 0.315 | 0.248 | |
| 20 | 96, 96 | 0.016, 0.014 | 0.011 | |
| 21 | 94 | 0.017 | 0.040, 0.019 | |
| 22 | 98, 91 | 0.022, 0.011 | 0.007, 0.005 | |
| 23 | 100 | 0.021 | 0.003 | |
| 24 | 98, 94 | 0.011, 0.004 | 0.009, 0.006 | |
| 25 | 62 | 0.171 | 0.017, 0.017 | |
| 26 | 86 | 0.111 | 0.112 | |
| 27 | 75, 55 | 0.114, 0.122 | 0.004, 0.003 | |
| 28 | 94 | 0.009 | 0.009, 0.016 | |
| 29 | 97 | 0.007 | 0.002 | |
| 30 | 95, 99 | 0.006, 0.019 | 0.002, 0.003, 0.002 | |
| 31 | 97 | 0.031 | 0.004, 0.019 | |
| 32 | 45 | >1 | | |
| 33 | 100 | 0.007 | 0.004 | |
| 34 | 75 | 0.095 | 0.017 | |
| 35 | 99 | 0.008 | 0.002, 0.002 | |
| 36 | 92 | 0.079 | 0.003, 0.018 | |
| 37 | 98 | 0.012 | 0.004 | |
| 38 | 97 | 0.011 | 0.034 | |
| 39 | 99 | 0.009 | 0.0005 | |
| 40 | 92 | 0.092 | 0.045 | |
| 41 | 38 | >1 | | |
| 42 | 71 | 0.035 | 0.006 | |
| 43 | 90 | 0.020 | 0.011 | |
| 44 | 92, 97 | 0.020, 0.014 | 0.032, 0.028 | |
| 45 | 98 | 0.015 | 0.006 | |
| 46 | 85 | 0.165 | 0.099 | |
| 47 | 100, 96 | 0.036, 0.039 | 0.069, 0.033 | |
| 48 | 60 | 0.939 | | |
| 49 | 95, 91 | 0.025, 0.019 | 0.021, 0.021, 0.022 | |
| 50 | 93 | 0.031 | 0.044 | |
| 51 | 96 | 0.022 | 0.008 | |
| 52 | 92 | 0.121 | 0.006 | |
| 53 | 59 | 0.777 | | |
| 54 | 85 | 0.090 | 0.054 | |
| 55 | 8 | >1 | | |
| 56 | 28 | >1 | | |
| 57 | 72 | 0.286 | 0.241 | |
| 58 | 78 | 0.349 | 0.390 | |
| 59 | 99 | 0.035 | 0.028 | |
| 60 | 81 | 0.173 | 0.042 | |
| 61 | 101 | 0.015 | 0.017 | |
| 62 | 79 | 0.317 | 0.407 | |
| 63 | 99 | 0.023 | 0.025 | |
| 64 | 102 | 0.015 | 0.012 | |
| 65 | 83 | 0.181 | 0.218 | |
| 66 | 57 | 0.678 | | |
| 67 | 32 | >1 | | |
| 68 | 34 | >1 | | |
| 69 | 68 | 0.387 | 0.559 | |
| 70 | 94 | 0.068 | 0.082 | |
| 71 | 71 | 0.275 | >1, 0.160 | |
| 72 | 99 | 0.008 | 0.009 | |
| 73 | 86 | 0.145 | 0.262 | |
| 74 | 96 | 0.016 | 0.022 | |
| 75 | 98 | 0.021 | 0.081 | |
| 76 | 97 | 0.016 | 0.014 | |
| 77 | 95 | 0.021 | 0.020 | |
| 78 | 99 | 0.012 | 0.041 | |
| 79 | 97 | 0.022 | 0.072 | |
| 80 | 74 | 0.052 | 0.731 | |
| 81 | 96 | 0.008 | 0.015 | |
| 82 | 99 | 0.053 | 0.096 | |
| 83 | 102 | 0.006 | 0.011 | |
| 84 | 85 | 0.156 | | 0.157 |
| 85 | 97 | 0.065 | | 0.148 |
| 87 | 45 | | | |
| 88 | 84 | 0.086 | | 0.116 |
| 89 | 88 | 0.257 | | 0.691 |
| 90 | 29 | | | |
| 91 | 96 | 0.052 | | 0.040 |
| 92 | 79 | 0.126 | | 0.063 |
| 93 | 41 | | | |
| 94 | 96 | 0.012 | 0.040 | |
| 95 | 88 | 0.096 | 0.062 | |
| 96 | 98 | 0.008 | 0.022, 0.022 | |
| 97 | 11 | | >1, >1 | |
| 98 | 88 | 0.060 | 0.012 | |
| I1 | 100 | 0.059 | >3.00 | 3.065 |
| I2 | 27 | | | |

BIOLOGICAL EXAMPLE 4

4 Week Zucker fa/fa Rat Study (In Vivo Assay)

Male Zucker fa/fa rats were housed one rat per cage in a temperature-controlled room with 12-hour light/dark cycle. The rats were fed on regular rodent diet (Purina 5008) and allowed ad libitum access to water. The experiment was initiated at an age of 8-9 week, and at body weight of about 350 g.

Test compound was prepared in 0.5% HPMC for dosing q.d at 1 mg/kg, 3 mg/kg and 10 mg/kg, as noted in the table of results below. Body weight, food intake and fed blood glucose were monitored weekly. On day 26, all rats were given with the last dose 1 hr prior to the necropsy. Orbital bleeding was performed under 70%/30% $CO_2/O_2$ anesthesia to collect plasma.

Compound #11 of the present invention was tested according to the procedure as described above, with results as listed in Table 5 and 6, below. In the results presented below, * indicates a calculated p value <0.05 vs. vehicle-treated group.

TABLE 5

4-Week Body Weight (in grams)

| Treatment | Day 1 | Day 8 | Day 15 | Day 22 | Day 26 |
|---|---|---|---|---|---|
| Vehicle | 373 ± 7 | 434 ± 9 | 476 ± 8 | 515 ± 7 | 534 ± 11 |
| Compound #11 @ 1 mg/kg | 373 ± 7 | 404 ± 13 | 442 ± 12 * | 482 ± 10 | 496 ± 10 |
| Compound #11 @ 3 mg/kg | 372 ± 6 | 417 ± 7 | 452 ± 6 * | 484 ± 6 * | 498 ± 6 * |
| Compound #11 @ 10 mg/kg | 373 ± 5 | 402 ± 6 * | 430 ± 7 * | 445 ± 9 * | 451 ± 9 * |

TABLE 6

| Plasma Desaturation Index at Day 26 | | |
|---|---|---|
| Treatment | C16:1/C16:0 | C18:1/C18:0 |
| Vehicle | 0.183 ± 0.012 | 2.16 ± 0.07 |
| Compound #11 @ 1 mg/kg | 0.122 ± 0.005 * | 1.59 ± 0.08 * |
| Compound #11 @ 3 mg/kg | 0.088 ± 0.002 * | 1.14 ± 0.07 * |
| Compound #11 @ 10 mg/kg | 0.078 ± 0.002 * | 0.92 ± 0.04 * |

BIOLOGICAL EXAMPLE 5

10-Day Diet-Induced Obese C57bl/6 Mice Study (In Vivo Assay)

Male DIO C57BL/6J mice from Taconic were maintained on high fat diet D12492 containing 60% kCal of mostly saturated fats (Research Diets Inc.) for 4 week from 6-week old. Test compounds were prepared in 0.5% hydroxypropyl methyl cellulose for oral dosing at 30 mg/kg once a day. After 10-days of treatment, body weight change was recorded.

Representative compounds of the present invention were tested according to the procedure as described above, with results as listed in Table 7, below. In the results presented below, * indicates a calculated p value <0.05 vs. vehicle-treated group.

TABLE 7

| 10-day dosing study, 30 mg/kg dosing | |
|---|---|
| Vehicle | 2.8 ± 0.3 |
| Compound #22 | 1.2 ± 0.3 * |
| Compound #11 | −2.1 ± 0.3 * |
| Compound #39 | −2.2 ± 0.5 * |
| Compound #47 | −3.3 ± 0.5 * |
| Compound #49 | 0.5 ± 0.1 * |

FORMULATION EXAMPLE 1

Solid, Oral Dosage Form—Prophetic Example

As a specific embodiment of an oral composition, 100 mg of the Compound #11, prepared as in Example 1 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (I)

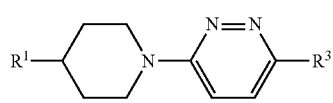

(I)

wherein
$R^1$ is selected from the group consisting of

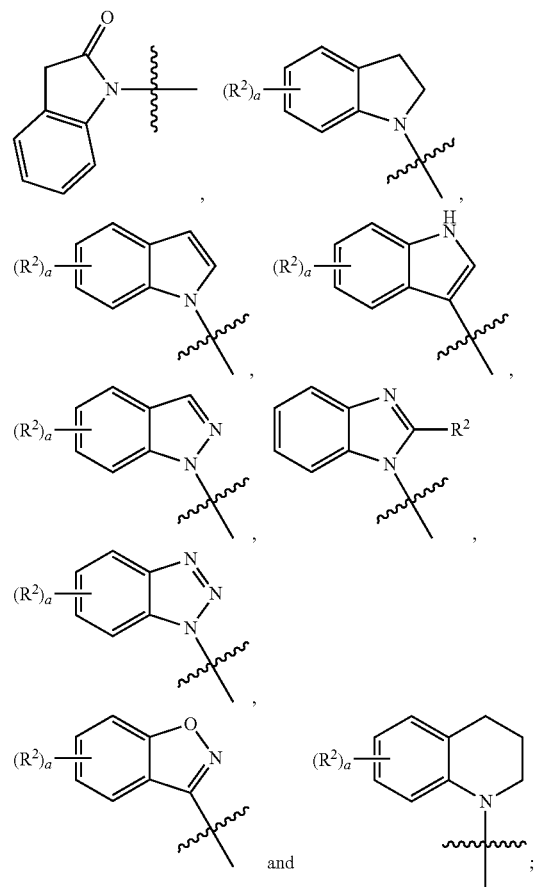

a is an integer from 0 to 3;
each $R^2$ is independently selected from the group consisting of halogen, $C_{1-4}$alkyl, $C_{1-4}$alkoxy, halogenated $C_{1-2}$alkyl, and halogenated $C_{1-2}$alkoxy;
$R^3$ is selected from the group consisting of

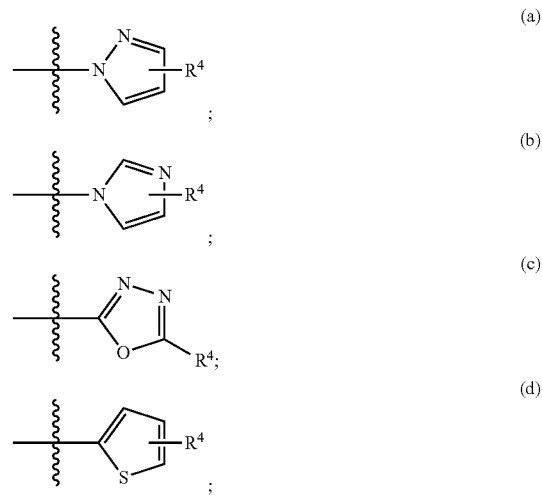

-continued

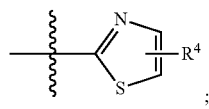 (e)

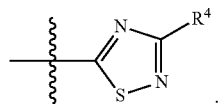 (f)

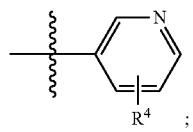 (g)

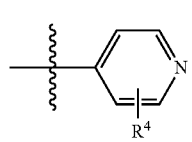 (h)

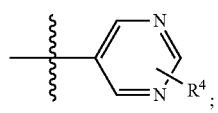 (i)

wherein $R^4$ is selected from the group consisting of hydrogen, halogen, $C_{1-4}$alkyl, halogenated $C_{1-2}$alkyl, —$C_{1-2}$alkyl-OH, $C_{1-4}$alkoxy, halogenated $C_{1-2}$alkoxy, —$C_{1-2}$alkyl-O—$C_{1-2}$alkyl, —$CO_2H$, —C(O)O—$C_{1-4}$alkyl, —$C_{1-2}$alkyl-C(O)O—$C_{1-2}$alkyl, —$C_{1-2}$alkyl-OC(O)—$C_{1-2}$alkyl, —$NR^A R^B$, —$C_{1-2}$alkyl-$NR^A R^B$, —C(O)—$NR^A R^B$, —$C_{1-2}$alkyl-C(O)—$NR^A R^B$ and —$NR^A$—C(O)—($C_{1-2}$alkyl);

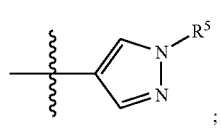 (j)

wherein $R^5$ is selected from the group consisting of hydrogen, $C_{1-4}$alkyl, —$C_{2-4}$alkyl-OH, —$C_{2-3}$alkyl-O—$C_{1-2}$alkyl, —$C_{1-2}$alkyl-C(O)O—$C_{1-2}$alkyl, —$C_{2-3}$alkyl-OC(O)—$C_{1-2}$alkyl, —$C_{2-4}$alkyl-$NR^A R^B$ and —$C_{1-2}$alkyl-C(O)$NR^A R^B$;

and

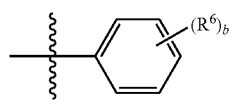 (k)

wherein b is an integer from 0 to 2;
wherein each $R^6$ is independently selected from the group consisting of halogen, $C_{1-4}$alkyl, halogenated $C_{1-4}$alkyl, —$C_{1-2}$alkyl-OH, $C_{1-4}$alkoxy, halogenated $C_{1-4}$alkoxy, —$C_{1-2}$alkyl-O—$C_{1-2}$alkyl, —$CO_2H$, —C(O)O—$C_{1-4}$alkyl, —$C_{1-2}$alkyl-C(O)O—$C_{1-2}$alkyl, —$C_{1-2}$alkyl-OC(O)—$C_{1-2}$alkyl, —C(O)—$NR^A R^B$, —$C_{1-2}$alkyl-C(O)—$NR^A R^B$, —$NR^A R^B$, —$C_{1-2}$alkyl-$NR^A R^B$ and —$NR^A$—C(O)—$C_{1-2}$alkyl;

and wherein $R^A$ and $R^B$ are each independently selected from the group consisting of hydrogen and $C_{1-2}$alkyl; alternatively $R^A$ and $R^B$ are taken together with the nitrogen atom to which they are bound to form piperidin-1-yl, piperazin-1-yl, morpholin-4-yl and pyrrolidin-1-yl;
provided that when $R^3$ is 3-methyl-1,2,4-thiadiazol-5-yl, then $R^1$ is other than unsubstituted indoly-3-yl;
or a pharmaceutically acceptable salt thereof.

2. A compound as in claim 1, wherein
$R^1$ is selected from the group consisting of

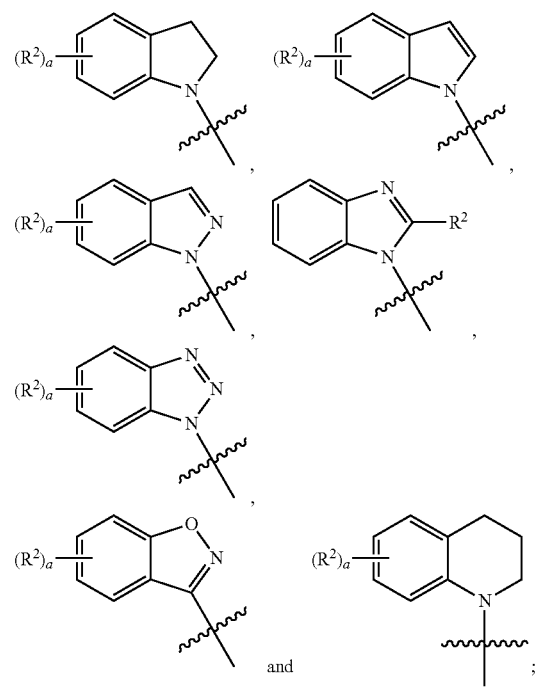

a is an integer from 0 to 2;
each $R^2$ is independently selected from the group consisting of halogen, $C_{1-2}$alkyl, $C_{1-2}$alkoxy, fluorinated $C_{1-2}$alkyl, and fluorinated $C_{1-2}$alkoxy;
$R^3$ is selected from the group consisting of

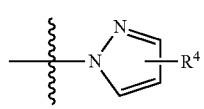 (a)

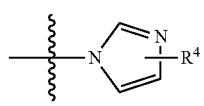 (b)

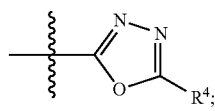 (c)

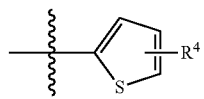 (d)

-continued

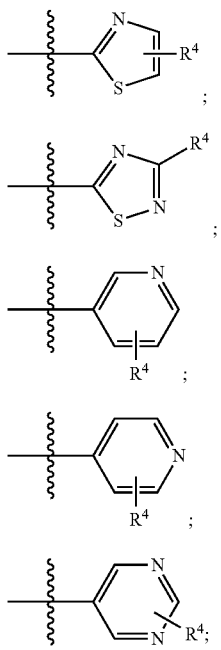

(e)

(f)

(g)

(h)

(i)

wherein $R^4$ is selected from the group consisting of hydrogen, halogen, $C_{1-4}$alkyl, fluorinated $C_{1-2}$alkyl, —$C_{1-2}$alkyl-OH, $C_{1-2}$alkoxy, fluorinated $C_{1-2}$alkoxy, —$C_{1-2}$alkyl-O—$C_{1-2}$alkyl, —$CO_2H$, —C(O)O—$C_{1-2}$alkyl, —$C_{1-2}$alkyl-OC(O)—$C_{1-2}$alkyl, —$NR^AR^B$, —$C_{1-2}$alkyl-$NR^AR^B$, —C(O)—$NR^AR^B$, —$C_{1-2}$alkyl-C(O)—$NR^AR^B$ and —$NR^A$—C(O)—($C_{1-2}$alkyl);

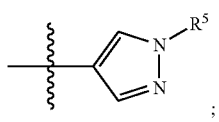

(j)

wherein $R^5$ is selected from the group consisting of hydrogen, $C_{1-4}$alkyl, —$C_{2-4}$alkyl-OH, —$C_{2-3}$alkyl-O—$C_{1-2}$alkyl, —$C_{1-2}$alkyl-C(O)O—$C_{1-2}$alkyl, —$C_{2-4}$alkyl-$NR^AR^B$ and —$C_{1-2}$alkyl-C(O)$NR^AR^B$; and

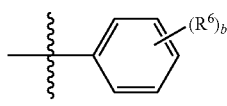

(k)

wherein b is an integer from 0 to 1;
wherein each $R^6$ is independently selected from the group consisting of halogen, $C_{1-4}$alkyl, fluorinated $C_{1-2}$alkyl, —$C_{1-2}$alkyl-OH, $C_{1-2}$alkoxy, fluorinated $C_{1-2}$alkoxy, —$C(O)_2H$, —C(O)O—$C_{1-4}$alkyl, —$C_{1-2}$alkyl-C(O)O—$C_{1-2}$alkyl, —C(O)—$NR^AR^B$, —$C_{1-22}$alkyl-C(O)—$NR^AR^B$, —$NR^AR^B$ and —$C_{1-2}$alkyl-$NR^AR^B$;
and wherein $R^A$ and $R^B$ are each independently selected from the group consisting of hydrogen and $C_{1-2}$alkyl; alternatively $R^A$ and $R^B$ are taken together with the nitrogen atom to which they are bound to form piperidin-1-yl, piperazin-1-yl and morpholin-4-yl;

or a pharmaceutically acceptable salt thereof.

3. A compound as in claim 2, wherein
$R^1$ is selected from the group consisting of

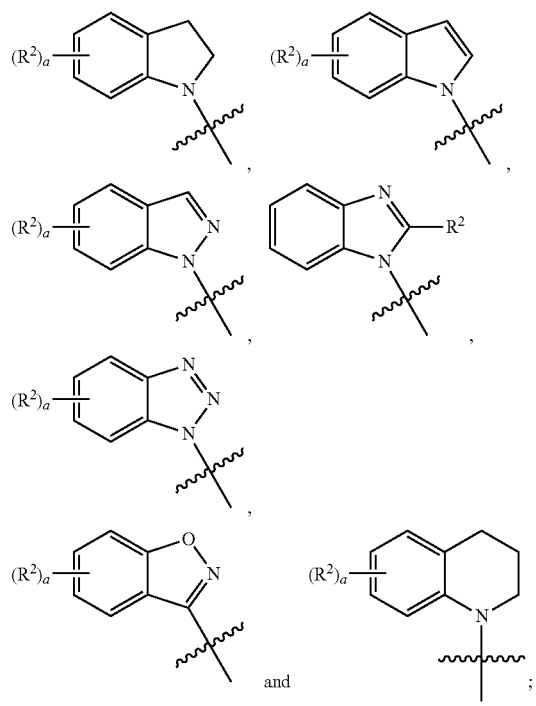

a is an integer from 0 to 2;
each $R^2$ is independently selected from the group consisting of halogen, $C_{1-2}$alkyl, $C_{1-2}$alkoxy and trifluoromethyl;
$R^3$ is selected from the group consisting of

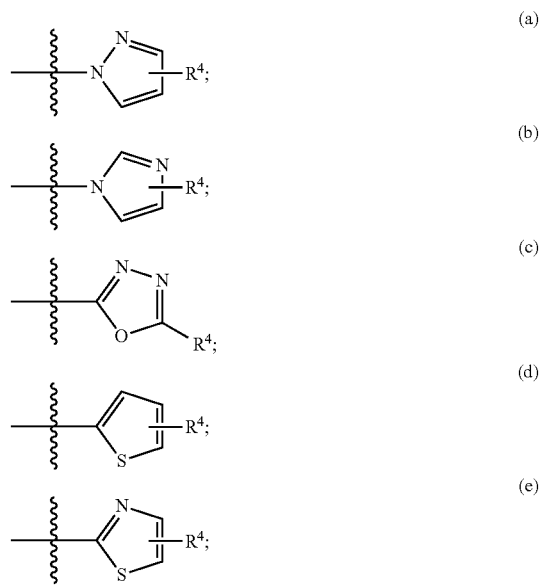

(a)

(b)

(c)

(d)

(e)

-continued

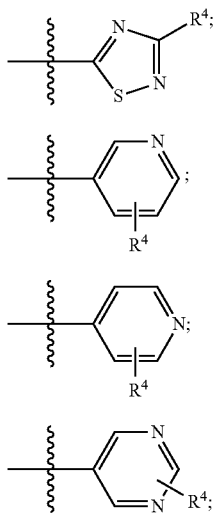

wherein R⁴ is selected from the group consisting of hydrogen, halogen, $C_{1-2}$alkyl, trifluoromethyl, —$C_{1-2}$alkyl-OH, $C_{1-2}$alkoxy, —$C_{1-2}$alkyl-O—$C_{1-2}$alkyl, —$C_{1-2}$alkyl-OC(O)—$C_{1-2}$alkyl, —NR$^A$R$^B$, —$C_{1-2}$alkyl-NR$^A$R$^B$, —C(O)—NR$^A$R$^B$, and —NR$^A$—C(O)—($C_{1-2}$alkyl);

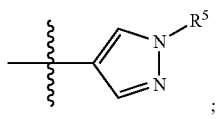

wherein R⁵ is selected from the group consisting of hydrogen, $C_{1-3}$alkyl, —$C_2$alkyl-OH, —$C_{2-3}$alkyl-O—$C_{1-2}$alkyl, —$C_{1-2}$alkyl-C(O)O—$C_{1-2}$alkyl, —$C_{2-4}$alkyl-NR$^A$R$^B$ and —$C_{1-2}$alkyl-C(O)NR$^A$R$^B$;
and

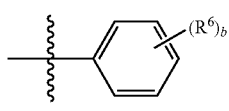

wherein b is 1; and wherein R⁶ is selected from the group consisting of, halogen, $C_{1-2}$alkyl, trifluoromethyl, —$C_{1-2}$alkyl-OH, —$CO_2H$, —C(O)O—$C_{1-4}$alkyl and —C(O)—NR$^A$R$^B$;
and wherein R$^A$ and R$^B$ are each independently selected from the group consisting of hydrogen and $C_{1-2}$alkyl; alternatively R$^A$ and R$^B$ are taken together with the nitrogen atom to which they are bound to form morpholin-4-yl;
or a pharmaceutically acceptable salt thereof.

4. A compound as in claim 3, wherein
R¹ is selected from the group consisting of indol-1-yl, 6-fluoro-indol-1-yl, indolin-1-yl, 4-fluoro-indolin-1-yl, 5-fluoro-indolin-1-yl, 6-fluoro-indolin-1-yl, 4-chloro-indolin-1-yl, 5-chloro-indolin-1-yl, 6-chloro-indolin-1-yl, 4,6-dichloro-indolin-1-yl, 6-methyl-indolin-1-yl, 6-methoxy-indolin-1-yl, 6-trifluoromethyl-indolin-1-yl, 1H-indazol-1-yl, 4-fluoro-1H-indazol-1-yl, 5-fluoro-1H-indazol-1-yl, 6-fluoro-1H-indazol-1-yl, 3-chloro-1H-indazol-1-yl, 4-chloro-1H-indazol-1-yl, 6-chloro-1H-indazol-1-yl, 4-trifluoromethyl-1H-indazol-1-yl, 6-trifluoromethyl-1H-indazol-1-yl, 2-(trifluoromethyl)-1H-benzo[d]imidazol-1-yl, 1H-benzo[d][1,2,3]triazol-1-yl, 5-fluoro-benzo[d]isoxazol-3-yl, 6-fluoro-benzo[d]isoxazol-1-yl, and 1,2,3,4-tetrahydroquinolin-1-yl;
R³ is selected from the group consisting of
(a) pyrazol-1-yl, 3-methyl-pyrazol-1-yl, 4-methyl-pyrazol-1-yl, 4-(hydroxymethyl)-pyrazol-1-yl, 4-(hydroxyethyl)-pyrazol-1-yl, 4-(methoxy-methyl)-pyrazol-1-yl, 4-(ethoxy-methyl)-pyrazol-1-yl, 4-(methylamino-methyl)-pyrazol-1-yl;
(b) imidazol-1-yl, 2-methyl-imidazol-1-yl, 4-methyl-imidazol-1-yl, 4-(hydroxymethyl)-imidazol-1-yl;
(c) 5-methyl-1,3,4-oxadiazol-2-yl, 5-(hydroxymethyl)-1,3,4-oxadiazol-2-yl, 5-(methylcarbonyl-oxy-methyl)-1,3,4-oxadiazol-2-yl;
(d) 4-methyl-thien-2-yl, 5-methyl-thien-2-yl;
(e) 4-methyl-thiazol-2-yl, 5-methyl-thiazol-2yl;
(f) 3-methyl-1,2,4-thiadiazol-5-yl;
(g) pyrid-3-yl, 6-methyl-pyrid-3-yl, 6-methoxy-pyrid-3-yl, 6-(hydroxymethyl)-pyrid-3-yl, 6-(trifluoromethyl)-pyrid-3-yl, 6-(methylamino-carbonyl)-pyrid-3-yl, 6-(dimethylamino)-pyrid-3-yl, 6-(methylcarbonyl-amino)-pyrid-3-yl;
(h) 2-methyl-pyrid-4-yl;
(i) 2-methyl-pyrimidin-5-yl, 2-methoxy-pyrimidin-5-yl;
(j) 1H-pyrazol-4-yl, 1-methyl-pyrazol-4-yl, 1-ethyl-pyrazol-4-yl, 1-(n-propyl)-pyrazol-4-yl, 1-(hydroxyethyl)-pyrazol-4-yl, 1-(ethoxycarbonyl-methyl)-pyrazol-4-yl, 1-(aminocarbonyl-methyl)-pyrazol-4-yl, 1-(methylamino-carbonyl-methyl)-pyrazol-4-yl, 1-(morpholin-4-yl-ethyl)-pyrazol-4-yl, 1-(ethoxy-ethyl)-pyrazol-4-yl; and
(k) 4-fluoro-phenyl, 4-methyl-phenyl, 4-(hydroxymethyl)-phenyl, 4-(trifluoromethyl)-phenyl, 4-(tert-butoxycarbonyl)-phenyl, 4-(carboxy)-phenyl, 4-(aminocarbonyl)-phenyl;
or a pharmaceutically acceptable salt thereof.

5. A compound as in claim 4, wherein
R¹ is selected from the group consisting of indol-1-yl, 6-fluoro-indolyl, indolin-1-yl, 6-fluoro-indolin-1-yl, 1H-indazol-1-yl, 4-fluoro-1H-indazol-1-yl, 6-fluoro-1H-indazol-1-yl, 3-chloro-1H-indazol-1-yl, 4-chloro-1H-indazol-1-yl, 6-chloro-1H-indazol-1-yl, 4-trifluoromethyl-1H-indazol-1-yl, 6-trifluoromethyl-1H-indazol-1-yl and 5-fluoro-benzo[d]isoxazol-3-yl;
R³ is selected from the group consisting of
(a) 4-methyl-pyrazol-1-yl, 4-(hydroxymethyl)-pyrazol-1-yl, 4-(hydroxyethyl)-pyrazol-1-yl, 4-(methoxy-methyl)-pyrazol-1-yl, 4-(ethoxy-methyl)-pyrazol-1-yl;
(b) 4-methyl-imidazol-1-yl, 4-(hydroxymethyl)-imidazol-1-yl;
(c) 5-(hydroxymethyl)-1,3,4-oxadiazol-2-yl;
(e) 4-methyl-thiazol-2-yl, 5-methyl-thiazol-2yl;
(f) 3-methyl-1,2,4-thiadiazol-5-yl;
(g) 6-methyl-pyrid-3-yl, 6-methoxy-pyrid-3-yl, 6-(hydroxymethyl)-pyrid-3-yl, 6-(trifluoromethyl)-pyrid-3-yl, 6-(methylamino-carbonyl)-pyrid-3-yl, 6-(dimethylamino)-pyrid-3-yl, 6-(methylcarbonyl-amino)-pyrid-3-yl;
(i) 2-methoxy-pyrimidin-5-yl;

(j) 1H-pyrazol-4-yl, 1-methyl-pyrazol-4-yl, 1-ethyl-pyrazol-4-yl, 1-(n-propyl)-pyrazol-4-yl, 1-(hydroxyethyl)-pyrazol-4-yl, 1-(ethoxycarbonyl-methyl)-pyrazol-4-yl, 1-(methylamino-carbonyl-methyl)-pyrazol-4-yl, 1-(ethoxy-ethyl)-pyrazol-4-yl; and
(k) 4-methyl-phenyl, 4-(hydroxymethyl)-phenyl;
or a pharmaceutically acceptable salt thereof.

6. A compound as in claim 5, wherein
$R^1$ is selected from the group consisting of indol-1-yl, 6-fluoro-indolyl, indolin-1-yl, 6-fluoro-indolin-1-yl, 6-fluoro-1H-indazol-1-yl, 3-chloro-1H-indazol-1-yl, 4-chloro-1H-indazol-1-yl, 6-chloro-1H-indazol-1-yl, 6-trifluoromethyl-1H-indazol-1-yl and 5-fluoro-benzo[d]isoxazol-3-yl;
$R^3$ is selected from the group consisting of
(a) 4-methyl-pyrazol-1-yl, 4-(hydroxymethyl)-pyrazol-1-yl, 4-(hydroxyethyl)-pyrazol-1-yl, 4-(methoxy-methyl)-pyrazol-1-yl, 4-(ethoxy-methyl)-pyrazol-1-yl;
(b) 4-methyl-imidazol-1-yl, 4-(hydroxymethyl)-imidazol-1-yl;
(c) 5-(hydroxymethyl)-1,3,4-oxadiazol-2-yl;
(e) 4-methyl-thiazol-2-yl, 5-methyl-thiazol-2yl;
(f) 3-methyl-1,2,4-thiadiazol-5-yl;
(g) 6-methyl-pyrid-3-yl, 6-methoxy-pyrid-3-yl, 6-(hydroxymethyl)-pyrid-3-yl, 6-(trifluoromethyl)-pyrid-3-yl, 6-(methylamino-carbonyl)-pyrid-3-yl, 6-(dimethylamino)-pyrid-3-yl, 6-(methylcarbonyl-amino)-pyrid-3-yl;
(i) 2-methoxy-pyrimidin-5-yl;
(j) 1H-pyrazol-4-yl, 1-methyl-pyrazol-4-yl, 1-ethyl-pyrazol-4-yl, 1-(n-propyl)-pyrazol-4-yl, 1-(hydroxyethyl)-pyrazol-4-yl, 1-(ethoxycarbonyl-methyl)-pyrazol-4-yl, 1-(methylamino-carbonyl-methyl)-pyrazol-4-yl, 1-(ethoxy-ethyl)-pyrazol-4-yl; and
(k) 4-(hydroxymethyl)-phenyl;
or a pharmaceutically acceptable salt thereof.

7. A compound as in claim 4, wherein
$R^1$ is selected from the group consisting of indol-1-yl, indolin-1-yl, 6-fluoro-indolin-1-yl, 3-chloro-1H-indazol-1-yl, 4-chloro-1H-indazol-1-yl, 6-chloro-1H-indazol-1-yl, 6-trifluoromethyl-1H-indazol-1-yl and 5-fluoro-benzo[d]isoxazol-3-yl;
$R^3$ is selected from the group consisting of
(a) 4-methyl-pyrazol-1-yl, 4-(hydroxymethyl)-pyrazol-1-yl, 4-(methoxy-methyl)-pyrazol-1-yl, 4-(ethoxy-methyl)-pyrazol-1-yl;
(b) 4-methyl-imidazol-1-yl, 4-(hydroxymethyl)-imidazol-1-yl;
(c) 5-(hydroxymethyl)-1,3,4-oxadiazol-2-yl;
(e) 4-methyl-thiazol-2-yl, 5-methyl-thiazol-2yl;
(f) 3-methyl-1,2,4-thiadiazol-5-yl;
(g) 6-methyl-pyrid-3-yl, 6-methoxy-pyrid-3-yl, 6-(hydroxymethyl)-pyrid-3-yl, 6-(trifluoromethyl)-pyrid-3-yl, 6-(dimethylamino)-pyrid-3-yl, 6-(methylcarbonyl-amino)-pyrid-3-yl;
(i) 2-methoxy-pyrimidin-5-yl;
(j) 1-methyl-pyrazol-4-yl, 1-ethyl-pyrazol-4-yl, 1-(n-propyl)-pyrazol-4-yl, 1-(methylamino-carbonyl-methyl)-pyrazol-4-yl and 1-(ethoxy-ethyl)-pyrazol-4-yl;
or a pharmaceutically acceptable salt thereof.

8. A compound as in claim 4, wherein
$R^1$ is selected from the group consisting of indol-1-yl, 6-fluoro-indol-1-yl, indolin-1-yl, 5-fluoro-indolin-1-yl, 6-fluoro-indolin-1-yl, 6-chloro-indolin-1-yl, 6-trifluoromethyl-indolin-1-yl, 1H-indazol-1-yl, 4-fluoro-1H-indazol-1-yl, 6-fluoro-1H-indazol-1-yl, 3-chloro-1H-indazol-1-yl, 4-chloro-1H-indazol-1-yl, 6-chloro-1H-indazol-1-yl and 5-fluoro-benzo[d]isoxazol-3-yl;
$R^3$ is selected from the group consisting of
(a) 3-methyl-pyrazol-1-yl, 4-methyl-pyrazol-1-yl, 4-(hydroxymethyl)-pyrazol-1-yl, 4-(hydroxyethyl)-pyrazol-1-yl, 4-(methoxy-methyl)-pyrazol-1-yl, 4-(ethoxy-methyl)-pyrazol-1-yl;
(b) 4-methyl-imidazol-1-yl, 4-(hydroxymethyl)-imidazol-1-yl;
(c) 5-(hydroxymethyl)-1,3,4-oxadiazol-2-yl;
(d) 4-methyl-thien-2-yl, 5-methyl-thien-2-yl;
(e) 4-methyl-thiazol-2-yl, 5-methyl-thiazol-2yl;
(f) 3-methyl-1,2,4-thiadiazol-5-yl;
(g) 6-methyl-pyrid-3-yl, 6-methoxy-pyrid-3-yl, 6-(hydroxymethyl)-pyrid-3-yl, 6-(trifluoromethyl)-pyrid-3-yl, 6-(methylamino-carbonyl)-pyrid-3-yl, 6-(dimethylamino)-pyrid-3-yl, 6-(methylcarbonyl-amino)-pyrid-3-yl;
(h) 2-methyl-pyrid-4-yl;
(i) 2-methoxy-pyrimidin-5-yl;
(j) 1H-pyrazol-4-yl, 1-methyl-pyrazol-4-yl, 1-ethyl-pyrazol-4-yl, 1-(n-propyl)-pyrazol-4-yl, 1-(hydroxyethyl)-pyrazol-4-yl, 1-(ethoxycarbonyl-methyl)-pyrazol-4-yl, 1-(methylamino-carbonyl-methyl)-pyrazol-4-yl, 1-(ethoxy-ethyl)-pyrazol-4-yl; and
(k) 4-methyl-phenyl, 4-(hydroxymethyl)-phenyl, 4-(trifluoromethyl)-phenyl;
or a pharmaceutically acceptable salt thereof.

9. A compound as in claim 8, wherein
$R^1$ is selected from the group consisting of 6-fluoro-indol-1-yl, indolin-1-yl, 6-fluoro-indolin-1-yl, 6-chloro-indolin-1-yl, 6-trifluoromethyl-indolin-1-yl, 1H-indazol-1-yl, 6-fluoro-1H-indazol-1-yl, 3-chloro-1H-indazol-1-yl, 4-chloro-1H-indazol-1-yl, 6-chloro-1H-indazol-1-yl and 5-fluoro-benzo[d]isoxazol-3-yl;
$R^3$ is selected from the group consisting of
(a) 4-methyl-pyrazol-1-yl, 4-(hydroxymethyl)-pyrazol-1-yl, 4-(hydroxyethyl)-pyrazol-1-yl, 4-(methoxy-methyl)-pyrazol-1-yl, 4-(ethoxy-methyl)-pyrazol-1-yl;
(b) 4-(hydroxymethyl)-imidazol-1-yl;
(c) 5-(hydroxymethyl)-1,3,4-oxadiazol-2-yl;
(d) 4-methyl-thien-2-yl, 5-methyl-thien-2-yl;
(e) 4-methyl-thiazol-2-yl, 5-methyl-thiazol-2yl;
(f) 3-methyl-1,2,4-thiadiazol-5-yl;
(g) 6-methyl-pyrid-3-yl, 6-methoxy-pyrid-3-yl, 6-(hydroxymethyl)-pyrid-3-yl, 6-(trifluoromethyl)-pyrid-3-yl, 6-(methylamino-carbonyl)-pyrid-3-yl, 6-(dimethylamino)-pyrid-3-yl, 6-(methylcarbonyl-amino)-pyrid-3-yl;
(h) 2-methyl-pyrid-4-yl;
(i) 2-methoxy-pyrimidin-5-yl;
(j) 1H-pyrazol-4-yl, 1-methyl-pyrazol-4-yl, 1-ethyl-pyrazol-4-yl, 1-(hydroxyethyl)-pyrazol-4-yl, 1-(ethoxycarbonyl-methyl)-pyrazol-4-yl, 1-(methylamino-carbonyl-methyl)-pyrazol-4-yl; and
(k) 4-methyl-phenyl, 4-(hydroxymethyl)-phenyl;
or a pharmaceutically acceptable salt thereof.

10. A compound as in claim 8, wherein
$R^1$ is selected from the group consisting of 6-fluoro-indolin-1-yl, 6-fluoro-1H-indazol-1-yl, 3-chloro-1H-indazol-1-yl, 4-chloro-1H-indazol-1-yl and 5-fluoro-benzo[d]isoxazol-3-yl;
$R^3$ is selected from the group consisting of
(a) 4-(hydroxymethyl)-pyrazol-1-yl, 4-(hydroxyethyl)-pyrazol-1-yl, 4-(ethoxy-methyl)-pyrazol-1-yl;
(b) 4-(hydroxymethyl)-imidazol-1-yl;
(c) 5-(hydroxymethyl)-1,3,4-oxadiazol-2-yl;

(d) 4-methyl-thien-2-yl, 5-methyl-thien-2-yl;
(e) 4-methyl-thiazol-2-yl, 5-methyl-thiazol-2yl;
(g) 6-methyl-pyrid-3-yl, 6-methoxy-pyrid-3-yl, 6-(hydroxymethyl)-pyrid-3-yl, 6-(trifluoromethyl)-pyrid-3-yl, 6-(methylamino-carbonyl)-pyrid-3-yl;
(h) 2-methyl-pyrid-4-yl;
(i) 2-methoxy-pyrimidin-5-yl;
(j) 1-methyl-pyrazol-4-yl, 1-(hydroxyethyl)-pyrazol-4-yl, 1-(methylamino-carbonyl-methyl)-pyrazol-4-yl; and
(k) 4-methyl-phenyl, 4-(hydroxymethyl)-phenyl;
or a pharmaceutically acceptable salt thereof.

11. A compound as in claim 4, wherein
$R^1$ is selected from the group consisting of 6-fluoro-indolin-1-yl and 5-fluoro-benzo[d]isoxazol-3-yl;
$R^3$ is selected from the group consisting of (a) 4-(ethoxymethyl)-pyrazol-1-yl; (e) 4-methyl-thiazol-2-yl; (g) 6-methyl-pyrid-3-yl, 6-methoxy-pyrid-3-yl, 6-(hydroxymethyl)-pyrid-3-yl; and (j) 1-methyl-pyrazol-4-yl;
or a pharmaceutically acceptable salt thereof.

12. A pharmaceutical composition comprising a pharmaceutically acceptable carrier and a compound of claim 1.

13. A pharmaceutical composition made by mixing a compound of claim 1 and a pharmaceutically acceptable carrier.

* * * * *